US 10,646,342 B1

(12) United States Patent
Marr et al.

(10) Patent No.: US 10,646,342 B1
(45) Date of Patent: May 12, 2020

(54) MITRAL VALVE SPACER DEVICE

(71) Applicant: EDWARDS LIFESCIENCES CORPORATION, Irvine, CA (US)

(72) Inventors: Devin H. Marr, Irvine, CA (US); Sergio Delgado, Irvine, CA (US); Eric Robert Dixon, Villa Park, CA (US); David M. Taylor, Lake Forest, CA (US); Asher L. Metchik, Hawthorne, CA (US); Matthew T. Winston, Aliso Viejo, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 16/733,659

(22) Filed: Jan. 3, 2020

Related U.S. Application Data

(63) Continuation of application No. 15/973,892, filed on May 8, 2018.
(Continued)

(51) Int. Cl.
*A61F 2/24* (2006.01)
*A61B 17/128* (2006.01)
(Continued)

(52) U.S. Cl.
CPC .......... *A61F 2/246* (2013.01); *A61B 17/1227* (2013.01); *A61B 17/1285* (2013.01);
(Continued)

(58) Field of Classification Search
CPC ...... A61F 2/246; A61F 2/2466; A61F 2/2463; A61F 2220/0016; A61F 2220/0008;
(Continued)

(56) References Cited

U.S. PATENT DOCUMENTS

| 3,874,388 A | 4/1975 | King et al. |
| 4,035,849 A | 7/1977 | Angel et al. |

(Continued)

FOREIGN PATENT DOCUMENTS

| CN | 1142351 | 2/1997 |
| DE | 19532846 | 3/1997 |

(Continued)

OTHER PUBLICATIONS

Al Zaibag et al., "Percutaneous Balloon Valvotomy in Tricuspid Stenosis", British Heart Journal, vol. 57, No. 1, Jan. 1987.
(Continued)

*Primary Examiner* — Julian W Woo
(74) *Attorney, Agent, or Firm* — Thomas C. Richardson

(57) ABSTRACT

A delivery system includes an elongate shaft, a handle, a first clasp control member, a second clasp control member, and an actuator. The handle is connected to a proximal portion of the elongate shaft. The first and second clasp control members each extend into a distal portion of the elongate shaft, through at least a portion of the elongate shaft, out of the proximal portion of the elongate shaft, and through the handle. The actuator is coupled to the handle and has a first side portion connected to the first clasp control and a second side portion connected to the second clasp control. The first side portion and the second side portion are releasably couplable such that when the first side portion and the second side portion are coupled, proximal movement of the actuator proximally pulls both the first clasp control member and the second clasp control member, and such that when the first side portion and the second side portion are uncoupled, individual proximal movements of the first side portion and the second side portion independently pull the first clasp control member and the second clasp control member, respectively.

20 Claims, 45 Drawing Sheets

Related U.S. Application Data

(60) Provisional application No. 62/659,253, filed on Apr. 18, 2018, provisional application No. 62/571,552, filed on Oct. 12, 2017, provisional application No. 62/504,389, filed on May 10, 2017.

(51) Int. Cl.
*A61B 17/122* (2006.01)
*A61B 17/00* (2006.01)

(52) U.S. Cl.
CPC .......... *A61F 2/2463* (2013.01); *A61F 2/2466* (2013.01); *A61B 2017/00783* (2013.01); *A61F 2210/0014* (2013.01); *A61F 2220/0008* (2013.01); *A61F 2220/0016* (2013.01); *A61F 2220/0075* (2013.01)

(58) Field of Classification Search
CPC ..... A61F 2210/0014; A61F 2220/0075; A61B 17/1227; A61B 17/128; A61B 2017/00783
See application file for complete search history.

(56) References Cited

U.S. PATENT DOCUMENTS

| | | |
|---|---|---|
| 4,340,091 A | 7/1982 | Skelton et al. |
| 4,506,669 A | 3/1985 | Blake, III |
| 4,590,937 A | 5/1986 | Deniega |
| 4,592,340 A | 6/1986 | Boyles |
| 4,693,248 A | 9/1987 | Failla |
| 4,803,983 A | 2/1989 | Siegel |
| 4,955,895 A | 9/1990 | Sugiyama et al. |
| 4,994,077 A | 2/1991 | Dobben |
| 5,059,177 A | 10/1991 | Towne et al. |
| 5,125,895 A | 6/1992 | Buchbinder et al. |
| 5,171,252 A | 12/1992 | Friedland |
| 5,176,698 A | 1/1993 | Burns et al. |
| 5,192,297 A | 3/1993 | Hull |
| 5,195,962 A | 3/1993 | Martin et al. |
| 5,201,757 A | 4/1993 | Heyn et al. |
| 5,266,073 A | 11/1993 | Wall |
| 5,292,326 A | 3/1994 | Green et al. |
| 5,325,845 A | 7/1994 | Adair |
| 5,327,905 A | 7/1994 | Avitall |
| 5,358,496 A | 10/1994 | Ortiz et al. |
| 5,363,861 A | 11/1994 | Edwards et al. |
| 5,370,685 A | 12/1994 | Stevens |
| 5,389,077 A | 2/1995 | Melinyshyn et al. |
| 5,411,552 A | 5/1995 | Henning et al. |
| 5,450,860 A | 9/1995 | O'Connor |
| 5,456,674 A | 10/1995 | Box et al. |
| 5,474,057 A | 12/1995 | Makower et al. |
| 5,478,353 A | 12/1995 | Yoon |
| 5,487,746 A | 1/1996 | Yu et al. |
| 5,554,185 A | 9/1996 | Block et al. |
| 5,564,004 A | 10/1996 | Christoudias |
| 5,591,195 A | 1/1997 | Taheri et al. |
| 5,599,305 A | 2/1997 | Herman et al. |
| 5,607,462 A | 3/1997 | Imran |
| 5,609,598 A | 3/1997 | Laufer et al. |
| 5,611,794 A | 3/1997 | Sauer et al. |
| 5,626,607 A | 5/1997 | Malecki et al. |
| 5,632,760 A | 5/1997 | Sheiban |
| 5,639,274 A | 6/1997 | Fischel et al. |
| 5,695,504 A | 12/1997 | Gifford et al. |
| 5,716,417 A | 2/1998 | Girard et al. |
| 5,727,569 A | 3/1998 | Benetti et al. |
| 5,728,068 A | 3/1998 | Leone et al. |
| 5,741,297 A | 4/1998 | Morris |
| 5,749,890 A | 5/1998 | Shaknovich |
| 5,776,142 A | 7/1998 | Gunderson |
| 5,782,746 A | 7/1998 | Wright |
| 5,782,809 A | 7/1998 | Umeno |
| 5,797,960 A | 8/1998 | Stevens et al. |
| 5,824,044 A | 10/1998 | Quiachon |
| 5,836,311 A | 11/1998 | Borst et al. |
| 5,840,081 A | 11/1998 | Anderson et al. |
| 5,843,076 A | 12/1998 | Webster, Jr. et al. |
| 5,843,182 A | 12/1998 | Inoue |
| 5,855,590 A | 1/1999 | Malecki et al. |
| 5,861,024 A | 1/1999 | Rashidi |
| 5,885,271 A | 3/1999 | Hamilton et al. |
| 5,888,247 A | 3/1999 | Benetti |
| 5,891,017 A | 4/1999 | Swindle et al. |
| 5,891,112 A | 4/1999 | Samson |
| 5,894,843 A | 4/1999 | Benetti et al. |
| 5,908,405 A | 6/1999 | Imron |
| 5,916,147 A | 6/1999 | Boury |
| 5,921,979 A | 7/1999 | Kovac et al. |
| 5,944,738 A | 8/1999 | Amplatz et al. |
| 5,957,835 A | 9/1999 | Anderson et al. |
| 5,961,536 A | 10/1999 | Mickley |
| 5,968,068 A | 10/1999 | Dehdashtian et al. |
| 5,972,020 A | 10/1999 | Carpenter et al. |
| 5,980,534 A | 11/1999 | Gimpelson |
| 6,004,329 A | 12/1999 | Myers et al. |
| 6,010,531 A | 1/2000 | Donlon et al. |
| 6,017,358 A | 1/2000 | Yoon et al. |
| 6,019,777 A | 2/2000 | Mackenzie |
| 6,027,510 A | 2/2000 | Alt |
| 6,033,381 A | 3/2000 | Kontos |
| 6,086,600 A | 7/2000 | Kortenbach |
| 6,120,496 A | 9/2000 | Whayne et al. |
| 6,132,370 A | 10/2000 | Furnish et al. |
| 6,143,016 A | 11/2000 | Bleam et al. |
| 6,162,208 A | 12/2000 | Hipps |
| 6,162,239 A | 12/2000 | Manhes |
| 6,165,183 A | 12/2000 | Kuehn et al. |
| 6,168,614 B1 | 1/2001 | Anderson et al. |
| 6,174,327 B1 | 1/2001 | Martens |
| 6,182,664 B1 | 2/2001 | Cosgrove et al. |
| 6,193,732 B1 | 2/2001 | Frantzen et al. |
| 6,193,734 B1 | 2/2001 | Bolduc et al. |
| 6,200,315 B1 | 3/2001 | Gaiser et al. |
| 6,217,585 B1 | 4/2001 | Houser et al. |
| 6,235,050 B1 | 5/2001 | Quiachon et al. |
| 6,241,743 B1 | 6/2001 | Ievin et al. |
| 6,251,092 B1 | 6/2001 | Quin et al. |
| 6,269,819 B1 | 8/2001 | Oz et al. |
| 6,269,829 B1 | 8/2001 | Chen et al. |
| 6,312,447 B1 | 11/2001 | Grimes |
| 6,379,372 B1 | 4/2002 | Dehdashtian et al. |
| 6,383,171 B1 | 5/2002 | Gifford et al. |
| 6,454,799 B1 | 9/2002 | Schreck |
| 6,458,153 B1 | 10/2002 | Bailey et al. |
| 6,461,366 B1 | 10/2002 | Seguin |
| 6,461,382 B1 | 10/2002 | Cao |
| 6,468,285 B1 | 10/2002 | Hsu et al. |
| 6,471,672 B1 | 10/2002 | Brown et al. |
| 6,500,147 B2 | 12/2002 | Omaleki et al. |
| 6,508,806 B1 | 1/2003 | Hoste |
| 6,508,825 B1 | 1/2003 | Selmon et al. |
| 6,514,228 B1 | 2/2003 | Hamilton |
| 6,527,979 B2 | 3/2003 | Constatz et al. |
| 6,530,933 B1 | 3/2003 | Yeung et al. |
| 6,537,290 B2 | 3/2003 | Adams et al. |
| 6,544,215 B1 | 4/2003 | Becini et al. |
| 6,579,305 B1 | 6/2003 | Lashinski |
| 6,582,462 B1 | 6/2003 | Anderson et al. |
| 6,626,930 B1 | 9/2003 | Allen et al. |
| 6,629,534 B1 | 10/2003 | St. Goar et al. |
| 6,552,578 B1 | 11/2003 | Bailey et al. |
| 6,652,578 B2 | 11/2003 | Bailey et al. |
| 6,719,767 B1 | 4/2004 | Kimblad |
| 6,730,118 B2 | 5/2004 | Spanser et al. |
| 6,733,525 B2 | 5/2004 | Yang et al. |
| 6,764,504 B2 | 7/2004 | Wag |
| 6,764,510 B2 | 7/2004 | Vidlund et al. |
| 6,767,362 B2 | 7/2004 | Schreck |
| 6,770,083 B2 | 8/2004 | Seguin |
| 6,830,584 B1 | 12/2004 | Seguin |
| 6,837,867 B2 | 1/2005 | Kortelling |
| 6,855,137 B2 | 2/2005 | Bon |

(56) References Cited

U.S. PATENT DOCUMENTS

| | | | |
|---|---|---|---|
| 6,893,460 B2 | 5/2005 | Spenser et al. |
| 6,908,481 B2 | 6/2005 | Cribier |
| 6,911,039 B2 | 6/2005 | Shiu et al. |
| 6,913,614 B2 | 7/2005 | Marino et al. |
| 6,939,337 B2 | 9/2005 | Parker et al. |
| 6,945,956 B2 | 9/2005 | Waldhauser et al. |
| 7,001,094 B2 | 3/2006 | Rapacki et al. |
| 7,018,406 B2 | 3/2006 | Seguin |
| 7,018,408 B2 | 3/2006 | Bailey et al. |
| 7,048,754 B2 | 5/2006 | Martin et al. |
| 7,101,395 B2 | 9/2006 | Tremulis et al. |
| 7,125,421 B2 | 10/2006 | Tremulis et al. |
| 7,137,993 B2 | 11/2006 | Acosta |
| 7,226,467 B2 * | 6/2007 | Lucatero ............ A61M 25/0136 |
| | | | 606/213 |
| 7,276,084 B2 | 10/2007 | Yang et al. |
| 7,288,097 B2 | 10/2007 | Seguin |
| 7,318,278 B2 | 1/2008 | Zhang et al. |
| 7,320,702 B2 | 1/2008 | Hammersmark |
| 7,320,704 B2 | 1/2008 | Lashinski |
| 7,371,210 B2 | 5/2008 | Rock et al. |
| 7,374,571 B2 | 5/2008 | Pease et al. |
| 7,393,360 B2 | 7/2008 | Spenser et al. |
| 7,435,257 B2 | 10/2008 | Lashinski et al. |
| 7,464,712 B2 | 12/2008 | Oz et al. |
| 7,509,959 B2 | 3/2009 | Oz et al. |
| 7,510,575 B2 | 3/2009 | Spenser et al. |
| 7,569,062 B1 * | 8/2009 | Kuehn ................. A61B 17/064 |
| | | | 606/139 |
| 7,585,321 B2 | 9/2009 | Cribier |
| 7,594,926 B2 | 9/2009 | Linder et al. |
| 7,597,709 B2 | 10/2009 | Goodin |
| 7,618,446 B2 | 11/2009 | Anderson et al. |
| 7,635,329 B2 * | 12/2009 | Goldfarb ............ A61B 17/0401 |
| | | | 600/37 |
| 7,655,034 B2 | 2/2010 | Mitchell |
| 7,682,369 B2 | 3/2010 | Seguin |
| 7,731,706 B2 | 6/2010 | Potter |
| 7,744,609 B2 | 6/2010 | Allen et al. |
| 7,748,389 B2 | 7/2010 | Salahieh et al. |
| 7,749,266 B2 | 7/2010 | Forster et al. |
| 7,753,932 B2 | 7/2010 | Gingrich et al. |
| 7,758,596 B2 | 7/2010 | Oz et al. |
| 7,780,723 B2 | 8/2010 | Taylor |
| 7,785,366 B2 | 8/2010 | Maurer et al. |
| 7,803,185 B2 | 9/2010 | Gabbay |
| 7,824,443 B2 | 11/2010 | Salahieh et al. |
| 7,959,661 B2 | 6/2011 | Hijlkema et al. |
| 7,981,123 B2 | 7/2011 | Seguin |
| 7,988,724 B2 | 8/2011 | Salahieh et al. |
| 7,993,394 B2 | 8/2011 | Harlton et al. |
| 8,029,556 B2 | 10/2011 | Rave |
| 8,052,750 B2 | 11/2011 | Tuval et al. |
| 8,070,805 B2 | 12/2011 | Vidlund et al. |
| 8,096,985 B2 | 1/2012 | Legaspi et al. |
| 8,133,239 B2 | 3/2012 | Oz et al. |
| 8,147,542 B2 | 4/2012 | Maisano et al. |
| 8,167,932 B2 | 5/2012 | Bourang et al. |
| 8,206,437 B2 | 6/2012 | Bohoffer et al. |
| 8,216,301 B2 | 7/2012 | Bonhoeffer et al. |
| 8,303,653 B2 | 11/2012 | Bonhoeffer et al. |
| 8,313,525 B2 | 11/2012 | Yosi et al. |
| RE43,882 E | 12/2012 | Hopkins |
| 8,348,995 B2 | 1/2013 | Yosi et al. |
| 8,348,996 B2 | 1/2013 | Yosi et al. |
| 8,414,643 B2 | 4/2013 | Yosi et al. |
| 8,449,599 B2 | 5/2013 | Chau et al. |
| 8,449,606 B2 | 5/2013 | Eliasen et al. |
| 8,460,368 B2 | 6/2013 | Taylor et al. |
| 8,470,028 B2 | 6/2013 | Thornton et al. |
| 8,475,523 B2 | 7/2013 | Duffy |
| 8,480,730 B2 | 7/2013 | Maurer et al. |
| 8,540,767 B2 | 9/2013 | Zhang |
| 8,568,472 B2 | 10/2013 | Marchand et al. |
| 8,579,965 B2 | 11/2013 | Bonhoeffer et al. |
| 8,585,756 B2 | 11/2013 | Bonhoeffer et al. |
| 8,652,145 B2 | 2/2014 | Maimon et al. |
| 8,652,202 B2 | 2/2014 | Alon et al. |
| 8,668,733 B2 | 3/2014 | Salahieh et al. |
| 8,721,665 B2 | 5/2014 | Oz et al. |
| 8,771,347 B2 | 7/2014 | DeBoer et al. |
| 8,778,017 B2 | 7/2014 | Eliasen et al. |
| 8,834,564 B2 | 9/2014 | Tuval et al. |
| 8,840,663 B2 | 9/2014 | Salahieh et al. |
| 8,876,894 B2 | 11/2014 | Tuval et al. |
| 8,876,895 B2 | 11/2014 | Tuval et al. |
| 8,945,177 B2 | 2/2015 | Dell et al. |
| 9,011,468 B2 * | 4/2015 | Ketai .................... A61B 17/08 |
| | | | 606/151 |
| 9,034,032 B2 | 5/2015 | McLea et al. |
| 9,061,119 B2 | 6/2015 | Le et al. |
| 9,119,716 B2 | 9/2015 | Lee |
| 9,155,619 B2 | 10/2015 | Liu et al. |
| 9,168,131 B2 | 10/2015 | Yohaan et al. |
| 9,198,757 B2 | 12/2015 | Schroeder et al. |
| 9,259,317 B2 | 2/2016 | Wilson et al. |
| 9,301,834 B2 | 4/2016 | Tuval et al. |
| 9,308,360 B2 | 4/2016 | Bishop et al. |
| 9,387,071 B2 | 7/2016 | Tuval et al. |
| 9,427,327 B2 | 8/2016 | Gene |
| 9,439,763 B2 | 9/2016 | Geist et al. |
| 9,510,837 B2 | 12/2016 | Seguin |
| 9,510,946 B2 | 12/2016 | Chau et al. |
| 9,572,660 B2 | 2/2017 | Braido et al. |
| 9,642,704 B2 | 5/2017 | Tuval et al. |
| 9,700,445 B2 | 7/2017 | Martin et al. |
| 9,740,918 B1 | 8/2017 | Balasubramanian et al. |
| 9,775,963 B2 | 10/2017 | Miller |
| 9,795,477 B2 | 10/2017 | Tran et al. |
| D809,139 S | 1/2018 | Marsot et al. |
| 9,867,700 B2 | 1/2018 | Bakis et al. |
| 9,889,002 B2 | 2/2018 | Bonhoeffer et al. |
| 9,949,824 B2 | 4/2018 | Bonhoeffer et al. |
| 10,076,327 B2 | 9/2018 | Ellis et al. |
| 10,076,415 B1 | 9/2018 | Metchik et al. |
| 10,105,221 B2 | 10/2018 | Siegel |
| 10,105,222 B1 | 10/2018 | Metchik et al. |
| 10,111,751 B1 | 10/2018 | Metchik et al. |
| 10,123,873 B1 | 11/2018 | Metchik et al. |
| 10,130,475 B1 | 11/2018 | Metchik et al. |
| 10,136,993 B1 | 11/2018 | Metchik et al. |
| 10,159,570 B1 | 12/2018 | Metchik et al. |
| 10,188,392 B2 * | 1/2019 | Wei .................... A61B 17/1285 |
| 10,226,309 B2 | 3/2019 | Ho et al. |
| 10,231,837 B1 | 3/2019 | Metchik et al. |
| 10,238,494 B2 | 3/2019 | Meniven et al. |
| 10,238,495 B2 | 3/2019 | Marsot et al. |
| 10,299,924 B2 | 5/2019 | Kizuka |
| 10,376,673 B2 | 8/2019 | VaHoven et al. |
| 2001/0002445 A1 | 5/2001 | Vesaly |
| 2001/0005787 A1 | 6/2001 | Mehmet et al. |
| 2001/0007082 A1 | 7/2001 | Dusbabek et al. |
| 2002/0013571 A1 | 1/2002 | Goldfarb et al. |
| 2002/0032481 A1 | 3/2002 | Gabbay |
| 2002/0058995 A1 | 5/2002 | Stevens |
| 2002/0107531 A1 | 8/2002 | Schreck et al. |
| 2002/0165461 A1 | 11/2002 | Hayzelden |
| 2002/0173811 A1 | 11/2002 | Tu et al. |
| 2002/0183787 A1 | 12/2002 | Wahr et al. |
| 2003/0040792 A1 | 2/2003 | Gabay |
| 2003/0050694 A1 | 3/2003 | Yang et al. |
| 2003/0074628 A1 | 4/2003 | Lee |
| 2003/0120341 A1 | 6/2003 | Shannib et al. |
| 2003/0187467 A1 | 10/2003 | Schreck |
| 2003/0191516 A1 | 10/2003 | Weldon et al. |
| 2003/0198722 A1 | 10/2003 | Johnston et al. |
| 2003/0208231 A1 | 11/2003 | Williamson et al. |
| 2004/0003819 A1 | 1/2004 | Goldfarb et al. |
| 2004/0034365 A1 | 2/2004 | Lentz et al. |
| 2004/0039343 A1 | 2/2004 | Eppstein et al. |
| 2004/0044350 A1 | 3/2004 | Martin |
| 2004/0044365 A1 | 3/2004 | Bachman |
| 2004/0049207 A1 | 3/2004 | Goldfarb et al. |
| 2004/0093061 A1 | 5/2004 | Acosta |

(56) References Cited

U.S. PATENT DOCUMENTS

| | | |
|---|---|---|
| 2004/0127981 A1 | 7/2004 | Randert et al. |
| 2004/0127982 A1 | 7/2004 | Machold et al. |
| 2004/0133263 A1 | 7/2004 | Dushbabek et al. |
| 2004/0143197 A1 | 7/2004 | Soukup et al. |
| 2004/0148009 A1 | 7/2004 | Buzzard |
| 2004/0181206 A1 | 9/2004 | Chiu et al. |
| 2004/0181238 A1 | 9/2004 | Zarbatany et al. |
| 2004/0186563 A1 | 9/2004 | Libbi |
| 2004/0186565 A1 | 9/2004 | Schreck |
| 2004/0147943 A1 | 10/2004 | Khairkhahan |
| 2004/0204683 A1 | 10/2004 | McGuckin, Jr. et al. |
| 2004/0210304 A1 | 10/2004 | Seguin et al. |
| 2004/0210307 A1 | 10/2004 | Khairkhahan |
| 2004/0220593 A1 | 11/2004 | Greenhalgh |
| 2004/0236411 A1 | 11/2004 | Sarac et al. |
| 2004/0260389 A1 | 12/2004 | Case et al. |
| 2005/0027305 A1 | 2/2005 | Shui et al. |
| 2005/0049618 A1 | 3/2005 | Masuda et al. |
| 2005/0075731 A1 | 4/2005 | Artof et al. |
| 2005/0080474 A1 | 4/2005 | Andreas |
| 2005/0080476 A1 | 4/2005 | Gunderson |
| 2005/0090834 A1 | 4/2005 | Chiang et al. |
| 2005/0096736 A1 | 5/2005 | Osse et al. |
| 2005/0113910 A1 | 5/2005 | Paiagua et al. |
| 2005/0137688 A1 | 6/2005 | Salahieh et al. |
| 2005/0137689 A1 | 6/2005 | Sacahieh |
| 2005/0137693 A1 | 6/2005 | Haug et al. |
| 2005/0137697 A1 | 6/2005 | Salahieh et al. |
| 2005/0143767 A1 | 6/2005 | Kimura et al. |
| 2005/0149160 A1 | 7/2005 | McFerran |
| 2005/0165429 A1 | 7/2005 | Douglas et al. |
| 2005/0203614 A1 | 9/2005 | Forster et al. |
| 2005/0203617 A1 | 9/2005 | Forster et al. |
| 2005/0245894 A1 | 11/2005 | Zadno-Azizi |
| 2005/0251183 A1 | 11/2005 | Buckman et al. |
| 2005/0288786 A1 | 12/2005 | Chanduszko |
| 2006/0025847 A1 | 2/2006 | Bergheim et al. |
| 2006/0100649 A1 | 5/2006 | Hart |
| 2006/0122647 A1 | 6/2006 | Callaghan et al. |
| 2006/0142837 A1 | 6/2006 | Haverkost et al. |
| 2006/0149360 A1 | 7/2006 | Schwammenthal et al. |
| 2006/0155358 A1 | 7/2006 | LaDuca et al. |
| 2006/0178700 A1 | 8/2006 | Quinn |
| 2006/0224169 A1 | 10/2006 | Weisenburgh et al. |
| 2006/0259136 A1 | 11/2006 | Nguyen et al. |
| 2006/0276813 A1 | 12/2006 | Greenberg |
| 2006/0282150 A1 | 12/2006 | Olson et al. |
| 2006/0287719 A1 | 12/2006 | Rowe et al. |
| 2007/0005131 A1 | 1/2007 | Taylor |
| 2007/0010877 A1 | 1/2007 | Salahieh et al. |
| 2007/0021779 A1 | 1/2007 | Garvin et al. |
| 2007/0032807 A1 | 2/2007 | Ortiz et al. |
| 2007/0073389 A1 | 3/2007 | Bolduc et al. |
| 2007/0088431 A1 | 4/2007 | Bourang et al. |
| 2007/0093857 A1 | 4/2007 | Rogers et al. |
| 2007/0112358 A1 | 5/2007 | Abott et al. |
| 2007/0112422 A1 | 5/2007 | Dehdashtian |
| 2007/0191154 A1 | 8/2007 | Genereux et al. |
| 2007/0197858 A1 | 8/2007 | Goldfarb et al. |
| 2007/0198038 A1 | 8/2007 | Cohen et al. |
| 2007/0203503 A1 | 8/2007 | Salahieh et al. |
| 2007/0203575 A1 | 8/2007 | Forster et al. |
| 2007/0213813 A1 | 9/2007 | VonSegesser et al. |
| 2007/0219612 A1 | 9/2007 | Andreas |
| 2007/0239254 A1 | 10/2007 | Chia |
| 2007/0244546 A1 | 10/2007 | Francis |
| 2007/0255390 A1 | 11/2007 | Ducke et al. |
| 2007/0265700 A1 | 11/2007 | Eliason et al. |
| 2007/0282414 A1 | 12/2007 | Soltis et al. |
| 2008/0039743 A1 | 2/2008 | DeWayne et al. |
| 2008/0039953 A1 | 2/2008 | David et al. |
| 2008/0065011 A1 | 3/2008 | Marchand et al. |
| 2008/0065149 A1 | 3/2008 | Thielen et al. |
| 2008/0077144 A1 | 3/2008 | Crofford |
| 2008/0125853 A1 | 5/2008 | Bailey et al. |
| 2008/0140089 A1 | 6/2008 | Kogiso et al. |
| 2008/0147093 A1 | 6/2008 | Roskopf et al. |
| 2008/0147112 A1 | 6/2008 | Sheets et al. |
| 2008/0147182 A1 | 6/2008 | Righini et al. |
| 2008/0161902 A1 | 7/2008 | Poulsen |
| 2008/0161911 A1 | 7/2008 | Revuelta et al. |
| 2008/0167713 A1 | 7/2008 | Bolling |
| 2008/0177300 A1 | 7/2008 | Epperly et al. |
| 2008/0255427 A1 | 10/2008 | Satake et al. |
| 2008/0294230 A1 | 11/2008 | Parker |
| 2008/0294247 A1 | 11/2008 | Yang et al. |
| 2008/0319455 A1 | 12/2008 | Harris et al. |
| 2008/0319526 A1 | 12/2008 | Hill et al. |
| 2009/0012356 A1 | 1/2009 | Dann et al. |
| 2009/0069889 A1 | 3/2009 | Suri |
| 2009/0138079 A1 | 5/2009 | Tuval |
| 2009/0157175 A1 | 6/2009 | Benichou |
| 2009/0163769 A1 | 6/2009 | Robertson et al. |
| 2009/0163934 A1 | 6/2009 | Raschdorf et al. |
| 2009/0192585 A1 | 7/2009 | Bloom et al. |
| 2009/0228093 A1 | 9/2009 | Taylor et al. |
| 2009/0234428 A1 | 9/2009 | Snow et al. |
| 2009/0275902 A1 | 11/2009 | Heeps et al. |
| 2009/0276039 A1 | 11/2009 | Meretei |
| 2009/0276040 A1 | 11/2009 | Rowe et al. |
| 2009/0281619 A1 | 11/2009 | Le et al. |
| 2009/0287304 A1 | 11/2009 | Dahlgren et al. |
| 2009/0299456 A1 | 12/2009 | Malsheimer |
| 2009/0319037 A1 | 12/2009 | Rowe et al. |
| 2010/0022823 A1 | 1/2010 | Goldfarb et al. |
| 2010/0030318 A1 | 2/2010 | Berra |
| 2010/0036472 A1 | 2/2010 | Papp |
| 2010/0036473 A1 | 2/2010 | Roth |
| 2010/0049313 A1 | 2/2010 | Alon et al. |
| 2010/0076402 A1 | 3/2010 | Mazzone |
| 2010/0076541 A1 | 3/2010 | Kumoyama |
| 2010/0082089 A1 | 4/2010 | Quadri |
| 2010/0094317 A1 | 4/2010 | Goldfarb et al. |
| 2010/0094394 A1 | 4/2010 | Beach |
| 2010/0121425 A1 | 5/2010 | Shimada |
| 2010/0121434 A1 | 5/2010 | Paul et al. |
| 2010/0145431 A1 | 6/2010 | Wu |
| 2010/0161036 A1 | 6/2010 | Pintor |
| 2010/0019132 A1 | 7/2010 | Alkhatib |
| 2010/0174363 A1 | 7/2010 | Castro |
| 2010/0198347 A1 | 8/2010 | Zakay et al. |
| 2010/0274344 A1 | 10/2010 | Dusbabek |
| 2010/0324595 A1 | 12/2010 | Linder et al. |
| 2011/0015616 A1 | 1/2011 | Straubinger et al. |
| 2011/0015729 A1 | 1/2011 | Jimenez et al. |
| 2011/0040374 A1 | 2/2011 | Goetz et al. |
| 2011/0054596 A1 | 3/2011 | Taylor |
| 2011/0082538 A1 | 4/2011 | Dahlgren et al. |
| 2011/0137331 A1 | 6/2011 | Walsh et al. |
| 2011/0137410 A1 | 6/2011 | Hacohen |
| 2011/0160846 A1 | 6/2011 | Bishop |
| 2011/0245855 A1 | 10/2011 | Matsuoka et al. |
| 2011/0295281 A1 | 12/2011 | Mizumoto et al. |
| 2012/0071969 A1 | 3/2012 | Li et al. |
| 2012/0109160 A1 | 5/2012 | Martinez et al. |
| 2012/0116419 A1 | 5/2012 | Sigmon |
| 2012/0123529 A1 | 5/2012 | Levi et al. |
| 2012/0209318 A1 | 8/2012 | Qadeer |
| 2012/0239142 A1 | 9/2012 | Liu et al. |
| 2013/0030519 A1 | 1/2013 | Tran et al. |
| 2013/0066341 A1 | 3/2013 | Ketai et al. |
| 2013/0066342 A1 | 3/2013 | Dell et al. |
| 2013/0072945 A1 | 3/2013 | Terada |
| 2013/0073034 A1 | 3/2013 | Wilson |
| 2013/0190861 A1 | 7/2013 | Chau et al. |
| 2013/0268069 A1 | 10/2013 | Zakai et al. |
| 2013/0317598 A1 | 11/2013 | Rowe et al. |
| 2014/0046433 A1 | 2/2014 | Kovalsky |
| 2014/0058411 A1 | 2/2014 | Soutorine et al. |
| 2014/0067048 A1 | 3/2014 | Chau et al. |
| 2014/0067052 A1 | 3/2014 | Chau et al. |
| 2014/0135685 A1 | 5/2014 | Arundhati et al. |
| 2014/0243968 A1 | 8/2014 | Saimuralidhar |
| 2014/0296962 A1 | 10/2014 | Cartledge et al. |

(56) References Cited

U.S. PATENT DOCUMENTS

| | | |
|---|---|---|
| 2014/0316428 A1 | 10/2014 | Golan |
| 2015/0039084 A1 | 2/2015 | Tamir et al. |
| 2015/0057704 A1 | 2/2015 | Takahashi |
| 2015/0105808 A1 | 4/2015 | Gordon et al. |
| 2015/0157268 A1 | 6/2015 | Winshtein et al. |
| 2015/0157455 A1 | 6/2015 | Hoang et al. |
| 2015/0196390 A1 | 7/2015 | Ma et al. |
| 2015/0223793 A1 | 8/2015 | Goldfarb et al. |
| 2015/0238313 A1 | 8/2015 | Spence et al. |
| 2015/0257883 A1 | 9/2015 | Basude et al. |
| 2015/0313592 A1 | 11/2015 | Coillard-Lavirotte et al. |
| 2016/0022970 A1 | 1/2016 | Forcucci et al. |
| 2016/0106539 A1 | 4/2016 | Buchbinder et al. |
| 2016/0113764 A1 | 4/2016 | Sheahan et al. |
| 2016/0113766 A1 | 4/2016 | Ganesan et al. |
| 2016/0155987 A1 | 6/2016 | Yoo et al. |
| 2016/0174979 A1 | 6/2016 | Wei |
| 2016/0174981 A1 | 6/2016 | Fago et al. |
| 2016/0242906 A1 | 8/2016 | Moriss et al. |
| 2016/0287387 A1 | 10/2016 | Wei |
| 2016/0317290 A1 | 11/2016 | Chau et al. |
| 2016/0331523 A1 | 11/2016 | Chau et al. |
| 2016/0354082 A1 | 12/2016 | Mehmet et al. |
| 2017/0020521 A1 | 1/2017 | Krone et al. |
| 2017/0035566 A1 | 2/2017 | Krone et al. |
| 2017/0042456 A1 | 2/2017 | Budiman |
| 2017/0049455 A1 | 2/2017 | Seguin |
| 2017/0056149 A1 | 3/2017 | Rajpara et al. |
| 2017/0065415 A1 | 3/2017 | Rupp et al. |
| 2017/0100236 A1 | 4/2017 | Robertson et al. |
| 2017/0128197 A1 | 5/2017 | Bialas et al. |
| 2017/0156839 A1 | 6/2017 | Cooper et al. |
| 2017/0156859 A1 | 6/2017 | Chang et al. |
| 2017/0231765 A1 | 8/2017 | Desrosiers et al. |
| 2017/0239048 A1 | 8/2017 | Goldfarb et al. |
| 2017/0035561 A1 | 9/2017 | Rowe et al. |
| 2017/0258584 A1 | 9/2017 | Chang et al. |
| 2017/0281330 A1 | 10/2017 | Liljegren et al. |
| 2017/0348102 A1 | 12/2017 | Cousins et al. |
| 2018/0008311 A1 | 1/2018 | Shiroff et al. |
| 2018/0021044 A1 | 1/2018 | Miller et al. |
| 2018/0021134 A1 | 1/2018 | McNiven et al. |
| 2018/0078271 A1 | 3/2018 | Thrasher |
| 2018/0126124 A1 | 5/2018 | Winston et al. |
| 2018/0146964 A1 | 5/2018 | Garcia |
| 2018/0146966 A1 | 5/2018 | Hernandez et al. |
| 2018/0153552 A1 | 6/2018 | Knig et al. |
| 2018/0153689 A1 | 6/2018 | Marmon et al. |
| 2018/0161159 A1 | 6/2018 | Benjamin et al. |
| 2018/0221147 A1 | 8/2018 | Ganesan et al. |
| 2018/0235657 A1 | 8/2018 | Chad |
| 2018/0243086 A1 | 8/2018 | Bararino et al. |
| 2018/0258665 A1 | 9/2018 | Padira et al. |
| 2018/0263767 A1 | 9/2018 | Chau et al. |
| 2018/0296326 A1 | 10/2018 | Dixon et al. |
| 2018/0296327 A1 | 10/2018 | Dixon et al. |
| 2018/0296328 A1 | 10/2018 | Dixon et al. |
| 2018/0296329 A1 | 10/2018 | Dixon et al. |
| 2018/0296330 A1 | 10/2018 | Dixon et al. |
| 2018/0296331 A1 | 10/2018 | Dixon et al. |
| 2018/0296332 A1 | 10/2018 | Dixon et al. |
| 2018/0296333 A1 | 10/2018 | Dixon et al. |
| 2018/0296334 A1 | 10/2018 | Dixon et al. |
| 2018/0325671 A1 | 11/2018 | Abunassar et al. |
| 2018/0344456 A1 | 12/2018 | Barash et al. |
| 2019/0000613 A1 | 1/2019 | Delgado et al. |
| 2019/0000623 A1 | 1/2019 | Pan et al. |
| 2019/0008642 A1 | 1/2019 | Delgado et al. |
| 2019/0008643 A1 | 1/2019 | Delgado et al. |
| 2019/0015199 A1 | 1/2019 | Delgado et al. |
| 2019/0015200 A1 | 1/2019 | Delgado et al. |
| 2019/0015207 A1 | 1/2019 | Delgado et al. |
| 2019/0015208 A1 | 1/2019 | Delgado et al. |
| 2019/0021851 A1 | 1/2019 | Delgado et al. |
| 2019/0021852 A1 | 1/2019 | Delgado et al. |
| 2019/0029810 A1 | 1/2019 | Delgado et al. |
| 2019/0029813 A1 | 1/2019 | Delgado et al. |
| 2019/0030285 A1 | 1/2019 | Santosh et al. |
| 2019/0060058 A1 | 2/2019 | Delgado et al. |
| 2019/0060059 A1 | 2/2019 | Delgado et al. |
| 2019/0060072 A1 | 2/2019 | Zeng |
| 2019/0060073 A1 | 2/2019 | Delgado et al. |
| 2019/0060074 A1 | 2/2019 | Delgado et al. |
| 2019/0060075 A1 | 2/2019 | Delgado et al. |
| 2019/0069991 A1 | 3/2019 | Metchik et al. |
| 2019/0069992 A1 | 3/2019 | Delgado et al. |
| 2019/0069993 A1 | 3/2019 | Delgado et al. |
| 2019/0167197 A1 | 6/2019 | Abunassar et al. |
| 2019/0261995 A1 | 8/2019 | Goldfarb et al. |
| 2019/0261996 A1 | 8/2019 | Goldfarb et al. |
| 2019/0261997 A1 | 8/2019 | Goldfarb et al. |
| 2019/0321597 A1 | 10/2019 | VanHouven |

FOREIGN PATENT DOCUMENTS

| | | |
|---|---|---|
| DE | 19907646 | 8/2000 |
| EP | 098100 | 1/1984 |
| EP | 592410 | 4/1994 |
| EP | 850607 | 7/1998 |
| EP | 1806114 | 7/2007 |
| EP | 2247263 | 8/2011 |
| EP | 3398560 | 11/2018 |
| FR | 2146050 | 2/1973 |
| FR | 2815844 | 5/2002 |
| JP | 2007516055 | 6/2007 |
| JP | 2007181702 | 7/2007 |
| WO | 91/17720 | 11/1991 |
| WO | 1998/029057 | 7/1998 |
| WO | 1999/012483 | 3/1999 |
| WO | 01/49213 | 7/2001 |
| WO | 01/54625 | 8/2001 |
| WO | 01/054625 | 8/2001 |
| WO | 01/76510 | 10/2001 |
| WO | 02/22054 | 3/2002 |
| WO | 02/36048 | 5/2002 |
| WO | 02/047575 | 6/2002 |
| WO | 2002/060352 | 8/2002 |
| WO | 2003/030776 | 4/2003 |
| WO | 03/047468 | 6/2003 |
| WO | 2004/019825 | 3/2004 |
| WO | 05/084595 | 9/2005 |
| WO | 2005/102015 | 11/2005 |
| WO | 2006/032051 | 3/2006 |
| WO | 2006/111391 | 10/2006 |
| WO | 2006/138173 | 12/2006 |
| WO | 2007/047488 | 4/2007 |
| WO | 2007/067942 | 6/2007 |
| WO | 07/112029 | 10/2007 |
| WO | 08/028569 | 3/2008 |
| WO | 2010/121076 | 10/2010 |
| WO | 2017/015632 | 1/2017 |
| WO | 2018/195015 | 10/2018 |
| WO | 2018/195201 | 10/2018 |
| WO | 2018/195215 | 10/2018 |
| WO | 2019/139904 | 7/2019 |

OTHER PUBLICATIONS

Al-Khaja et al., "Eleven Years' Experience with Carpentier—Edwards Biological Valves in Relation to Survival and Complications", European Journal of Cardio-thoracic Surgery 3: pp. 305-311, 1989.

Almagor et al., "Balloon Expandable Stent Implantation in Stenotic Right Heart Valved Conduits", Journal of the American College of Cardiology, vol. 16, No. 5, pp. 1310-1314, Nov. 15, 1990.

Andersen, et al., "Transluminal implantation of artificial heart valves. Description of a new expandable aortic valve and initial results with implantation by catheter technique in closed chest pigs." European Heart Journal (1992), 13, 704-708.

Andersen, H.R. "History of Percutaneous Aortic Valve Prosthesis," Herz No. 34. pp. 343-346. 2009.

(56) References Cited

OTHER PUBLICATIONS

Batista RJ et al., "Partial left ventriculectomy to treat end-stage heart disease", Ann Thorac Surg., vol. 64, Issue-3, pp. 634-638, Sep. 1997.
Beall AC Jr. et al.,"Clinical experience with a dacron velour-covered teflon-disc mitral-valve prosthesis", Ann Thorac Surg., vol. 5, Issue 5, pp. 402-410, May 1968.
Benchimol et al., "Simultaneous Left Ventricular Echocardiography and Aortic Blood Velocity During Rapid Right Ventricular Pacing in Man", The American Journal of the Medical Sciences, vol. 273, No. 1, pp. 55-62, 1977.
Dake et al., "Transluminal Placement of Endovascular Stent-Grafts for the Treatment of Descending Thoracic Aortic Aneurysms", The New England Journal of Medicine, vol. 331, No. 26, pp. 1729-1734, Dec. 29, 1994.
Dotter et al., "Transluminal Treatment of Arteriosclerotic Obstruction: Description of a New Technic and a Preliminary Report of Its Application", Circulation, vol. XXX, pp. 654-670, 1964.
Fucci et al., "Improved results with mitral valve repair using new surgical techniques", Eur J Cardiothorac Surg. 1995;Issue 9, vol. 11, pp. 621-626.
Inoune, M.D., Kanji, et al., "Clinical Application of Transvenous Mitral Commissurotomy by a New Balloon Catheter," The Journal of Thoracic and Cardiovascular Surgery 87:394-402, 1984.
Kolata, Gina "Device that Opens Clogged Arteries Gets a Failing Grade in a New Study", The New York Times, http://www.nytimes.com/1991/01/03/health/device-that-opens-clogged-arteries-gets-a-faili . . . , pp. 1-2, wrriten Jan. 3, 199, web page access Jul. 29, 2009.
Lawrence, Jr., et al., "Percutaneous Endovascular Graft: Experimental Evaluation", Cardiovascular Radiology 163, pp. 357-360, May 1987.
Maisano F et al., 'The edge-to-edge technique: a simplified method to correct mitral insufficiency, Eur J Cardiothorac Surg., vol. 13, Issue-3, pp. 240-245, Mar. 1998.
Pavcnik, M.D., Ph.D., Dusan, et al., "Development and Initial Experimental Evaluation of a Prosthetic Aortic Valve for Transcatheter Placement," Cardiovascular Radiology 1992; 183:151-154.
Porstmann et al., "Der Verschluß des Ductus Arteriosus Persistens Ohne Thorakotomie", Thoraxchirurgie Vaskuläre Chirurgie, Band 15, Heft 2, Stuttgart, im Apr. 1967, pp. 199-203.
Rashkind et al., "Creation of an Atrial Septal Defect Without Thoracotomy: A Pallative Approach to Complete Transposition of the Great Arteries", The Journal of the American Medical Association, vol. 196, No. 11, pp. 173-174, Jun. 13, 1956.
Rashkind et al., "Historical Aspects of Interventional Cardiology: Past, Present, and Future", Texas Heart Institute Journal, Interventional Cardiology, pp. 363-367.
Reul RM et al., "Mitral valve reconstruction for mitral insufficiency", Prog Cardiovasc Dis., vol. 39, Issue-6, May-Jun. 1997.
Rosch, M.D., Josef, "The Birth, Early Years and Future of Interventional Radiology," J Vasc Interv Radiol 2003; 14:841-853.
Ross, D.N, "Aortic Valve Surgery", Surgery of the Aortic Valves, Guy's Hospital, London, pp. 192-197.
Sabbah et al., "Mechanical Factors in the Degeneration of Porcine Bioprosthetic Valves: An Overview", Journal of Cardiac Surgery, vol. 4, No. 4, pp. 302-309, Dec. 1989.
Selby et al., "Experience with New Retrieval Forceps for Foreign Body Removal in the Vascular, Urinary, and Biliary Systems", Radiology: 176. pp. 535-538, 1990.
Serruys et al., "Stenting of Coronary Arteries. Are we the Sorcerer's Apprentice?", European Heart Journal, 10, 774-782, pp. 37-45, 1989.
Sigwart, Ulrich, "An Overview of Intravascular Stents: Old and New," Chapter 48, Textbook of Interventional Cardiology, 2nd Edition, W.B. Saunders Company, Philadelphia, PA, © 1994, 1990, pp. 803-815.
Uchida et al., "Modifications of Gianturco Expandable Wire Stents", Technical Note, American Roentgen Ray Society, pp. 1185-1187, May 1988.
Umaña JP et al., Bow-tie 'mitral valve repair: an adjuvant technique for ischemic mitral regurgitation', Ann Thorac Surg., vol. 66, Issue-6, pp. 1640-1646, Nov. 1998.
Urban, Philip MD, "Coronary Artery Stenting", Editions Medecine et Hygiene, Geneve, pp. 1-47, 1991.
Watt et al., "Intravenous Adenosine in the Treatment of Supraventricular Tachycardia: A Dose-Ranging Study and Interaction with Dipyridamole", Br. J. Clin. Pharmac. 21, pp. 227-230, 1986.
Wheatley, David J., "Valve Prosthesis", Rob & Smith's Operative Surgery, pp. 415-424, 1986.
Praz et A., "Compassionate use of the PASCAL transcatheter mitral valve repair system for patients with severe mitral regurgitation: a multicentre, prospective, observational, first-in-man study," Lancet vol. 390, pp. 773-780, 2017.

\* cited by examiner

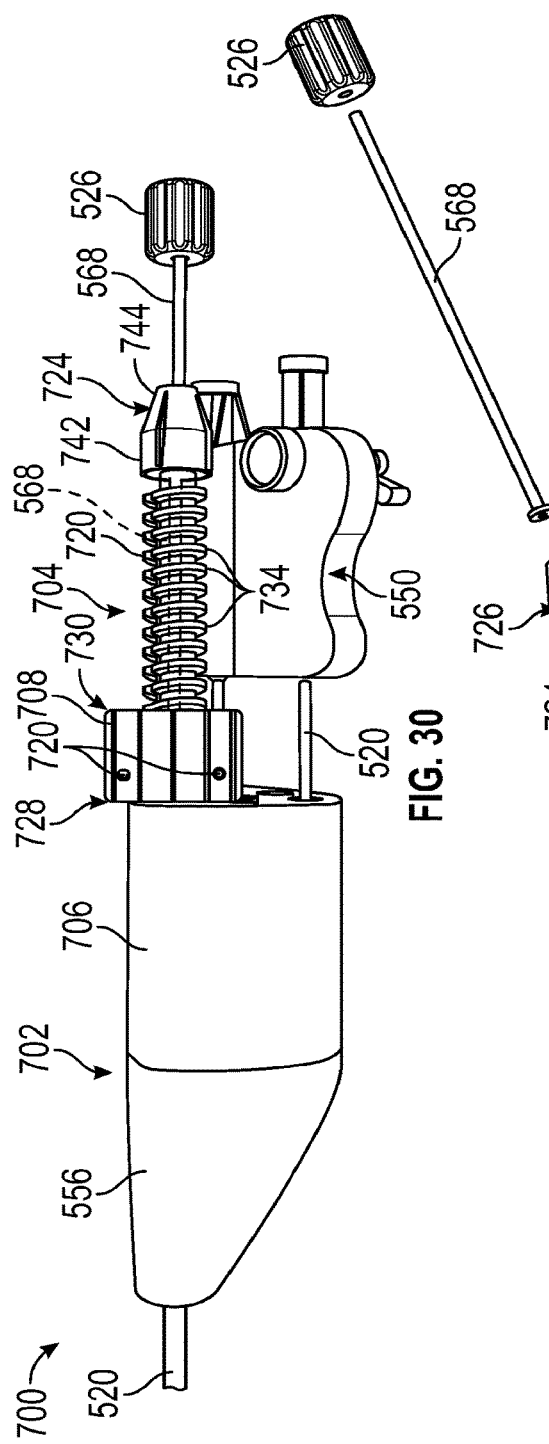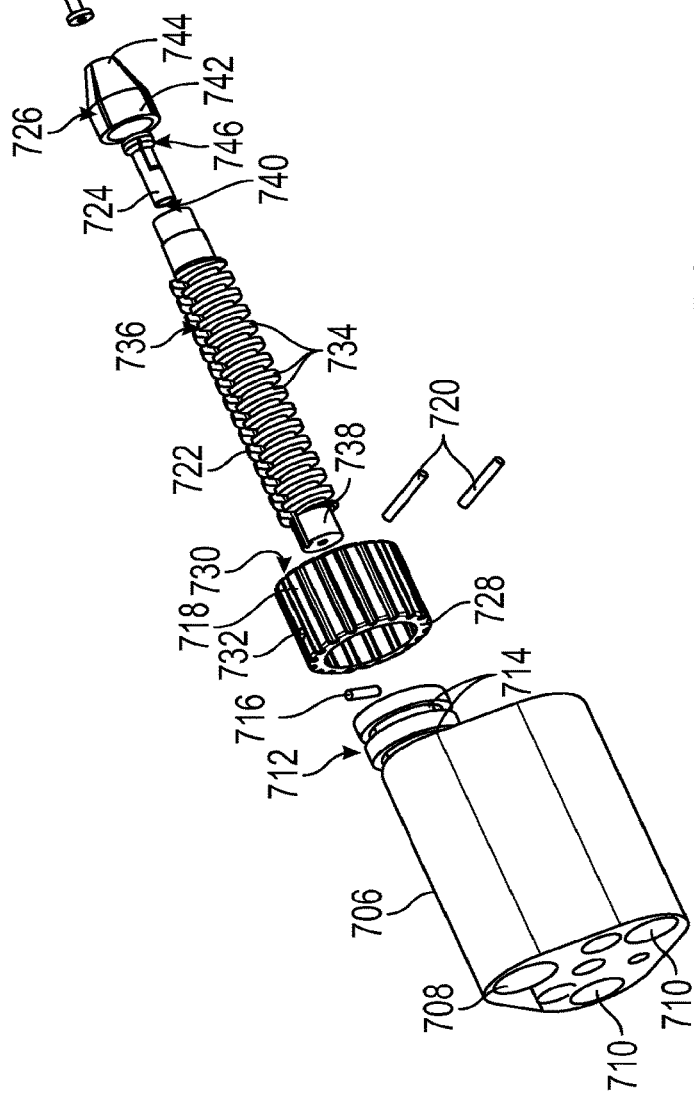
FIG. 30
FIG. 31

MITRAL VALVE SPACER DEVICE

CROSS-REFERENCE TO RELATED APPLICATIONS

This application is a continuation of U.S. patent application Ser. No. 15/973,892, filed on May 8, 2018, which claims the benefit of U.S. Provisional Application Nos. 62/659,253, filed Apr. 18, 2018, 62/571,552, filed Oct. 12, 2017, and 62/504,389, filed May 10, 2017, which applications are incorporated by reference herein.

FIELD

This disclosure generally relates to prosthetic devices and related methods for helping to seal native heart valves to prevent or reduce regurgitation therethrough, as well as devices and related methods for implanting such prosthetic devices.

BACKGROUND

The native heart valves (i.e., the aortic, pulmonary, tricuspid and mitral valves) serve critical functions in assuring the forward flow of an adequate supply of blood through the cardiovascular system. These heart valves can be damaged, and thus rendered less effective, by congenital malformations, inflammatory processes, infectious conditions, or disease. Such damage to the valves can result in serious cardiovascular compromise or death. For many years, the definitive treatment for such damaged valves was surgical repair or replacement of the valve during open heart surgery. However, open heart surgeries are highly invasive and are prone to many complications. Therefore, elderly and frail patients with defective heart valves often went untreated. More recently, transvascular techniques have been developed for introducing and implanting prosthetic devices in a manner that is much less invasive than open heart surgery. One particular transvascular technique that is used for accessing the native mitral and aortic valves is the transseptal technique. The transseptal technique comprises inserting a catheter into the right femoral vein, up the inferior vena cava and into the right atrium. The septum is then punctured and the catheter passed into the left atrium. Such transvascular techniques have increased in popularity due to their high success rates.

A healthy heart has a generally conical shape that tapers to a lower apex. The heart is four-chambered and comprises the left atrium, right atrium, left ventricle, and right ventricle. The left and right sides of the heart are separated by a wall generally referred to as the septum. The native mitral valve of the human heart connects the left atrium to the left ventricle. The mitral valve has a very different anatomy than other native heart valves. The mitral valve includes an annulus portion, which is an annular portion of the native valve tissue surrounding the mitral valve orifice, and a pair of cusps, or leaflets, extending downward from the annulus into the left ventricle. The mitral valve annulus can form a "D"-shaped, oval, or otherwise out-of-round cross-sectional shape having major and minor axes. The anterior leaflet can be larger than the posterior leaflet, forming a generally "C"-shaped boundary between the abutting free edges of the leaflets when they are closed together.

When operating properly, the anterior leaflet and the posterior leaflet function together as a one-way valve to allow blood to flow only from the left atrium to the left ventricle. The left atrium receives oxygenated blood from the pulmonary veins. When the muscles of the left atrium contract and the left ventricle dilates (also referred to as "ventricular diastole" or "diastole"), the oxygenated blood that is collected in the left atrium flows into the left ventricle. When the muscles of the left atrium relax and the muscles of the left ventricle contract (also referred to as "ventricular systole" or "systole"), the increased blood pressure in the left ventricle urges the two leaflets together, thereby closing the one-way mitral valve so that blood cannot flow back to the left atrium and is instead expelled out of the left ventricle through the aortic valve. To prevent the two leaflets from prolapsing under pressure and folding back through the mitral annulus toward the left atrium, a plurality of fibrous cords called chordae tendineae tether the leaflets to papillary muscles in the left ventricle.

Mitral regurgitation occurs when the native mitral valve fails to close properly and blood flows into the left atrium from the left ventricle during the systolic phase of heart contraction. Mitral regurgitation is the most common form of valvular heart disease. Mitral regurgitation has different causes, such as leaflet prolapse, dysfunctional papillary muscles and/or stretching of the mitral valve annulus resulting from dilation of the left ventricle. Mitral regurgitation at a central portion of the leaflets can be referred to as central jet mitral regurgitation and mitral regurgitation nearer to one commissure (i.e., location where the leaflets meet) of the leaflets can be referred to as eccentric jet mitral regurgitation.

Some prior techniques for treating mitral regurgitation include stitching portions of the native mitral valve leaflets directly to one another (known as an "Alfieri" stitch). Other prior techniques include the use of a leaflet clip, such as the MitraClip®, that is clipped onto the coaptation edges of the native mitral valve leaflets and hold them together to mimic an Alfieri stitch. Unfortunately, the MitraClip® device suffers from a number of drawbacks. For example, securing the leaflets directly to each other can place undue stress on the leaflets, which can cause tearing and single leaflet detachment. Also, the MitraClip® device has a relatively narrow profile and can only capture a very small area of the leaflets, which can create areas of the stress on the leaflets and possible trauma to the leaflets. Fastening the leaflets directly to each other also prevents the captured portions of the coaptation edges from separating during ventricular diastole, which can inhibit antegrade blood flow through the mitral valve.

Moreover, the procedure for implanting the MitraClip® device is relatively difficult and time consuming for a number of reasons. For example, it is difficult to properly position the device so that the clipping members are behind the native leaflets, which are moving during the cardiac cycle. Further, when positioning or retrieving the MitraClip® device the clipping members can become entangled or catch onto adjacent tissue, such as the chordae tendineae. Removing the device from the entangled tissue can be difficult and can cause trauma to the tissue. Another drawback is that a single MitraClip® device typically will not adequately reduce mitral regurgitation because only a very small area of the leaflets are held together. As such, multiple devices, such as two to four devices, typically are required to adequately address the regurgitation, which further adds to the complexity and time of the procedure.

Furthermore, it is difficult to manipulate the distal end portion of the MitraClip® delivery system within the small confines of the left atrium. For example, the MitraClip® delivery system does not permit independent positioning of the implant in the anterior-posterior directions, superior-inferior directions, and the medial-lateral directions. Due to limitations of the MitraClip® delivery system, adjustment of the delivery system in the medial-lateral direction, for example, will change the superior-inferior positioning of the implant. Thus, positioning the implant at the desired location along the coaptation edge using the MitraClip® delivery system is difficult and/or time consuming.

Accordingly, there is a continuing need for improved devices and methods for treating mitral valve regurgitation.

SUMMARY

Described herein are embodiments of prosthetic devices that are primarily intended to be implanted at one of the mitral, aortic, tricuspid, or pulmonary valve regions of a human heart, as well as apparatuses and methods for implanting the same. The prosthetic devices can be used to help restore and/or replace the functionality of a defective native valve.

An implantable prosthetic device can include a spacer member, a plurality of anchors, and a plurality of clasps. The spacer member can be configured to be disposed between native leaflets of a heart. The anchors can be coupled to the spacer member and configured to secure the native leaflets against the spacer member. The clasps can be coupled to a respective anchor and configured to secure the native leaflets to the anchors. The clasps can be independently movable between an open configuration and a closed configuration.

In one representative embodiment, an implantable prosthetic device comprises a spacer member, a plurality of anchors, and a plurality of clasps. The spacer member is configured to be disposed between native leaflets of a heart. The anchors are coupled to the spacer member and configured to secure the native leaflets against the spacer member. The clasps are coupled to a respective anchor and are configured to secure the native leaflets to the anchors. The clasps are independently movable between an open configuration and a closed configuration.

In some embodiments, the prosthetic device is movable between a compressed configuration, in which the spacer member is radially compressed and is axially spaced relative to at least a portion of the anchors, and an expanded configuration, in which the spacer member expands radially outwardly relative to the compressed configuration and overlaps the at least a portion of the anchors.

In some embodiments, the anchors are pivotable relative to the spacer member between a first configuration and a second configuration. An angle between the first portions of the anchors and the spacer member is greater than approximately 120 degrees when the anchors are in the first configuration.

In some embodiments, the anchors have first portions, second portions, and joint portions disposed between the first portions and the second portions. The first portions are coupled to the spacer member.

In some embodiments, the at least a portion of the anchors is the second portions of the anchors.

In some embodiments, the first portions are spaced relative to the second portions in the compressed configuration and overlap with the second portions in the expanded configuration.

In some embodiments, the anchors are pivotable relative to the spacer member between a first configuration and a second configuration. An angle between the first portions of the anchors and the spacer member is approximately 180 degrees when the anchors are in the first configuration, and the angle between the first portions of the anchors and the spacer member is approximately 0 degrees when the anchors are in the second configuration.

In some embodiments, the clasps comprise attachment portions and arm portions, the attachment portions are coupled to the anchors, and the arm portions are pivotable relative to the attachment portions between the open configuration and the closed configuration.

In some embodiments, the clasps are configured to capture the native leaflets between the attachment portions and the arm portions.

In some embodiments, the clasps are configured to be biased to the closed configuration.

In some embodiments, the clasps are configured to have a preload when the clasps are in the closed configuration.

In some embodiments, the clasps comprise barbs configured to engage tissue of the native leaflets.

In some embodiments, the spacer member and the anchors are formed from a single, unitary piece of material.

In some embodiments, the spacer member and the anchors includes braided or woven material comprising nitinol.

In some embodiments, the prosthetic device is configured for implantation in a native mitral valve and to reduce mitral regurgitation.

In another representative embodiment, an implantable prosthetic device comprises a spacer member, a plurality of anchors, and a plurality of clasps. The spacer member is configured to be disposed between native leaflets of a heart. The anchors are coupled to the spacer member and configured to secure the native leaflets against the spacer member. The anchors are pivotable relative to the spacer body between a first configuration and a second configuration. An angle between at least a portion of the anchors and the spacer member is approximately 180 degrees when the anchors are in the first configuration, and the angle between the at least a portion of the anchors and the spacer member is approximately 0 degrees when the anchors are in the second configuration. The clasps are coupled to a respective anchor and are configured to secure the native leaflets to the anchors. The clasps are movable between an open configuration and a closed configuration.

In some embodiments, the anchors have first portions, second portions, and joint portions disposed between the first portions and the second portions. The first portions are coupled to the spacer member. The at least a portion of the anchors is the first portions of the anchors.

In some embodiments, the clasps are separately movable between an open configuration and a closed configuration.

In another representative embodiment, an assembly comprises an implantable prosthetic device and a delivery apparatus. The implantable prosthetic device has a spacer member, a plurality of anchors, a plurality of clasps, a first collar, and a second collar. The first end portions of the anchors are coupled to a first end portion of the spacer member, and second end portions of the anchors are coupled to the first collar. The second collar is coupled to a second end portion of the spacer member, and the clasps are coupled to the anchors. The delivery apparatus has a first shaft, a second shaft, and a plurality of clasp control members. The first shaft is releasably coupled to the first collar of the prosthetic device, the second shaft is releasably coupled to the second collar of the prosthetic device, and the clasp control members are releasably coupled to the clasps of the prosthetic device. Actuating the clasp control members moves the clasps between an open configuration and a closed configuration.

In some embodiments, the delivery apparatus is configured such that moving the first shaft and the second shaft relative to each other moves the prosthetic device between a first configuration, in which anchors are in a radially compressed, axially elongate configuration, and a second configuration, in which the anchors are in a radially expanded, axially compressed configuration and at least partially overlap the spacer member to capture native leaflets between the anchors and the spacer member.

In some embodiments, the delivery apparatus further comprises a clasp control mechanism, and the clasp control members are releasably coupled to the clasp control mechanism. The clasp control mechanism is configured such that the clasp control members can be actuated either simultaneously or separately.

In some embodiments, the clasp control members comprise a first clasp control member and a second clasp control member. The clasp control mechanism comprises a first side portion, a second side portion, and a removable pin selectively coupling the first and second side portions. The first clasp control member is releasably coupled to first side portion of the clasp control mechanism, and the second clasp control member is releasably coupled to the second side portion of the clasp control mechanism.

In some embodiments, the delivery apparatus further comprises a locking mechanism coupled to the first shaft and the second shaft and configured to selectively prevent relative axial movement between the first shaft and the second shaft.

In some embodiments, the locking mechanism comprises a rotatable knob.

In some embodiments, the locking mechanism is configured to be selectively movable from a lock configuration to a release configuration. The locking mechanism prevents relative axial movement between the first shaft and the second shaft in the lock configuration, and the locking mechanism allows relative axial movement between the first shaft and the second shaft in the release configuration.

In some embodiments, the locking mechanism comprises a knob, a drive screw, and a guide pin. The knob is rotatably coupled to the second shaft and the drive screw, the drive screw is coupled to the first shaft, and the guide pin is coupled to the second shaft and configured to prevent relative rotational movement between the knob and the drive screw. Rotating the knob relative to the second shaft and the drive screw results in relative axial movement between the first shaft and the second shaft.

In some embodiments, the first shaft and the first collar are threadably coupled.

In some embodiments, the first collar comprises a lumen. The first shaft comprises a radially expandable member dispose at the distal end portion of the first shaft. The expandable member is configured such that the expandable member can be inserted through the lumen of the first collar when the expandable member is a compressed state and such that the expandable member cannot be withdrawn through the lumen of the first collar when the expandable member is inserted through the lumen of the first collar and the expandable member is an expanded state.

In another representative embodiment, an implantable prosthetic device comprises a spacer member, a plurality of anchors, and a plurality of clasps. The spacer member is configured to be disposed between native leaflets of a heart. The anchors are coupled to the spacer member and configured to secure the native leaflets against the spacer member. The clasps are configured to secure the native leaflets to the anchors and have fixed end portions and free end portions. The fixed end portions are coupled to the anchors. The free end portions have barbs. The free end portions are pivotable relative to the fixed end portions between an open configuration and a closed configuration. The free end portions are axially movable in the open configuration from a first position in which the barbs engage tissue of the native leaflets to a second position in which the barbs disengage the tissue of the native leaflets.

In another representative embodiment, an implantable prosthetic device comprises a spacer member, a plurality of anchors, and a plurality of clasps. The spacer member is configured to be disposed between native mitral valve leaflets of a heart. The anchors are coupled to the spacer member. The anchors are configured to secure the native mitral valve leaflets against the spacer member during ventricular systole and to allow the native mitral valve leaflet to move away from the spacer member during ventricular diastole. The clasps are coupled to a respective anchor and configured to secure the native leaflets to the anchors. The clasps are movable between an open configuration and a closed configuration.

In yet another representative embodiment, an implantable prosthetic device comprises a spacer member, a sleeve, a plurality of anchors, and a piston. The spacer member is configured to be disposed between native leaflets of a heart. The sleeve is coupled to and disposed radially within the spacer member. The anchors are configured to secure the native leaflets against the spacer member and having first end portions and second end portions. The first end portions are coupled to the spacer member. The anchors are movable between an elongate configuration and a foreshortened configuration. The piston is coupled to the second end portions of the anchors. The piston is axially movable relative to the cylinder between a first configuration and a second configuration. The anchors are in the elongate configuration when the piston is in the first configuration. The anchors are in the foreshortened configuration when the piston is in the second configuration.

In another representative embodiment, an assembly comprises the prosthetic device of the previous paragraph and a delivery apparatus. The delivery apparatus comprises an outer shaft, an actuation shaft, and a plurality of tethers. The outer shaft has a first lumen and a plurality of second lumens disposed radially outwardly from the first lumen. The actuation shaft extends through the first lumen. The actuation shaft is axially movable relative the outer shaft and releasably coupled to the piston of the prosthetic device. The tethers extend through the second lumens and are releasably coupled to the prosthetic device. Tensioning the tethers moves the implantable prosthetic device and the outer shaft toward each other. Slackening the tethers allows the implantable prosthetic device and the outer shaft to be space from each other.

In some embodiments, each of the tethers is disposed in two of the second lumens that are circumferentially offset by approximately 180 degrees.

In some embodiments, the prosthetic device further comprises a plurality of clasps. The clasps are coupled to a respective anchor and are configured to secure the native leaflets to the anchors. The clasps are movable between an open configuration and a closed configuration. The outer shaft of the delivery apparatus further comprises a plurality of third lumens disposed radially outwardly from the first lumen. The delivery apparatus further comprises a plurality of control members extending through the third lumens and releasably coupled to the clasps of the prosthetic device. Tensioning the control members move the clasps to the open configuration. Slackening the control members allows the clasps to move to the closed configuration.

In some embodiments, each of the control members is disposed in two of the third lumens that are circumferentially offset by approximately 180 degrees.

In some embodiments, each of the second lumens is circumferentially offset relative to an adjacent second lumen by approximately 90 degrees. Each of the third lumens is circumferentially offset relative to an adjacent third lumen by approximately 90 degrees. Each of the second lumens is circumferentially offset relative to an adjacent third lumen by approximately 45 degrees.

In another representative embodiment, an assembly comprises an implantable prosthetic device and a delivery apparatus. The implantable prosthetic device has a spacer member, a plurality of anchors, a plurality of clasps, a first collar, and a second collar. The first end portions of the anchors are coupled to a first end portion of the spacer member, and second end portions of the anchors are coupled to the first collar. The second collar is coupled to a second end portion of the spacer member, and the clasps are coupled to the anchors and are independently movable between an open configuration and a closed configuration. The delivery apparatus has a first shaft, a second shaft, a plurality of tethers, and a plurality of clasp control members. The first shaft is releasably coupled to the first collar of the prosthetic device by the tethers, the second shaft is releasably coupled to the second collar of the prosthetic device, and the clasp control members are releasably coupled to the clasps of the prosthetic device. Actuating the clasp control members moves the clasps between an open configuration and a closed configuration. Tensioning the tethers moves the prosthetic device and the first shaft toward each other, and slackening the tethers allows the prosthetic device and the first shaft to be spaced from each other.

In another representative embodiment, a handle for a delivery apparatus comprises a main body and an anchor actuation mechanism coupled to the main body. The anchor actuation mechanism is configured to be coupled to anchors of a prosthetic spacer device and to move the anchors of the prosthetic spacer device between a closed configuration and an open configuration. The anchor actuation mechanism includes a knob and a mode selector button configured to move the anchors actuation mechanism between a first mode of operation and a second mode of operation. When the anchor actuation mechanism is in the first mode of operation, the knob is rotatable relative to the main body, and rotation of the knob moves the anchors of the prosthetic spacer device between the closed configuration and the open configuration. When the anchor actuation mechanism is in the second mode of operation, the knob is axially slidable relative to the main body, and axially sliding the knob moves the anchors of the prosthetic spacer device between the closed configuration and the open configuration.

In some embodiments, the handle further comprises a clasp actuation mechanism coupled to the main body. The clasp actuation mechanism is configured to be coupled to claps of the prosthetic spacer device and configured to move the clasps of the prosthetic spacer device between a closed configuration and an open configuration.

In one representative embodiment, a positioning tool for a delivery apparatus comprises a main body and one or more projections. The main body is configured to be releasably coupled to a first portion of a handle of the delivery apparatus. The projections extend from the main body and are configured to releasably engage a second portion of the handle of the delivery apparatus. The positioning tool prevents relative movement between the first and second portions of the handle of the delivery apparatus when the positioning tool is coupled thereto.

The various innovations of this disclosure can be used in combination or separately. This summary is provided to introduce a selection of concepts in a simplified form that are further described below in the detailed description. This summary is not intended to identify key features or essential features of the claimed subject matter, nor is it intended to be used to limit the scope of the claimed subject matter. The foregoing and other objects, features, and advantages of the disclosure will become more apparent from the following detailed description, which proceeds with reference to the accompanying figures.

BRIEF DESCRIPTION OF THE DRAWINGS

FIG. 30 illustrates another exemplary embodiment of a handle for the delivery apparatus of FIG. 11.

FIG. 31 is an exploded view of the handle of FIG. 30.

FIGS. 73-75 also illustrate an exemplary embodiment of a clasp positioning tool.

DETAILED DESCRIPTION

General Considerations

Figure 1:
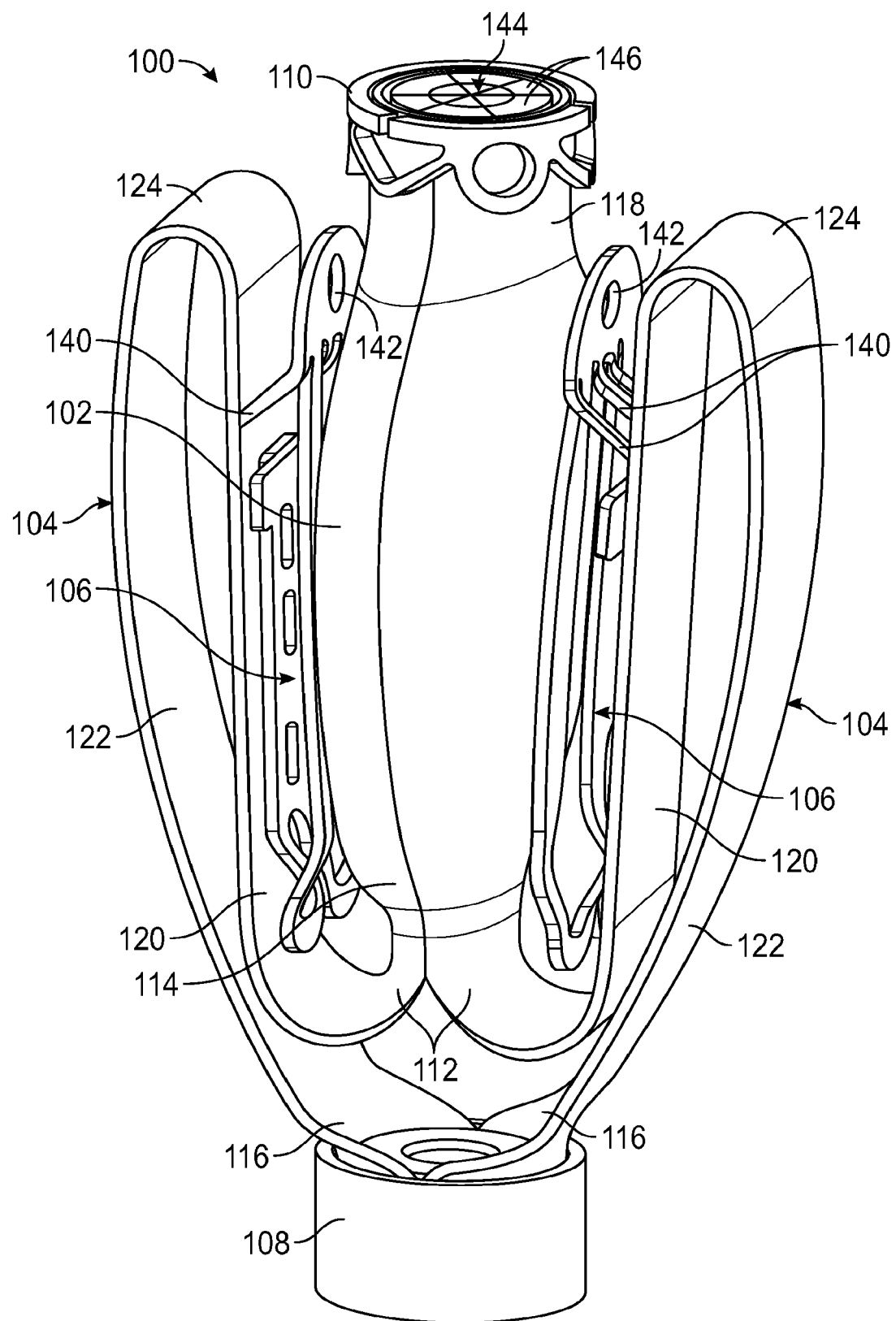
FIG. 1 illustrates an exemplary embodiment of a prosthetic spacer device, showing a first configuration.

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

As used in this application and in the claims, the singular forms "a," "an," and "the" include the plural forms unless the context clearly dictates otherwise. Additionally, the term "includes" means "comprises." Further, the term "coupled" generally means physically, mechanically, chemically, magnetically, and/or electrically coupled or linked and does not exclude the presence of intermediate elements between the coupled or associated items absent specific contrary language.

As used herein, the term "proximal" refers to a position, direction, or portion of a device that is closer to the user and further away from the implantation site. As used herein, the term "distal" refers to a position, direction, or portion of a device that is further away from the user and closer to the implantation site. Thus, for example, proximal motion of a device is motion of the device away from the implantation site and toward the user (e.g., out of the patient's body), while distal motion of the device is motion of the device away from the user and toward the implantation site (e.g., into the patient's body). The terms "longitudinal" and "axial" refer to an axis extending in the proximal and distal directions, unless otherwise expressly defined.

As used herein, the term "approximately" means the listed value and any value that is within 10% of the listed value. For example, "approximately 100 degrees" means any value between 90-110 degrees, inclusive.

Exemplary Embodiments

Described herein are embodiments of prosthetic spacer devices that are primarily intended to be implanted at one of the mitral, aortic, tricuspid, or pulmonary valve regions of a human heart, as well as apparatuses and methods for implanting the same. The prosthetic spacer devices can be used to help restore and/or replace the functionality of a defective native valve.

A prosthetic spacer device comprises a spacer member and at least one anchor. In certain embodiments, the prosthetic spacer device further comprises at least one clasp and at least one collar.

The spacer member can be configured to be positioned within the native valve orifice to fill a space between improperly functioning native leaflets that do not naturally coapt completely. As such, the spacer member helps create a more effective seal between the native leaflets and prevents or minimizes regurgitation (e.g., mitral regurgitation). The spacer member can comprise a structure that is impervious to blood and that allows the native leaflets to close around the sides of the spacer member to block retrograde blood flow (e.g., blood flowing from the left ventricle back into the left atrium during ventricular systole).

The spacer member can have various shapes. In some embodiments, the spacer member can have an elongated cylindrical shape having a round cross-sectional shape. In other embodiments, the spacer member can have an ovular cross-sectional shape, a crescent cross-sectional shape, or various other non-cylindrical shapes.

Configuring a prosthetic spacer device with a spacer member can, for example, reduce the need to implant multiple prosthetic spacers devices in a patient to reduce regurgitation compared to devices that clip the native leaflets directly to each other.

In certain embodiments configured for implantation in a native mitral valve, the spacer member can have an atrial or upper end positioned in or adjacent to the left atrium of the heart, a ventricular or lower end positioned in or adjacent to the left ventricle of the heart, and an annular side surface that extends between the native mitral leaflets.

The anchor can be configured to secure the prosthetic spacer device to one or more of the native leaflets such that the spacer member is positioned between the native leaflets. The anchor can be configured to be positioned behind a native leaflet when implanted such that the native leaflet is captured between the anchor and the spacer member.

In some embodiments, a first end portion of the anchor can be attached to a lower end portion of the spacer member, and a second end portion of the anchor can be attached to a first collar disposed below the lower end portion of the spacer member. In some embodiments, the prosthetic spacer device can comprise a second collar attach to an upper end portion of the spacer member.

The first and/or second collars can be configured to releasably connect the prosthetic spacer device to a delivery apparatus. In some embodiments, the first and second collars can be independently movable relative to each other.

In certain embodiments, a clasp is attached to the anchor. The clasp can be configured to capture and secure a native leaflet to the anchor. In some embodiments, the prosthetic spacer device comprises more than one clasp. In certain embodiments, the clasps are independently or separately actuatable relative to each other and/or the anchors.

Figure 2:
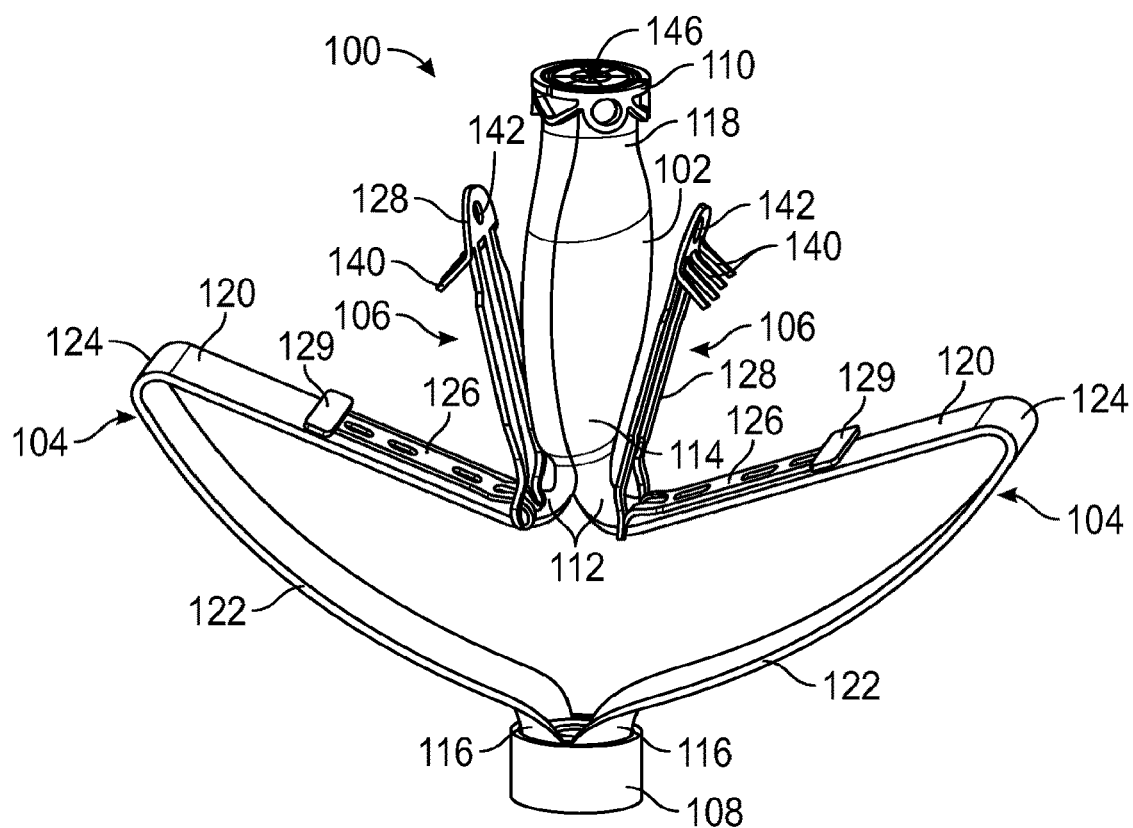
FIG. 2 is a perspective view of the prosthetic spacer device of FIG. 1, showing a second configuration.
Figure 3:
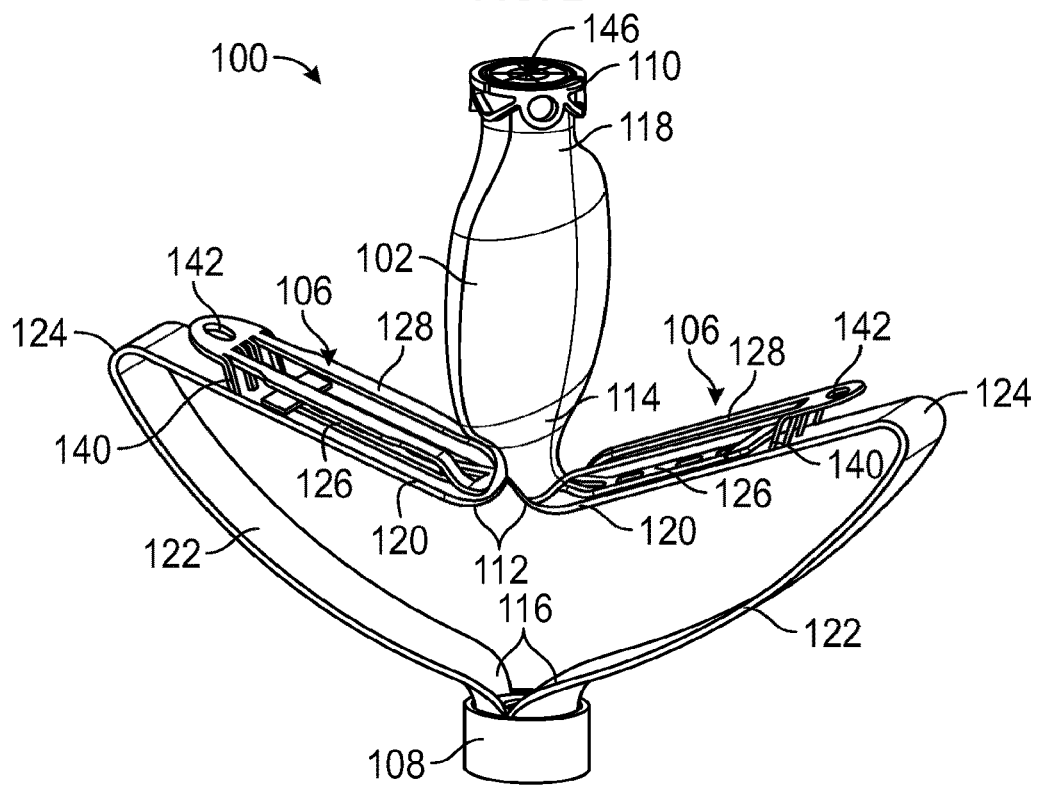
FIG. 3 is a perspective view of the prosthetic spacer device of FIG. 1, showing a third configuration.

FIGS. 1-5 show an exemplary embodiment of a prosthetic spacer device 100 and its components. Referring to FIG. 1, the prosthetic spacer device 100 can comprise a spacer member 102, a plurality of paddles or anchors 104 (e.g., two in the illustrated embodiment), a plurality of clasps 106 (e.g., two in the illustrated embodiment), a first collar 108, and a second collar 110. As best shown in FIG. 3, first end portions 112 of the anchors 104 can be coupled to and extend from a first end portion 114 of the spacer member 102, and second end portions 116 of the anchors 104 can be coupled to the first collar 108. The second collar 110 can be coupled to a second end portion 118 of the spacer member 102.

The spacer member 102 and the anchors 104 can be coupled together in various ways. For example, as shown in the illustrated embodiment, the spacer member 102 and the anchors 104 can be coupled together by integrally forming the spacer member 102 and the anchors 104 as a single, unitary component. This can be accomplished, for example, by forming the spacer member 102 and the anchors 104 from a braided or woven material, such as braided or woven nitinol wire. In other embodiments, the spacer member 102 and the anchors 104 can be coupled together by welding, fasteners, adhesive, and/or other means for coupling.

Referring to FIG. 2, the anchors 104 can comprise first portions 120 and second portions 122 separated by joint portions 124. In this manner, the anchors 104 are configured similar to legs in that the first portions 120 are like upper portions of the legs, the second portions 122 are like lower portions of the legs, and the joint portions 124 are like knee portions of the legs.

In some embodiments, the first and second portions 120, 122 can be separate components that are coupled together by the joint portions 124. For example, in one particular embodiment, the first and second portions 120, 122 can be plates or shafts that are coupled together by a cloth covering which acts, among other things, as the joint portions 124.

The anchors 104 can be configured to move between various configurations by axially moving the first collar 108 and thus the anchors 104 relative to the spacer member 102 along a longitudinal axis extending between the first and second end portions 114, 118 of the spacer member 102. For example, the anchors 104 can be positioned in a straight or substantially straight or unfolded configuration by moving the first collar 108 away from the spacer member 102 such that the anchors 104 are taut. In the straight configuration, the joint portions 124 of the anchors 104 are adjacent the longitudinal axis of the spacer member 102 (e.g., similar to the configuration shown in FIG. 20).

From the straight configuration, the anchors 104 can be moved to a fully folded configuration (e.g., FIG. 1) by moving the first collar 108 toward the spacer member 102. Initially as the first collar 108 moves toward the spacer member 102, the anchors 104 bend at the joint portions 124, and the joint portions 124 move radially outwardly relative to the longitudinal axis of the spacer member 102 and axially toward the first end portion 114 of the spacer member 102, as shown in FIGS. 2-3. As the first collar 108 continues to move toward the spacer member 102, the joint portions 124 move radially inwardly relative to the longitudinal axis of the spacer member 102 and axially toward the second end portion 118 of the spacer member 102, as shown in FIG. 1.

In some embodiments, an angle between the first portions 120 of the anchors 104 and the spacer member 102 can be approximately 180 degrees when the anchors 104 are in the straight configuration (see, e.g., FIG. 20), and the angle between the first portions 120 of the anchors 104 and the spacer member 102 can be approximately 0 degrees when the anchors 104 are in the fully folded configuration. The anchors 104 can be positioned in various partially folded configurations such that the angle between the first portions 120 of the anchors 104 and the spacer member 102 can be approximately 10-170 degrees or approximately 45-135 degrees.

Configuring the prosthetic spacer device 100 such that the anchors 104 can extend to a straight or approximately straight configuration (e.g. approximately 120-180 degrees relative to the spacer member 102) can provide several advantages. For example, this can reduce the radial crimp profile of the prosthetic spacer device 100. It can also make it easier to capture the native leaflets by providing a larger opening in which to capture the native leaflets. Additionally, the relatively narrow, straight configuration can prevent or reduce the likelihood that the prosthetic spacer device 100 will become entangled in native anatomy (e.g., chordae tendineae) when positioning and/or retrieving the prosthetic spacer device 100 into the delivery apparatus.

Referring again to FIG. 2, the clasps 106 can comprise attachment portions 126 and arm portions 128. The attachment portions 126 can be coupled to the first portions 120 of the anchors 104 in various ways such as with sutures, adhesive, fasteners (e.g., plates 129), welding and/or means for coupling.

The arm portions 128 can pivot relative to the attachment portions 126 between an open configuration (e.g., FIG. 2) and a closed configuration (FIGS. 1 and 3). In some embodiments, the clasps 106 can be biased to the closed configuration. In the open configuration, the attachment portions 126 and the arm portions 128 are pivoted away from each other such that native leaflets can be positioned between the attachment portions 126 and the arm portions 128. In the closed configuration, the attachment portions 126 and the arm portions 128 are pivoted toward each other, thereby clamping the native leaflets between the attachment portions 126 and the arm portions 128.

Figure 4:
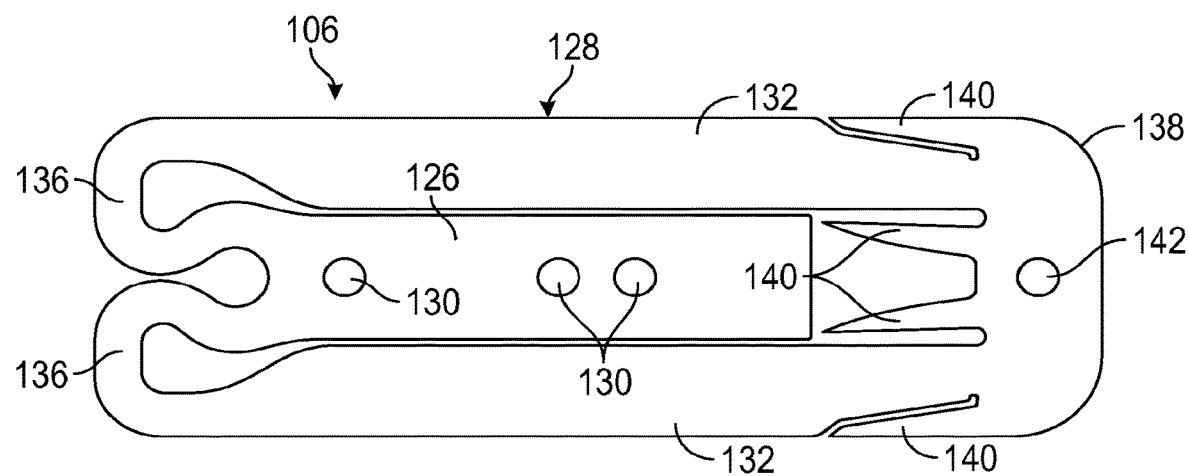
FIG. 4 is a plan view of a clasp of the prosthetic spacer device of FIG. 1, showing a first configuration.
Figure 5:
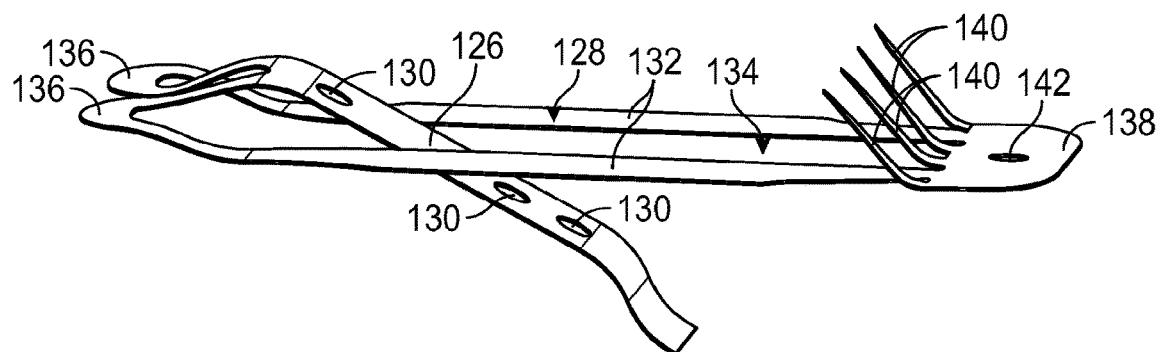
FIG. 5 is a perspective view of the clasp of the prosthetic spacer device of FIG. 1, showing a second configuration.

Referring to FIGS. 4-5, each attachment portion 126 (only one shown in FIGS. 4-5) can comprise one or more openings 130 (e.g., three in the illustrated embodiment). At least some of the openings 130 can be used to couple the attachment portions 126 to the anchors 104. For example, sutures and/or fasteners can extend through the openings 130 of the clasps 106 and through the anchors 104 to secure the attachment portions 126 to the anchors 104.

Each of the arm portions 128 can comprise two side beams 132 that are spaced apart from each other to form a slot 134. The slot 134 can be configured to receive the attachment portion 126. The arm portion 128 can also include a fixed end portion 136 that is coupled to the attachment portion 126 and a free end portion 138 disposed opposite the fixed end portion 136.

The free end portion 138 of each arm portion 128 can comprise gripper elements such as barbs 140 and/or other means for frictionally engaging native leaflet tissue. The gripper elements can be configured to engage and/or penetrate the native leaflet tissue to help retain the native leaflets between the attachment portions 126 and arm portions 128 of the clasps 106.

The free end portion 138 can also comprise an eyelet or opening 142, which can be used to couple the free end portion 138 to an actuation mechanism configured to pivot the arm portions 128 relative to the attachment portions 126. Additional details regarding coupling the clasps 106 to the actuation mechanism are provided below.

In some embodiments, the clasps 106 can be formed from a shape memory material such as nitinol, stainless steel, and/or shape memory polymers. In certain embodiments, the clasps 106 can be formed by laser-cutting a piece of flat sheet of material (e.g., nitinol) in the configuration shown in FIG. 4 and then shape-setting the clasp 106 in the configuration shown in FIG. 5.

Shape-setting the clasps 106 in this manner can provide several advantages. For example, the clasps 106 can be compressed from the shape-set configuration (e.g., FIG. 5) to the flat configuration (e.g., FIG. 4), which reduces the radial crimp profile of the clasps 106. Also, this also improves trackability and retrievability of the prosthetic spacer device 100 relative to a catheter shaft of a delivery apparatus because barbs 140 are pointing radially inwardly toward the anchors 104 when the prosthetic spacer device 100 is advanced through or retrieved into the catheter shaft (see, e.g., FIG. 20). This thus prevents or reduces the likelihood that the clasps 106 may snag or skive the catheter shaft.

In addition, shape-setting the clasps 106 in the configuration shown in FIG. 5 can increase the clamping force of the clasps 106 when the clasps 106 are in the closed configuration. This is because the arm portions 128 are shape-set relative to the attachment portions 126 to a first position (e.g., FIG. 5) which is beyond the position the arm portions 128 can achieve when the clasps 106 are attached to the anchors 104 (e.g., FIG. 3) because the anchors 104 prevent the arm portions 128 from further movement toward the shape-set configuration. This results in arm portions 128 having a preload (i.e., the clamping force is greater than zero) when the clasps 106 are attached to the anchors 104 and in the closed configuration. Thus, shape-setting the clasps 106 in the FIG. 5 configuration can increase the clamping force of the clasps 106 compared to clasps that are shape-set in the closed configuration. In this manner, the connection between the arm portion 128 and the attachment portion 126 functions as a spring hinge to bias the arm portion 128 to the closed configuration.

The magnitude of the preload of the clasps 106 can be altered by adjusting the angle in which the arm portions 128 are shape-set relative to the attachment portions 126. For example, increasing the relative angle between the arm portions 128 and the attachment portions 126 increases the preload, and decreasing the relative angle between the arm portions 128 and the attachment portions 126 decreases the preload. Other techniques and mechanisms can be used to bias the clasps 106 to the closed position, such as by coupling a spring (e.g., a torsion spring) or another type of biasing element between the arm portion 128 and the attachment portion 126. Still alternatively, the clasps 106 can be connected to corresponding anchors 104 without attachment portions 126 and biasing elements can be used to bias the clasps 106 to the closed configuration against the anchors.

In some embodiments, the second collar 110 and/or the spacer member 102 can comprise a hemostatic sealing member 144 configured to reduce or prevent blood from flowing through the second collar 110 and/or the spacer member 102. For example, in some embodiments, the sealing member 144 can comprise a plurality of flexible flaps 146, as shown in FIG. 1. The flaps 146 can be configured to pivot from a sealed configuration to an open configuration to allow a delivery apparatus to extend through the second collar 110. When the delivery apparatus is removed, the flaps 146 can be configured to return to the sealed configuration from the open configuration.

Figure 6:
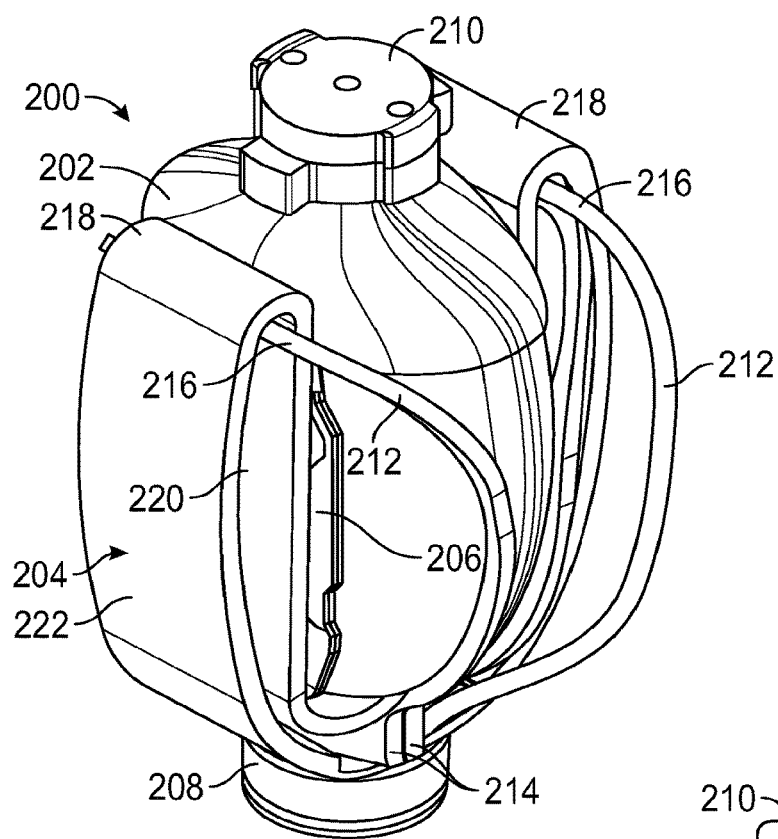
FIG. 6 illustrates another exemplary embodiment of a prosthetic spacer device.
Figure 7:
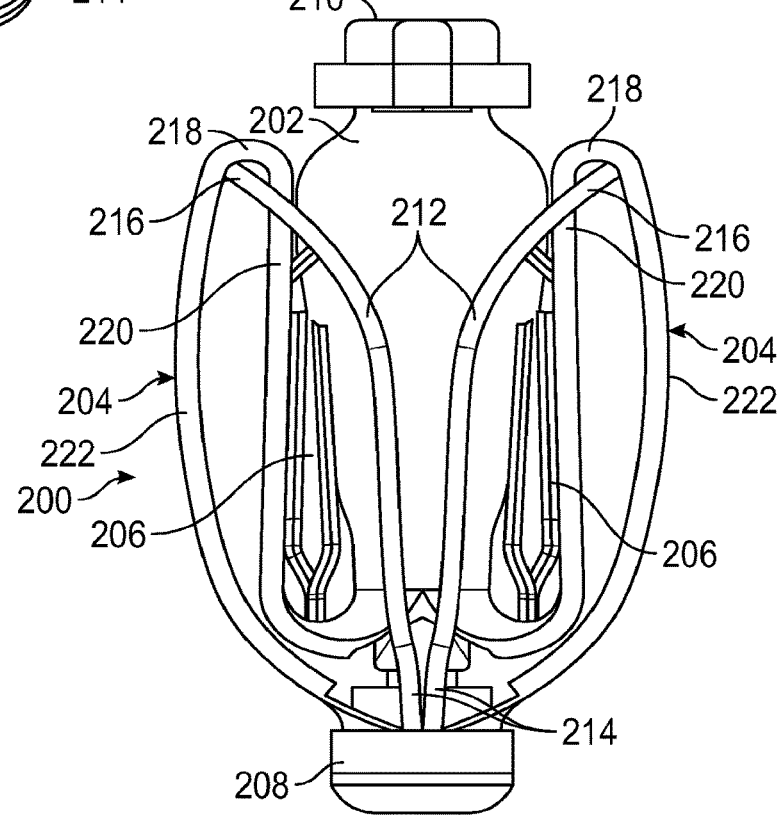
FIG. 7 is a side elevation view of the prosthetic spacer device of FIG. 6.
Figure 8:
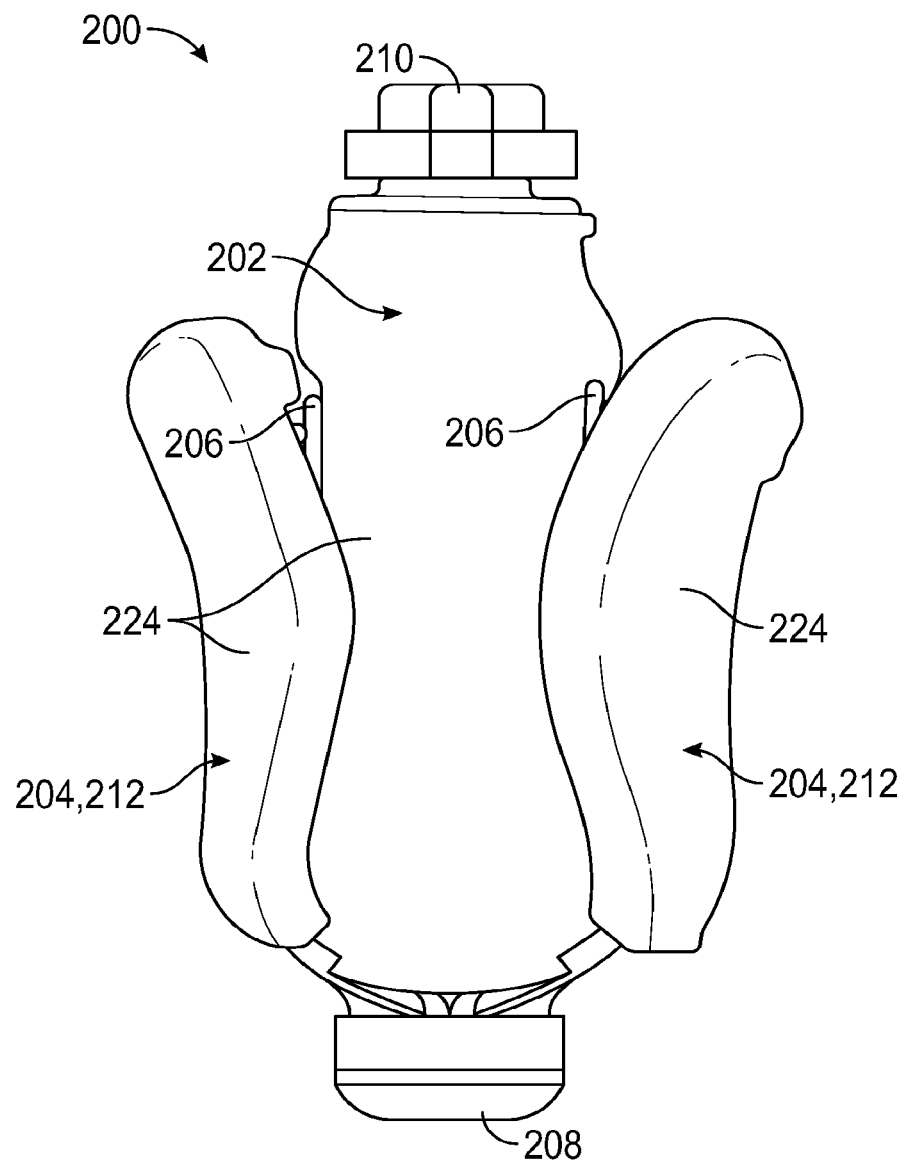
FIG. 8 is a side elevation view of the prosthetic spacer device of FIG. 7, showing a cover thereon.

FIGS. 6-8 show an exemplary embodiment of a prosthetic spacer device 200. The prosthetic spacer device 200 can comprise a spacer member 202, a plurality of anchors 204, a plurality of clasps 206, a first or distal collar 208, and a second or proximal collar 210. These components of the prosthetic spacer device 200 can be configured substantially similar to the corresponding components of the prosthetic spacer device 100.

The prosthetic spacer device 200 can also include a plurality of anchor extension members 212. Each of the anchor extension members 212 can be configured as a loop shaped structure having a first or fixed end portion 214 coupled to and extending from the distal collar 208 and second or free end portion 216 disposed opposite the fixed end portion 214. The anchor extension members 212 can be configured to extend circumferentially farther around the spacer member 202 than the anchors 204. For example, in some embodiments, each of the anchor extension members 212 can extend around approximately half the circumference of the spacer member 202 (as best shown in FIG. 7), and the anchors 204 can extend around less than half of circumference of the spacer member 202 (as best shown in FIG. 6). The anchor extension members 212 can also be configured to extend laterally (i.e., perpendicular to a longitudinal axis of the spacer member 202) beyond an outer diameter of the spacer member 202.

The anchor extension members 212 can further be configured such that free end portions 216 of the anchor extension members 212 are disposed axially adjacent a joint portion 218 of the anchors 204 and radially between first and second portions 220, 222 of the anchors 204 when the prosthetic spacer device 200 is in a folded configuration (e.g., FIGS. 6-8).

Configuring the anchor extension members 212 in this manner provides increased surface area compared to the anchors 204 alone. This can, for example, make it easier to capture and secure the native leaflets. The increased surface area can also distribute the clamping force of the anchors 204 and anchor extension members 212 against the native leaflets over a relatively larger surface of the native leaflets in order to further protect the native leaflet tissue.

The increased surface area of the anchor extension members 212 can also allow the native leaflets be to clamped to the prosthetic spacer device 200 such that the unclamped portions of the native leaflets coapt together at a location adjacent the prosthetic spacer device 200, as opposed to against the spacer member 202. This can, for example, improve sealing of the native leaflet and thus prevent or further reduce mitral regurgitation.

Referring to FIG. 8, the prosthetic spacer device 200 can also include a cover 224. In some embodiments, the cover 224 can be disposed on the spacer member 202, the anchors 204, and/or the anchor extension members 212. The cover 224 can be configured to prevent or reduce blood-flow through the prosthetic spacer device 200 and/or to promote native tissue ingrowth. In some embodiments, the cover 224 can be a cloth or fabric such PET, velour, or other suitable fabric. In other embodiments, in lieu of or in addition to a fabric, the cover 224 can include a coating (e.g., polymeric) that is applied to the prosthetic spacer device 200. It should be noted that the prosthetic spacer device 200 is shown without the cover 224 in FIGS. 6-7 and 12-13 and with the cover 224 in FIGS. 8, 11, and 20-27. In some embodiments, the cover 224 can have a porosity selected to allow blood to flow through the spacer member 202 for a predetermined length of time (e.g., one or more days, weeks, or months). Endothelialization of the spacer device over time can slowly and gradually reduce the amount of regurgitant blood flow through the spacer member, which can reduce the amount of stress on the left ventricle following implantation. Further details of a cover that permits regurgitant blood flow through the spacer member for a predetermined period of time are disclosed in U.S. Provisional Application No. 62/555,240, filed Sep. 7, 2017, which application is incorporated by reference herein.

Figure 9:
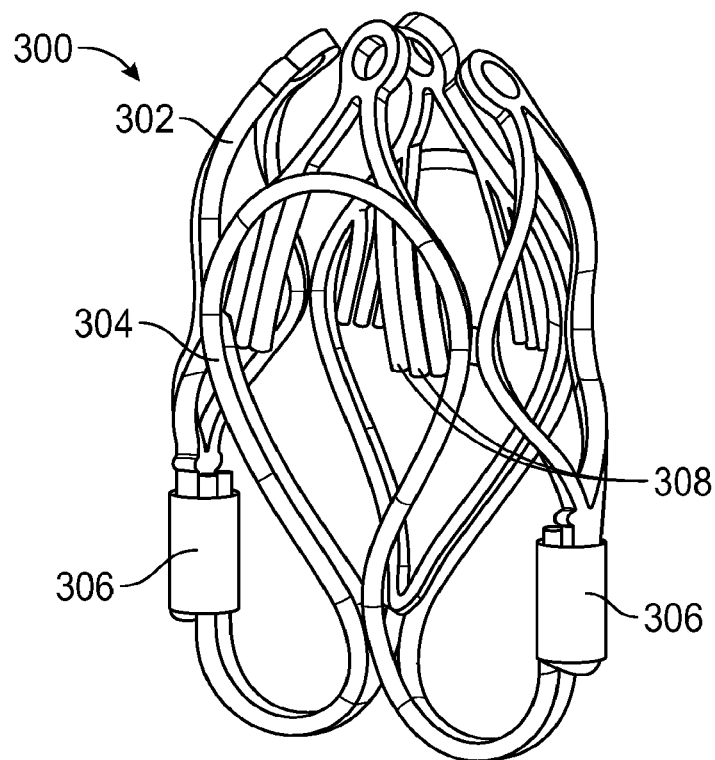
FIG. 9 illustrates another exemplary embodiment of a prosthetic spacer device.

FIG. 9 shows an exemplary embodiment of a prosthetic spacer device 300 comprising an annular spacer member 302, a fabric cover (not shown) covering the outer surface of the spacer member 302, and anchors 304 extending from the spacer member 302. The cover or additional covers may also extend over the anchors 304. The ends of each anchor 304 can be coupled to respective struts of the spacer member 302 by respective sleeves 306 that can be crimped around the end portions of the anchors 304 and the struts of the spacer member 302. Mounted on the frame of the spacer member 302 can be one or more barbs or projections 308. The free ends of the projections 308 can comprise various shapes including rounded, pointed, barbed, etc. The projections 308 can exert a retaining force against native leaflets by virtue of the anchors 304, which are shaped to force the native leaflets inwardly into the spacer member 302 in the area below the free ends of the anchors 304.

Figure 10:
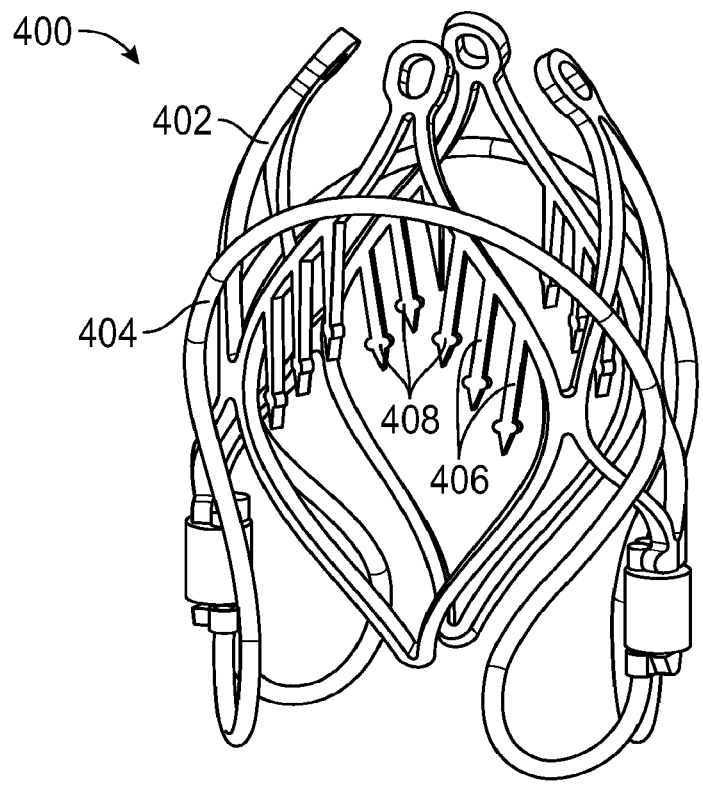
FIG. 10 illustrates another exemplary embodiment of a prosthetic spacer device.

FIG. 10 shows an exemplary embodiment of a prosthetic spacer device 400. The prosthetic spacer device 400 can comprise an annular spacer member 402, a fabric cover (not shown) covering the spacer member, and anchors 404 extending from the spacer member 402 and can be configured similar to the prosthetic spacer device 300. The cover may also cover the outer surfaces of the anchors.

The anchors 404 of the prosthetic spacer device 400 can be configured similar to the anchors 304 of the prosthetic spacer device 300 except that the curve at the free end of each anchor 404 is wider and has a larger radius than the anchors 304. As such, the anchors 404 cover a relatively larger portion of the spacer member 402 than the anchors 304. This can, for example, distribute the clamping force of the anchors 404 against the native leaflets over a relatively larger surface of the native leaflets in order to further protect the native leaflet tissue. It can also improve sealing because the native leaflets are clamped against the prosthetic spacer device 400 such that the native leaflets coapt together at a location adjacent the prosthetic spacer device 400, as opposed to against the spacer member 402.

Also, mounted on the frame of the spacer member 402 can be one or more barbs or projections 406. The free ends of the projections 406 can comprise stoppers 408 configured to limit the extent of the projections 406 that can engage and/or penetrate the native leaflets.

Additional details regarding the prosthetic spacer devices can be found, for example, in U.S. Patent Application Publication No. 2016/0331523 and U.S. Provisional Application No. 62/161,688, which applications are incorporated by reference herein.

A prosthetic spacer device (e.g., the devices 100, 200, 300, 400) can be coupled to a delivery apparatus to form a delivery assembly. The delivery apparatus can be used to percutaneously deliver, position, and/or secure the prosthetic spacer device within a patient's native heart valve region.

Figure 11:
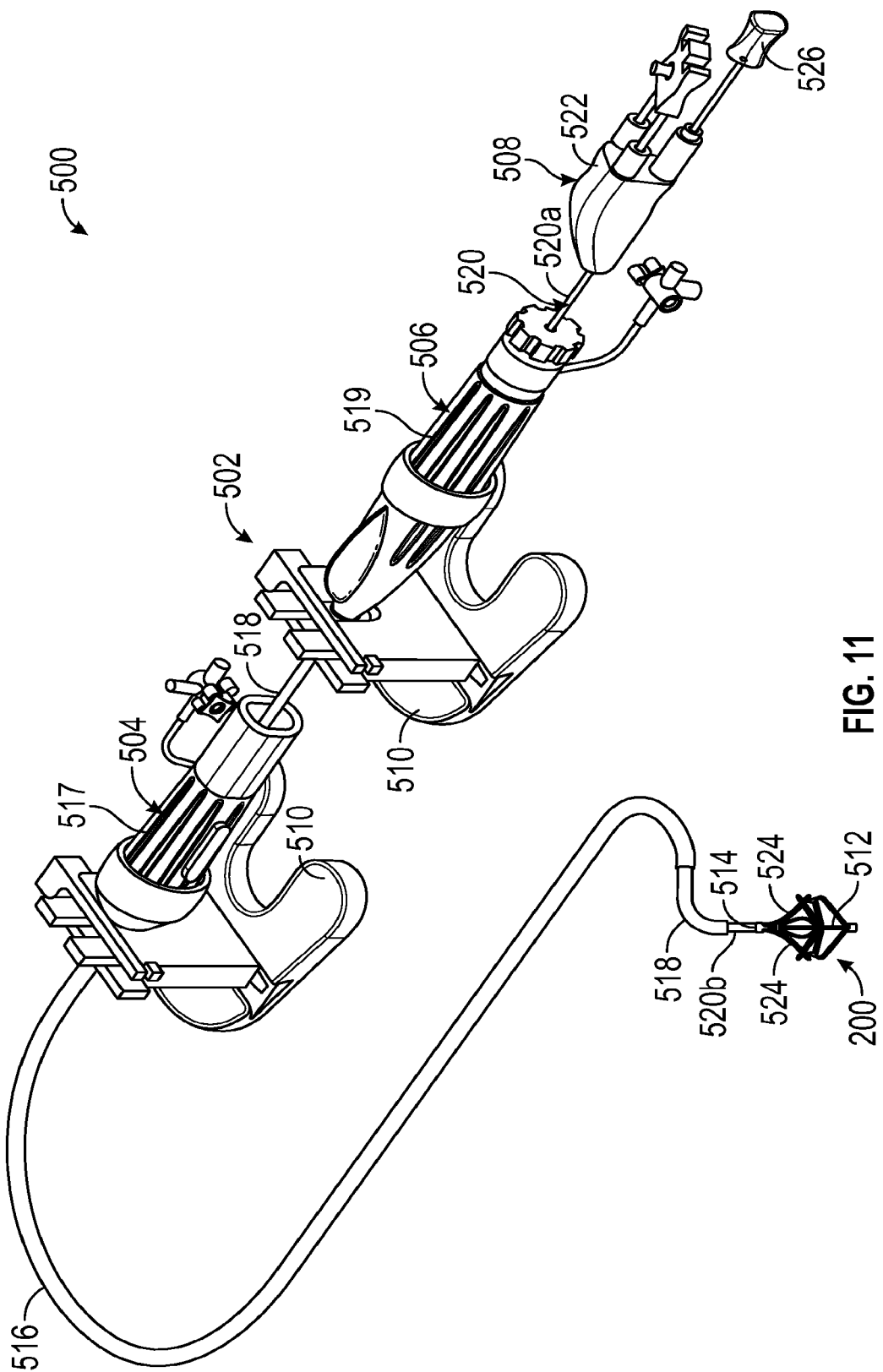
FIG. 11 illustrates an exemplary embodiment of a delivery assembly comprising the prosthetic spacer device of FIG. 6 (shown in partial cross-section) and a delivery apparatus.

FIG. 11-27 shows an exemplary delivery assembly 500 and its components. Referring to FIG. 11, the delivery assembly 500 can comprise the prosthetic spacer device 200 and a delivery apparatus 502. The delivery apparatus 502 can comprise a plurality of catheters and one or more catheter stabilizers. For example, in the illustrated embodiment, the delivery apparatus 502 includes a first catheter 504, a second catheter 506, a third catheter 508, and catheter stabilizers 510. The second catheter 506 extends coaxially through the first catheter 504, and the third catheter 508 extends coaxially through the first and second catheters 504, 506. The prosthetic spacer device 200 can be releasably coupled to a distal end portion of the third catheter 508 of the delivery apparatus 502, as further described below.

Each of the catheter stabilizers 510 can be used to hold a corresponding catheter stationary relative to the patient and other components of the delivery apparatus during a procedure. The stabilizers 510 can be positioned on a common table or support platform, which in turn can be placed on the operating table. For example, after manually inserting a catheter into the vasculature of a patient and positioning the distal end of the catheter at a desired location within the patient's body, the medical practitioner can then place the catheter in a corresponding stabilizer 510, freeing the practitioner's hands for manipulating another catheter during the procedure. Further details regarding the catheter stabilizers and a support platform for supporting the stabilizers are disclosed in U.S. Application No. 62/491,392, filed Apr. 28, 2017, which application is incorporated by reference herein.

In the illustrated embodiment, the delivery assembly 500 is configured, for example, for implanting the prosthetic spacer device 200 in a native mitral valve via a transseptal delivery approach. In other embodiments, the delivery assembly 500 can be configured for implanting the prosthetic spacer device 200 in aortic, tricuspid, or pulmonary valve regions of a human heart. Also, the delivery assembly 500 can be configured for various delivery methods, including transseptal, transaortic, transventricular, etc.

Figure 12:
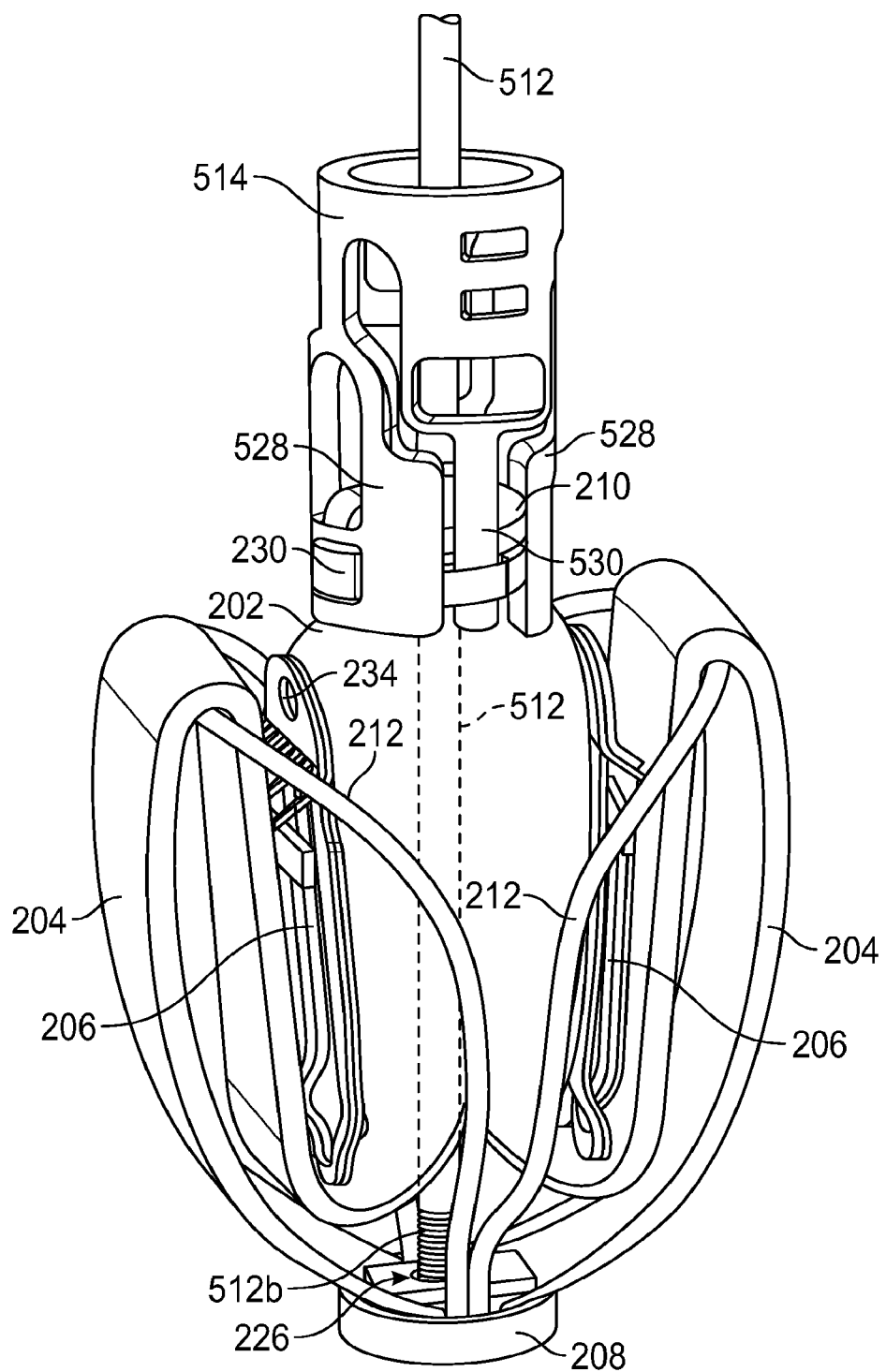
FIG. 12 is a perspective view of a distal end portion of the delivery assembly of FIG. 11, showing the prosthetic spacer device releasably coupled to the delivery apparatus.
Figure 13:
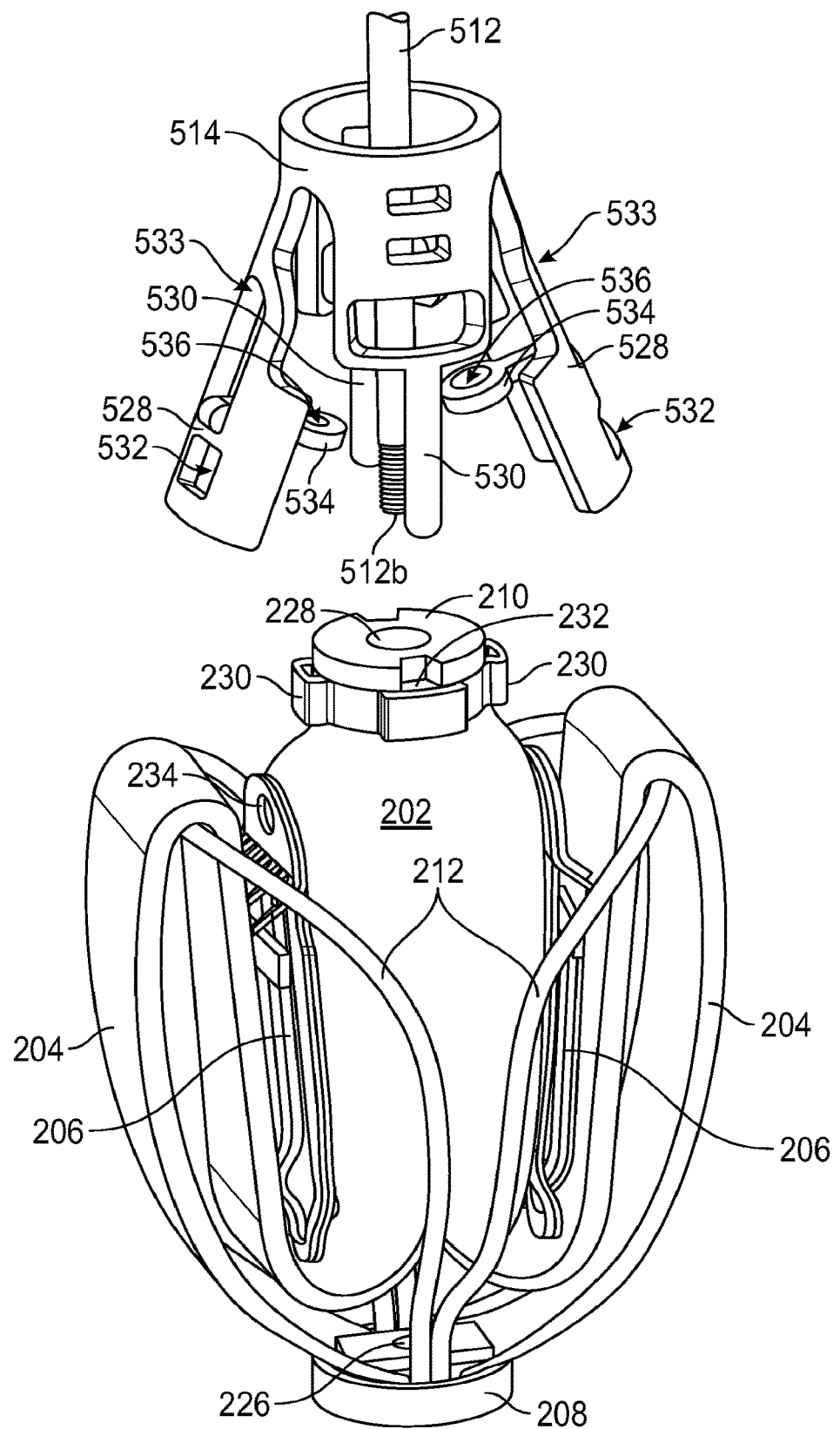
FIG. 13 is a perspective view of the distal end portion of the delivery assembly of FIG. 11, showing the prosthetic spacer device released from the delivery apparatus.

Referring to FIG. 13, the first or distal collar 208 of the prosthetic spacer device 200 can include a bore 226. In some embodiments, the bore 226 can comprise internal threads configured to releasably engage corresponding external threads of an actuation shaft 512 of the delivery apparatus 502, as best shown in FIG. 12.

Referring again to FIG. 13, the second or proximal collar 210 of the prosthetic spacer device 200 can include a central opening 228 that is axially aligned with the bore 226 of the distal collar 208. The central opening 228 of the proximal collar 210 can be configured to slidably receive the actuation shaft 512 of the delivery apparatus 502, as best shown in FIG. 12. In some embodiments, the proximal collar 210 and/or the spacer member 202 can have a sealing member (not shown, but see, e.g., the sealing member 144 shown in FIG. 1) configured to seal the central opening 228 when the actuation shaft 512 is withdrawn from the central opening 228.

As best shown in FIG. 13, the proximal collar 210 can also include a plurality of bosses or projections 230 and a plurality of guide openings 232 formed in the projections 230. The projections 230 can extending radially outwardly and can be circumferentially offset (e.g., by 90 degrees) relative to the guide openings 232. The guide openings 232 can be disposed radially outwardly from the central opening 228. The projections 230 and the guide openings 232 of the proximal collar 210 can be configured to releasably engage a coupler 514 of the delivery apparatus 502, as shown in FIG. 12.

Referring again to FIG. 11 and as mentioned above, the delivery apparatus 502 can include the first and second catheters 504, 506. The first and second catheters 504, 506 can be used, for example, to access an implantation location (e.g., a native mitral valve region of a heart) and/or to position the third catheter 508 at the implantation location.

The first and second catheters 504, 506 can comprise first and second sheaths or shafts 516, 518 extending from handles 517, 519, respectively. The first and second catheters 504, 506 can be configured such that the sheaths 516, 518 are steerable. For example, although not shown, the second catheter 506 can comprise one or more pull wires, and one or more flexible, axially non-compressible pull wire sleeves (e.g., helical coils). The pull wires and the sleeves can extend through a portion of the shaft 518, and the sleeves can move freely relative to the shaft 518), as further described in U.S. Patent Application Publication No. U.S. 2016/0158497, which application is incorporated by reference herein. This can, for example, allow a steerable distal end portion 518a of the shaft 518 to be deflected, moved, and/or rotated in one or more directions (e.g., in the medial/lateral and/or anterior/posterior directions to track the "C"-shape of the coaptation line between the native mitral valve leaflets between the posteromedial commissure and the anterolateral commissure), while also keeping a distal end portion of the implant catheter (e.g., the third catheter 508) and the thus the prosthetic spacer device coaxial relative to the mitral valve in one or more other directions (e.g., the inferior/superior directions).

Additional details regarding the first catheter 504 can be found, for example, in U.S. patent application Ser. No. 15/796,436, filed Oct. 27, 2017, which application is incorporated by reference herein. Additional details regarding the second catheter 506 can be found, for example, in U.S. Patent Application Publication No. U.S. 2016/0158497.

Referring still to FIG. 11, delivery apparatus 502 can also include the third catheter 508, as mentioned above. The third catheter 508 can be used, for example, to deliver, manipulate, position, and/or deploy the prosthetic spacer device 200 at the implantation location, as further described below.

Figure 15:
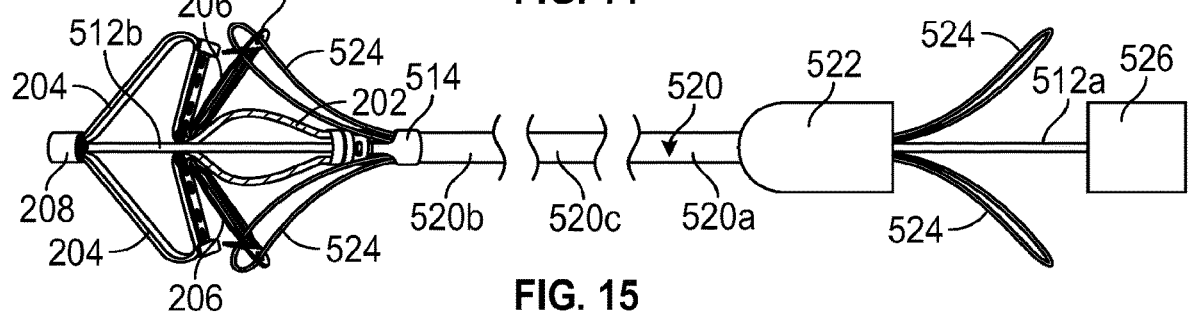
FIG. 15 is a perspective view of the delivery assembly of FIG. 11, with the prosthetic spacer device shown in partial cross-section and some components of the delivery apparatus shown schematically.

Referring to FIG. 15, the third catheter 508 can comprise the inner or actuation shaft 512, the coupler 514, an outer shaft 520, a handle 522 (shown schematically), and clasp control members 524. A proximal end portion 520a of the outer shaft 520 can be coupled to and extend distally from the handle 522, and a distal end portion 520b of the outer shaft 520 can be coupled to the coupler 514. A proximal end portion 512a of the actuation shaft 512 can coupled to an actuation knob 526. The actuation shaft 512 can extend distally from the knob 526 (shown schematically), through the handle 522, through the outer shaft 520, and through the coupler 514. The actuation shaft 512 can be moveable (e.g., axially and/or rotationally) relative to the outer shaft 520 and the handle 522. The clasp control members 524 can extend through and be axially movable relative to the handle 522 and the outer shaft 520. The clasp control members 524 can also be axially movable relative to the actuation shaft 512.

In some embodiments, the outer shaft 520 of the third catheter 508 can be configured to be steerable. For example, although not shown, the third catheter 508 can comprise a pull wire, and a flexible, axially non-compressible pull wire sleeve (e.g., a helical coil).

As best shown in FIGS. 12-13, the actuation shaft 512 of the third catheter 508 can be releasably coupled to the distal collar 208 of the prosthetic spacer device 200. For example, in some embodiments, the distal end portion 512b of the actuation shaft 512 can comprise external thread configured to releasably engage the interior threads of the bore 226 of the prosthetic spacer device 200. As such, rotating the actuation shaft 512 in a first direction (e.g., clockwise) relative to the distal collar 208 of the prosthetic spacer device 200 releasably secures the actuation shaft 512 to the distal collar 208. Rotating the actuation shaft 512 in a second direction (e.g., counterclockwise) relative to the distal collar 208 of the prosthetic spacer device 200 releases the actuation shaft 512 from the distal collar 208.

Figure 14:
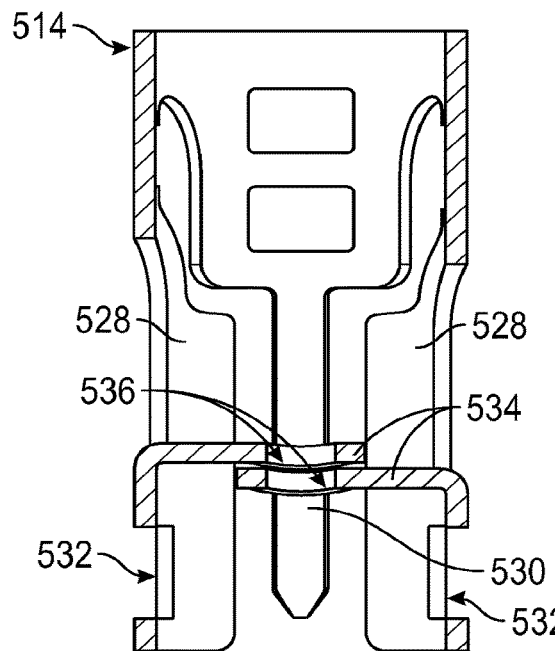
FIG. 14 is a cross-sectional view of a coupler of the delivery apparatus of FIG. 11.

Referring now to FIG. 12-14, the coupler 514 of the third catheter 508 can be releasably coupled to the proximal collar 210 of the prosthetic spacer device 200. For example, in some embodiments, the coupler 514 can comprise a plurality of flexible arms 528 and a plurality of stabilizer members 530. The flexible arms 528 can comprise apertures 532, ports 533 (FIG. 13), and eyelets 534 (FIG. 14).

The flexible arms 528 can be configured to pivot between a first or release configuration (FIG. 13) and a second or coupled configuration (FIGS. 12 and 14). In the first configuration, the flexible arms 528 extend radially outwardly relative to the stabilizer members 530. In the second configuration, the flexible arms 528 extend axially parallel to the stabilizer members 530 and the eyelets 534 radially overlap, as best shown in FIG. 14. The flexible arms 528 can be configured (e.g., shape-set) so as to be biased to the first configuration.

The prosthetic spacer device 200 can be releasably coupled to the coupler 514 by inserting the stabilizer members 530 of the coupler 514 into the guide openings 232 of the prosthetic spacer device 200. The flexible arms 528 of the coupler 514 can then be pivoted radially inwardly from the first configuration to the second configuration such that the projections 230 of the prosthetic spacer device 200 extend radially into the apertures 532 of the flexible arms 528. The flexible arms 528 can be retained in the second configuration by inserting the distal end portion 512b of the actuation shaft 512 through openings 536 of the eyelets 534, which prevents the flexible arms 528 from pivoting radially outwardly from the second configuration to the first configuration, thereby releasably coupling the prosthetic spacer device 200 to the coupler 514.

The prosthetic spacer device 200 can be released from the coupler 514 by proximally retracting the actuation shaft 512 relative to the coupler 514 such that the distal end portion 512b of the actuation shaft 512 withdraws from the openings 536 of the eyelets 534. This allows the flexible arms 528 to pivot radially outwardly from the second configuration to the first configuration, which withdraws the projections 230 of the prosthetic spacer device 200 from the apertures 532 of the flexible arms 528. The stabilizer members 530 can remain inserted into the guide openings 232 of the prosthetic spacer device 200 during and after the flexible arms 528 are released. This can, for example, prevent the prosthetic spacer device 200 from moving (e.g., shifting and/or rocking) while the flexible arms 528 are released. The stabilizer members 530 can then be withdrawn from the guide openings 232 of the prosthetic spacer device 200 by proximally retracting the coupler 514 relative to the prosthetic spacer device 200, thereby releasing the prosthetic spacer device 200 from the coupler 514.

Referring to FIG. 15, the outer shaft 520 of the third catheter 508 can be an elongate shaft extending axially between the proximal end portion 520a, which is coupled the handle 522, and the distal end portion 520b, which is coupled to the coupler 514. The outer shaft 520 can also include an intermediate portion 520c disposed between the proximal and distal end portions 520a, 520b.

Figure 16:
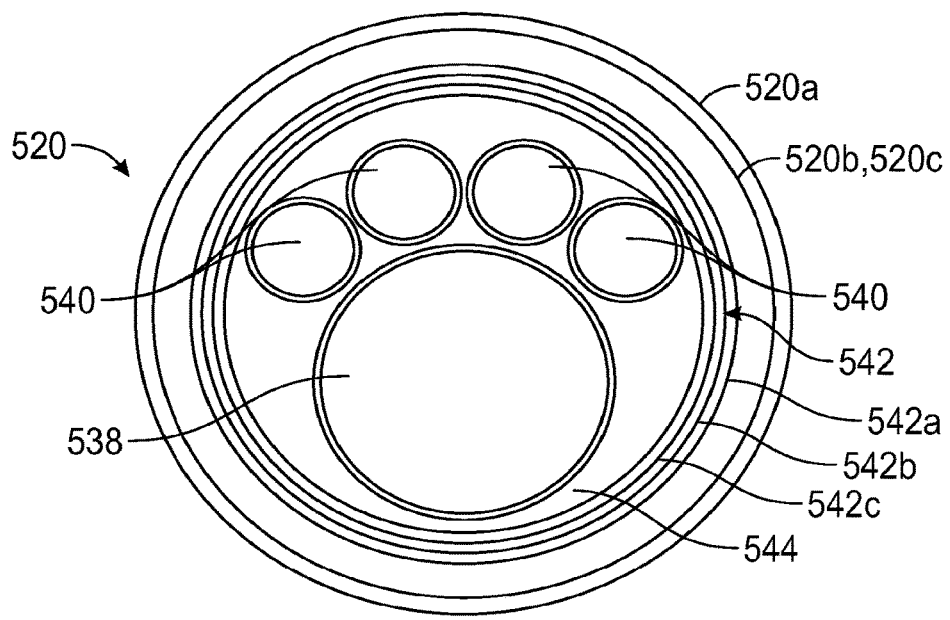
FIG. 16 is a plan view of a shaft of the delivery apparatus of FIG. 11.

Referring to FIG. 16, the outer shaft 520 can comprise a plurality of axially extending lumens, including an actuation shaft lumen 538 and a plurality of control member lumens 540 (e.g., four in the illustrated embodiment). In some embodiments, the outer shaft 520 can comprise more (e.g., six) or less (e.g., two) than four control member lumens 540.

The actuation shaft lumen 538 can be configured to receive the actuation shaft 512, and the control member lumens 540 can be configured to receive one or more clasp control members 524. The lumens 538, 540 can also be configured such that the actuation shaft 512 and clasp control members 524 can be movable (e.g., axially and/or rotationally) relative to the respective lumens 538, 540. In particular embodiments, the lumens 538, 540 can comprise a liner or coating configured to reduce friction within the lumens 538, 540. For example, the lumens 538, 540 can comprise a liner comprising PTFE.

Referring still to FIGS. 15-16, the outer shaft 520 can be formed from various materials, including metals and polymers. For example, in one particular embodiment, the proximal end portion 520a can comprise stainless steel and the distal and intermediate portions 520b, 520c can comprise PEBA (e.g., PEBAX®). The outer shaft 520 can also comprise an outer covering or coating, such as a polymer that is reflowed over the portions 520a, 520b, and 520c.

The outer shaft 520 can include one or more coil portions 542 disposed radially outwardly from the lumens 538, 540. For example, in one particular embodiment, the outer shaft 520 can comprise a first coil 542a, a second coil 542b, and a third coil 542c. The first coil 542a can be the radially outermost coil, the third coil 542c can be the radially innermost coil, and the second coil 542b can be radially disposed between the first coil 542a and the third coil 542c.

The coil portions 542 can comprise various materials and/or configurations. For example, the coil portions 542 can be formed from stainless steel. In one particular embodiment, the first and third coils 542a, 542c comprise stainless steel coils wound in a left hand configuration, and the second coil 542b comprises a stainless steel coil wound in a right hand configuration.

The coil portions 542 can also comprise various pitches. The pitch of one or more of the coil portions 542 can be the same as or different than the pitch of one or more other coil portions 542. In one particular embodiment, the first and second coils 542a, 542b can have a first pitch (e.g., 0.74 in.), and the third coil can comprise a second pitch (e.g., 0.14 in.).

The outer shaft 520 can also comprise a tie layer 544 disposed radially inwardly from the third coil 542c. The tie layer 544 can be formed of various materials including polymers, such as PEBA (e.g., PEBAX®).

Figure 17:
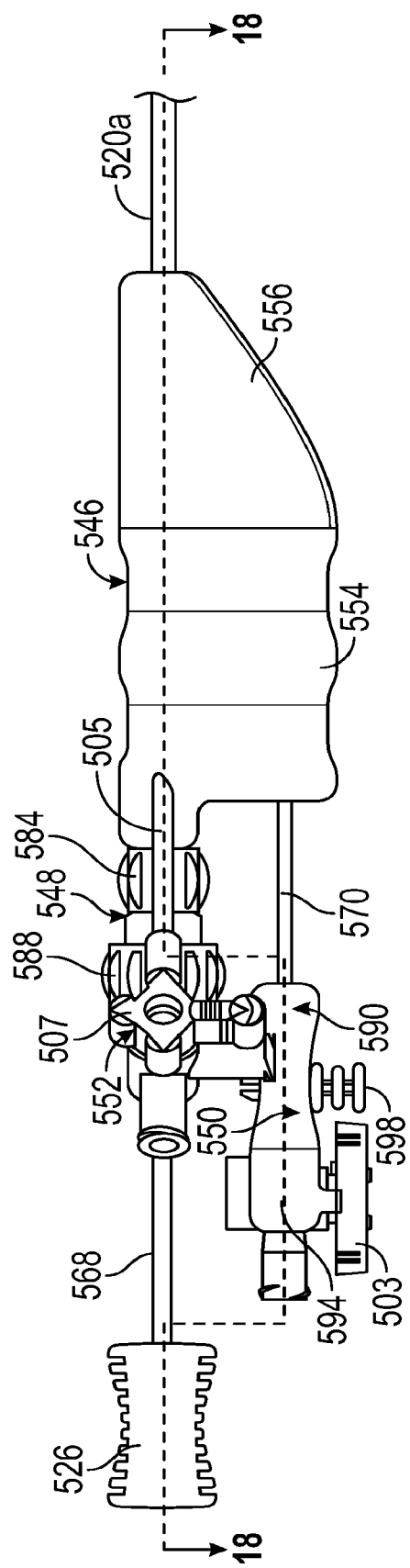
FIG. 17 is a side elevation view of a proximal end portion of the delivery apparatus of FIG. 11.
Figure 18:
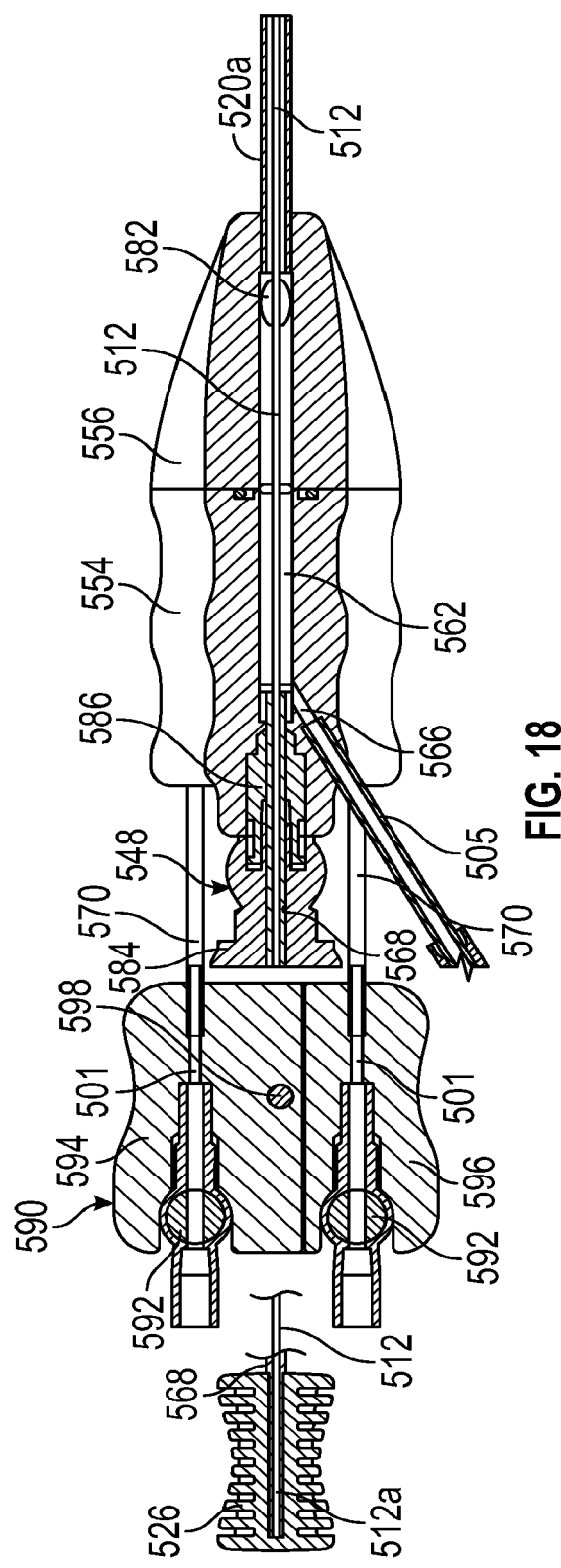
FIG. 18 is a cross-sectional view of the proximal end portion of the delivery apparatus of FIG. 11, taken along the line 18-18 shown in FIG. 17.
Figure 19:
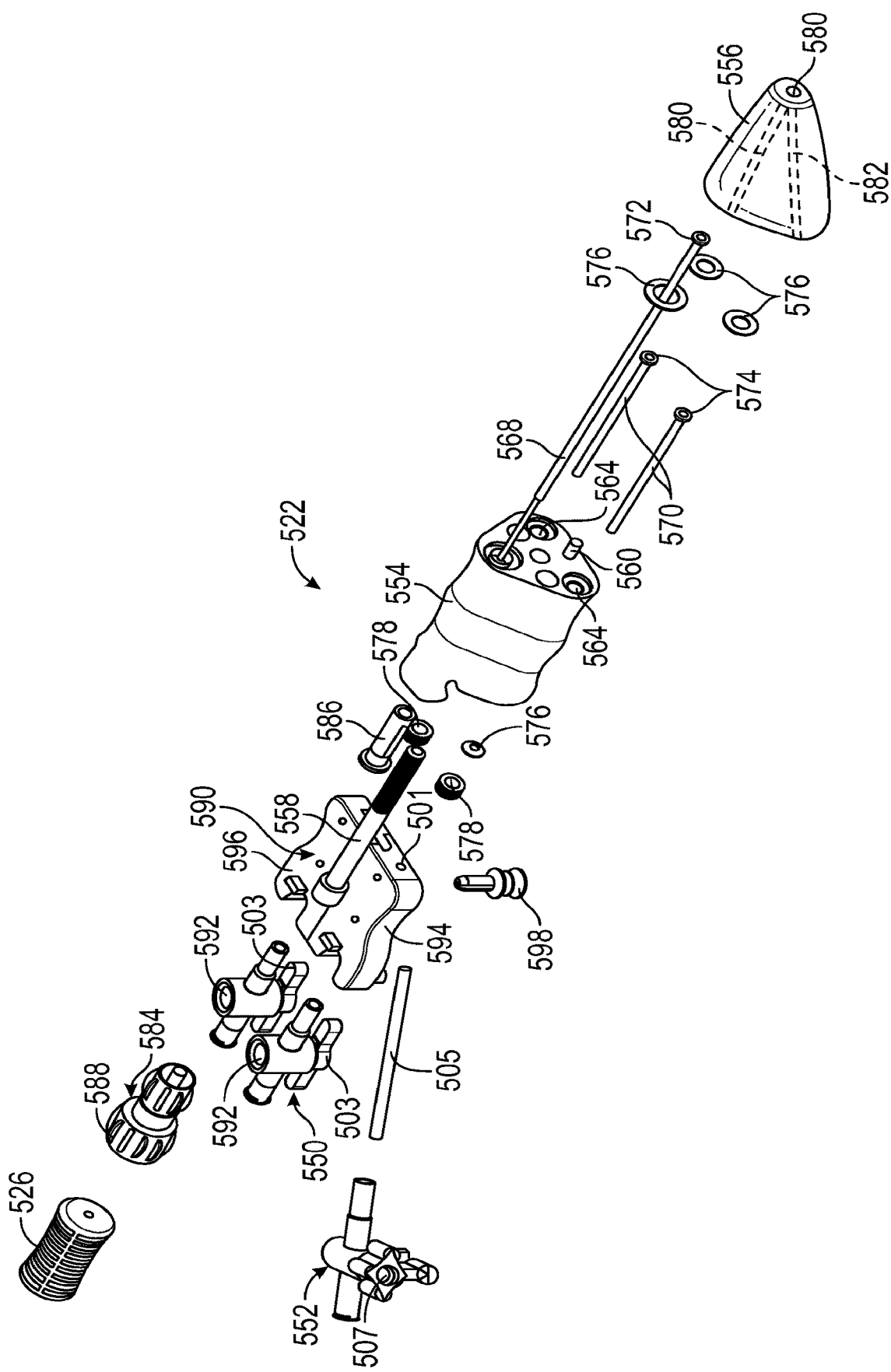
FIG. 19 is an exploded view of the proximal end portion of the delivery apparatus of FIG. 11.

As shown in FIGS. 17-19, the handle 522 of the third catheter 508 can include a housing 546, an actuation lock mechanism 548, a clasp control mechanism 550, and a flushing mechanism 552. Referring to FIG. 17, a distal end portion of the housing 546 can be coupled to the proximal end portion 520a of the outer shaft 520. The actuation lock mechanism 548, the clasp control mechanism 550, and a flushing mechanism 552 can be coupled to a proximal end of the housing 546. The actuation lock mechanism 548 can be configured to selectively lock the position of the actuation shaft 512 relative to the housing 546 and the outer shaft 520. The clasp control mechanism 550 can also be coupled to proximal end portions of the clasp control members 524 and can be configured to secure the clasp control members 524 relative to the handle 522 and to move the clasp control members 524 relative to the outer shaft 520 and the actuation shaft 512. The flushing mechanism 552 can be configured for flushing (e.g., with a saline solution) the outer shaft 520 prior to inserting the outer shaft 520 into a patient's vasculature.

As best shown in FIGS. 18-19, the housing 546 of the handle 522 can comprise a main body 554 and a nose portion 556 coupled to a distal end portion of the main body 554. The main body 554 and the nose portion 556 can be coupled together in various manners, including fasteners 558 and/or pins 560 (e.g., as shown in the illustrated embodiment), adhesive, and/or other coupling means. The housing 546 can be formed from various materials, including polymers (e.g., polycarbonate).

The main body 554 of the housing 546 can comprise a plurality of lumens, including an actuation shaft lumen 562, control member lumens 564 (FIG. 19), and a flushing lumen 566 that is fluidly connected to the actuation shaft lumen 562 (FIG. 18). As best shown in FIG. 19, the main body 554 can also include a plurality of tubes (e.g., hypotubes), including an actuation tube 568 and control member tubes 570 that are disposed at least partially in the actuation shaft lumen 562 and the control member lumens 564, respectively. The tubes 568, 570 can be axially movable (e.g., slidable) relative the lumens 562, 564, respectively.

The proximal end of the actuation tube 568 can extend proximally from the main body 554 and can be coupled to the knob 526 and to the proximal end portion 512a of the actuation shaft 512. The proximal ends of the control member tubes 570 can extend proximally from the main body 554 and can be coupled to the clasp control mechanism 550 and the clasp control members 524.

The distal ends of the tubes 568, 570 can comprise flanges 572, 574 configured to engage a stopper to limit the axial movement of the tubes 568, 570 relative to the housing 546. For example, the flanges 572, 574 can be configured to contact respective surfaces of the main body 554 (e.g., a lip) to prevent to tubes 568, 570 from withdrawing completely from the proximal ends of the lumens 562, 564, respectively.

The actuation tube 568 can be configured to receive and be coupled to the proximal end portion of the actuation shaft 512. The control member tubes 570 can be configured to receive portions of the clasp control mechanism 550, as further described below. The tubes 568, 570 can be formed from various materials, including polymers and metals (e.g., stainless steel).

In some embodiments, the main body 554 can include a plurality of seal members 576 (e.g., O-rings) configured to prevent or reduce blood leakage through the lumens and around the shafts and/or tubes. The seal members can be secured relative to the main body 554, for example, by fasteners 578 (e.g., hollow-lock or socket-jam set screws).

As best shown in FIG. 19, the nose portion 556 of the housing 546 can comprise a plurality of lumens, including an actuation shaft lumen 580 and control member lumens 582. The actuation shaft lumen 580 of the nose portion 556 can be extend coaxially with the actuation shaft lumen 562 of the main body 554. Proximal ends of the control member lumens 582 of the nose portion 556 can be aligned with the control member lumens 564 of the main body 554 at the proximal end of the nose portion 556 (i.e., the lumens 582, 564 are in the same plane). The control member lumens 582 can extend towards each other from their proximal ends at an angle (i.e., relative to the control member lumens 564 of the main body 554), and distal ends of the control member lumens 582 can intersect the actuation shaft lumen 580 of the nose portion 556 at a location near the distal end of the nose portion 556. In other words, the proximal ends of the lumens 582 are in a first plane that is parallel to a longitudinal axis of the catheter (i.e., the plane of the control member lumens 564 of the main body 554), and the distal ends of the lumens 582 are in a second plane that is parallel to a longitudinal axis of the catheter (i.e., the plane of the actuation shaft lumen 562 of the main body 554).

As best shown in FIG. 18, the actuation shaft lumen 580 of the nose portion 556 can be configured to receive the proximal end portion of the outer shaft 520. The proximal end portion of the outer shaft 520 can be coupled to the nose portion 556 in various ways such as with adhesive, fasteners, frictional fit, and/or other coupling means.

Referring still to FIG. 18, the actuation lock mechanism 548 of the handle 522 can be coupled to the proximal end portion of the main body 554 of the housing 546 and to the actuation tube 568. The actuation lock mechanism 548 can be configured to selectively control relative movement between the actuation tube 568 and the housing 546. This, in turn, selectively controls relative movement between the actuation shaft 512 (which is coupled to the actuation tube 568) and the outer shaft 520 (which is coupled to the nose portion 556 of the housing 546).

In some embodiments, the actuation lock mechanism 548 can comprise a lock configuration, which prevents relative movement between the actuation tube 568 and the housing 546, and a release configuration, which allows relative movement between the actuation tube 568 and the housing 546. In some embodiments, the actuation lock mechanism 548 can be configured to include one or more intermediate configurations (i.e., in addition to the lock and release configuration) which allow relative movement between the actuation tube 568 and the housing 546, but the force required to cause the relative movement is greater than when the actuation lock mechanism is in the release configuration.

As shown in FIG. 18 of the illustrated embodiment, the actuation lock mechanism 548 can comprise a lock (e.g., a Tuohy-Borst adapter) 584 and a coupler (e.g., a female luer coupler) 586. The coupler 586 can be attached to the distal end of the lock 584 and coupled to the proximal end of the main body 554 of the housing 546. The actuation tube 568 can extend coaxially through the lock 584 and the coupler 586. As such, rotating a knob 588 of the lock 584 in a first direction (e.g., clockwise) can increase the frictional engagement of the lock 584 on the actuation tube 568, thus making relative movement between the actuation tube 568 and the housing 546 more difficult or preventing it altogether. Rotating a knob 588 of the lock 584 in a second direction (e.g., counterclockwise) can decrease the frictional engagement of the lock 584 on the actuation tube 568, thus making relative movement between the actuation tube 568 and the housing 546 easier.

In other embodiments, actuation lock mechanism 548 can comprise other configurations configured for preventing relative movement between the actuation tube 568 and the housing 546. For example, the actuation lock mechanism 548 can include a lock configured similar to a stopcock valve in which a plunger portion of valve selectively engages the actuation tube 568.

In some embodiments, the actuation lock mechanism 548 can include a release member (e.g., a set screw or a pin). The release member can extend into the housing 546 and can selectively engage the actuation tube 568. When the release member is engaged with the actuation tube 568 (e.g., by inserting the release member into the housing 546 and into contact with the actuation tube 568), the release member can, for example, prevent the actuation tube 568 and thus the actuation shaft 512 from being completely withdrawn from their respective lumens 568, 580 (e.g., when actuating the anchors 204). When the release member is released from the actuation tube 568 (e.g., by withdrawing it from the housing 546 and/or moving it out of contact with the actuation tube 546), the actuation tube 568 and thus the actuation shaft 512 can be completely withdrawn from their respective lumens 568, 580 (e.g., when releasing the prosthetic spacer device 200 from the delivery apparatus 502).

The clasp control mechanism 550 can comprise an actuator member 590 and one or more locking members 592 (e.g., two in the illustrated embodiment). A distal end portion of the actuator member 590 can be coupled to the control member tubes 570, which extend from the proximal end of the main body 554 of the housing 546, as best shown in FIG. 18. The locking members 592 can be coupled to a proximal end portion of the actuator member 590.

As shown in the illustrated embodiment, the actuator member 590 can, optionally, comprise a first side portion 594 and a second side portion 596 selectively coupled to the first side portion 594 by a connecting pin 598. The actuator member 590 can be configured such that the first and second side portions 594, 596 move together when the connecting pin 598 is inserted through the first and second side portions 594, 596. When the connecting pin 598 is withdrawn, the first and second side portions 594, 596 can be moved relative to each other. This can allow the clasp control members 524 (which are releasably coupled to the first and second side portions 594, 596 by the locking members 592) to be individually actuated.

The connection between the first and second side portions 594, 596 can be configured such that the first and second side portions 594, 596 can move axially (i.e., proximally and distally) but not rotationally relative to each other when the connecting pin 598 is withdrawn. This can be accomplished, for example, by configuring the first side portion 594 with keyed slot or groove and configuring the second side portion 596 with a keyed projection or tongue that corresponds to the keyed slot or groove of the first side portion 594. This can, for example, prevent or reduce the likelihood that the clasp control members 524 from twisting relative to the outer shaft 520.

The first and second side portions 594, 596 can include axially extending lumens 501. Distal ends of the lumens 501 can be configured to receive the proximal end portions of the control member tubes 570. Proximal ends of the lumens 501 can be configured to receive portions of the locking members 592. As noted above, the proximal end portions of the clasp control members 524 extend through respective locking members 592.

The locking members 592 can be configured to selectively control relative movement between a clasp control member 524 and the respective first or second side portion 594, 596 of the actuator member 590. The locking members 592 can comprise a lock configuration, which prevents relative movement between a clasp control member 524 and the respective first or second side portion 594, 596, and a release configuration, which allows relative movement between a clasp control member 524 and the respective first or second side portion 594, 596. In some embodiments, the locking members 592 can also comprise one or more intermediate configurations (i.e., in addition to the lock and release configuration) which allows relative movement between a clasp control member 524 and the respective first or second side portion 594, 596, but the force required to cause the relative movement is greater than when the locking members 592 are in the release configuration.

As shown in the illustrated embodiment, the locking members 592 can be configured similar to stopcock valves. Thus, rotating knobs 503 in a first direction (e.g., clockwise) can increase the frictional engagement between the locking members 592 on the clasp control members 524 and make relative movement between a clasp control member 524 and the respective first or second side portion 594, 596 more difficult or prevent it altogether. Rotating knobs 503 in a second direction (e.g., counterclockwise) can decrease the frictional engagement between the locking members 592 on the clasp control members 524 and make relative movement between a clasp control member 524 and the respective first or second side portion 594, 596 easier. In other embodiments, the locking members 592 can comprise other configurations configured for preventing relative movement between the locking members 592 on the clasp control members 524.

The flushing mechanism 552 can comprise a flushing tube 505 and a valve 507 (e.g., a stopcock valve). A distal end of the flushing tube 505 can be coupled to and in fluidic communication with the flushing lumen 566 and thus with the actuation shaft lumen 562 of the main body 554. A proximal end of the flushing tube 505 can be coupled to the valve 507. In this manner, the flushing mechanism 552 can be configured for flushing (e.g., with a saline solution) the outer shaft 520 prior to inserting the outer shaft 520 into a patient's vasculature.

The clasp control members 524 can be configured to manipulate the configuration of the clasps 206, as further described below. As best shown in FIG. 15, each of the clasp control members 524 can be configured as a suture (e.g., wire or thread) loop. Proximal end portions of the clasp control members 524 can extend proximally from the proximal end portion of the clasp control mechanism 550 and can be releasably coupled to the locking members 592 of the clasp control mechanism 550.

From the locking members 592, the clasp control members 524 can form loops extending distally through the lumens 501 of the clasp control mechanism 550, through the control member tubes 570, the control member lumens 564, 582 of the handle 522, and through the control member lumens 540 of the outer shaft 520. The clasp control members 524 can extend radially outwardly from the lumens 540, for example, through the ports 533 (FIG. 13) of the coupler 514. The clasp control members 524 can then extend through openings 234 of the clasps 206 (e.g., similar to the openings 142 of the prosthetic spacer device 100). The clasp control members 524 can then extend proximally back to the coupler 514, radially inwardly through the ports 533 of the coupler 514, and then proximally through the outer shaft 520 and the handle 522, and to the locking members 592 of the clasp control mechanism 550.

In FIG. 15, the clasp control members 524 are shown slacken and the clasps 206 are partially open in order to illustrate the clasp control members 524 extending through the openings 234 of the clasps 206. However, ordinarily when the clasp control members 524 are slacken, the clasps 206 would be in the closed configuration.

As shown in the illustrated embodiment, each of the clasp control members 524 can extend through multiple control member lumens 540 of the outer shaft 520. For example, each of the clasp control members 524 can be looped through two of the lumens 540. In other embodiments, each of the clasp control members 524 can be disposed in a single control member lumen 540. In yet other embodiments, multiple clasp control members 524 can be disposed in a single control member lumen 540.

With the clasp control members 524 coupled to the clasps 206, the clasp control mechanism 550 can be used to actuate the clasps 206 between open and closed configurations. The clasps 206 can be opened by moving the actuator member 590 proximally relative to the knob 526 and the housing 546. This increases tension of the clasp control members 524 and causes the clasp 206 to move from the closed configuration to the open configuration. The clasps 206 can be closed by moving the actuator member 590 distally relative to the knob 526 and the housing 546. This decreases tension on the clasp control members 524 and allows the clasp 206 to move from the open configuration to the closed configuration. The clasps 206 can be individually actuated by removing the connecting pin 598 and moving the first or second side portions 594, 596 relative to each other, the knob 526, and the housing 546.

When the handle 522 is assembled as best shown in FIG. 17-18, the actuation shaft 512 can extend distally from the knob 526, through the actuation tube 568, through the actuation lumens 562, 580 of the housing 546, through the actuation shaft lumen 538 of the outer shaft 520, and through the coupler 514.

Figure 20:
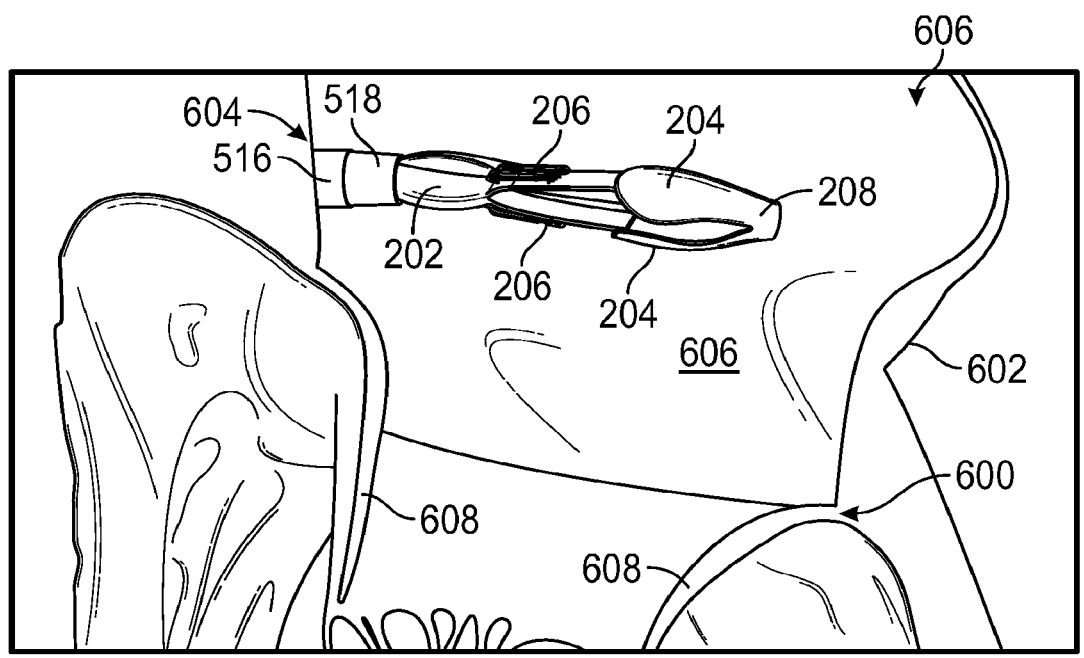
FIGS. 20-29 illustrate an exemplary procedure of the delivery assembly of FIG. 11 being used to repair a native mitral valve of a heart, which is partially shown.

FIGS. 20-27 show the delivery assembly 500 being used, for example, to implant the prosthetic spacer device 200 in native mitral valve 600 of a heart 602 using a transseptal delivery approach. Although not shown, a guide wire can be inserted into the patient's vasculature (e.g., a femoral vein) through an introducer sheath. The guide wire can be advanced through the femoral vein, through the inferior vena cava, into the right atrium, through the interatrial septum 604 (e.g., via the fossa ovalis), and into the left atrium 606. The first sheath 516 of the first catheter 504 can be advanced over the guide wire such that a distal end portion of the first sheath 516 is disposed in the left atrium 606, as best shown in FIG. 20.

With the prosthetic spacer device 200 coupled to the third catheter 508 (e.g., as shown in FIG. 12) and configured in a radially compressed, delivery configuration, the prosthetic spacer device 200 can be loaded into the second sheath 518 of the second catheter 506, which retains the prosthetic spacer device 200 in the delivery configuration. In this manner, the distal end portion of the second sheath 518 serves as a delivery capsule for the prosthetic implant 200. In some embodiments, the radially compressed, delivery configuration can be an axially elongate configuration (e.g., similar to the configuration shown in FIG. 20). In other embodiments, the radially compressed, delivery configuration can be an axially foreshorten configuration (e.g., similar to the configuration shown in FIG. 22). The second catheter 506 along with the prosthetic spacer device 200 and the third catheter 508 can then be advanced together through the first catheter 504 until a distal end portion of the second sheath 518 extends outwardly from the distal end portion of the first sheath 516 and is disposed in the left atrium 606, as shown in FIG. 20.

As shown in FIG. 20, the prosthetic spacer device 200 can be advanced from the second sheath 518 by distally advancing the outer shaft 520 and the actuation shaft 512 of the third catheter 508 relative to the second sheath 518 and/or retracting the second sheath 518 relative to the outer shaft 520 and the actuation shaft 512, thus forcing the anchors 204 out of the second sheath 518. Once exposed from the second sheath 518, the anchors 204 can be folded by retracting the actuation shaft 512 of the third catheter 508 relative to the outer shaft 520 of the third catheter 508 and/or by advancing the outer shaft 520 relative to the actuation shaft 512, causing the anchors 204 to bend from the configuration shown in FIG. 20, to the partially folded configuration shown in FIG. 21, and then to the fully folded configuration shown in FIG. 22. This can be accomplished, for example, by placing the actuation lock mechanism 548 in the release configuration (e.g., by rotating the knob 588 counterclockwise relative to the handle 522) and then moving the knob 526 proximally relative to the housing 546. At any point in the procedure, the physician can lock the relative position of the actuation shaft 512 and the outer shaft 520, and thus the position of the anchors 204, by actuating the actuation lock mechanism 548.

Figure 22:
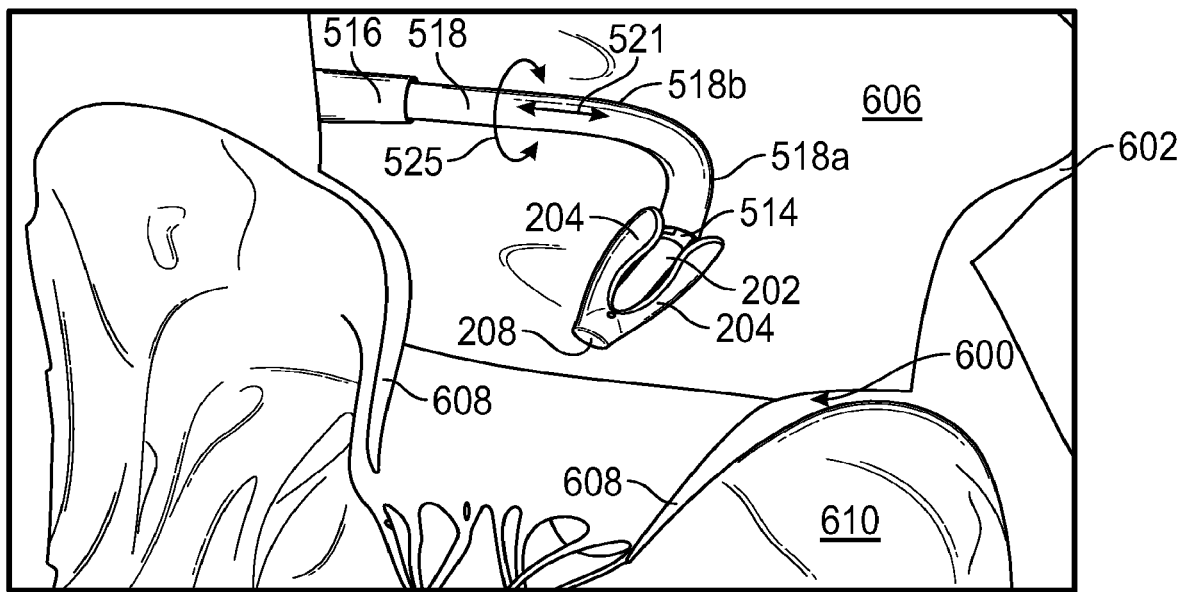

The prosthetic spacer device 200 can then be positioned coaxial relative to the native mitral valve 600 by manipulating (e.g., steering and/or bending) the second sheath 518 of the second catheter 506, as shown in FIG. 22. The curvature of the second sheath 518 can be adjusted (e.g., with the steering mechanism) so that a distal steerable section 518a extends at about a 90-degree angle relative to a section 518b that extends proximally from the steerable section 518a. Advantageously, this positions the steerable distal section 518a and the prosthetic spacer device 200 along an axis that is substantially perpendicular to a plane defined by the native mitral valve. Stated another way, the axis extending through the steerable distal section 518a and the prosthetic spacer device 200 is coaxial or substantially parallel to the flow path of the native mitral valve.

Retracting or advancing the second sheath 518 of the second catheter 506 and the outer shaft 520 of the third catheter 508 (e.g., in the directions shown by the arrow 521) relative to the first sheath 516 of the first catheter 504 and the left atrium 606 moves the outer shaft 520 of the third catheter 508 and the prosthetic spacer device 200 in the medial and lateral directions (e.g., in the directions shown by arrow 523 in FIG. 28) relative to the native leaflets 608. As the second sheath 518 and outer shaft 520 are advanced and/or retracted, the positioning of the prosthetic spacer device 200 relative to the native mitral valve in the superior/inferior directions (e.g., up/down in the orientation shown in FIG. 22) remains at least substantially constant, and/or the second sheath 518 does not "whip" due to the configuration of the steering mechanism of the second catheter 506, which is described above. Rotating (which can also be referred to as "torquing") the second sheath 518 of the second catheter 506 (e.g., in the directions shown by the arrow 525 in FIG. 22) relative to the first sheath 516 of the first catheter 504 and the left atrium 606 pivots the outer shaft 520 of the third catheter 508 and the prosthetic spacer device 200 in the anterior/posterior directions (e.g., in the directions shown by arrow 527 in FIG. 28). The prosthetic spacer device 200 can also be rotated (e.g., by rotating the housing 546) relative to the native mitral valve 600 in order to align the anchors 204 with native leaflets 608 of the native mitral valve 600. The positioning of the prosthetic spacer device 200 relative to the native mitral valve in the superior/inferior directions (e.g., up/down in the orientation shown in FIG. 22) can be adjusted by retracting/advancing the outer shaft 520 of the third catheter 508 relative to the second sheath of the second catheter 506. Thus, one advantage of the disclosed delivery apparatus is that the positioning of the prosthetic spacer device can be adjusted independently in three directions (i.e., the medial/lateral, anterior/posterior, and superior/inferior directions). For example, actuating the delivery apparatus such that the prosthetic spacer device moves in the medial/lateral directions does not affect the positioning of the prosthetic spacer device in the anterior/posterior directions or the superior/inferior directions. The three-way and/or independent maneuverability of the delivery apparatus 502 therefore allows the practitioner to accurately and/or precisely position the prosthetic spacer device 200 at the desired implantation location relative to the native leaflets (e.g., at the A2/P2 positions near the center of a coaptation line 612 (FIG. 28) of the native leaflets) in a relatively quick and/or easy manner.

Figure 23:
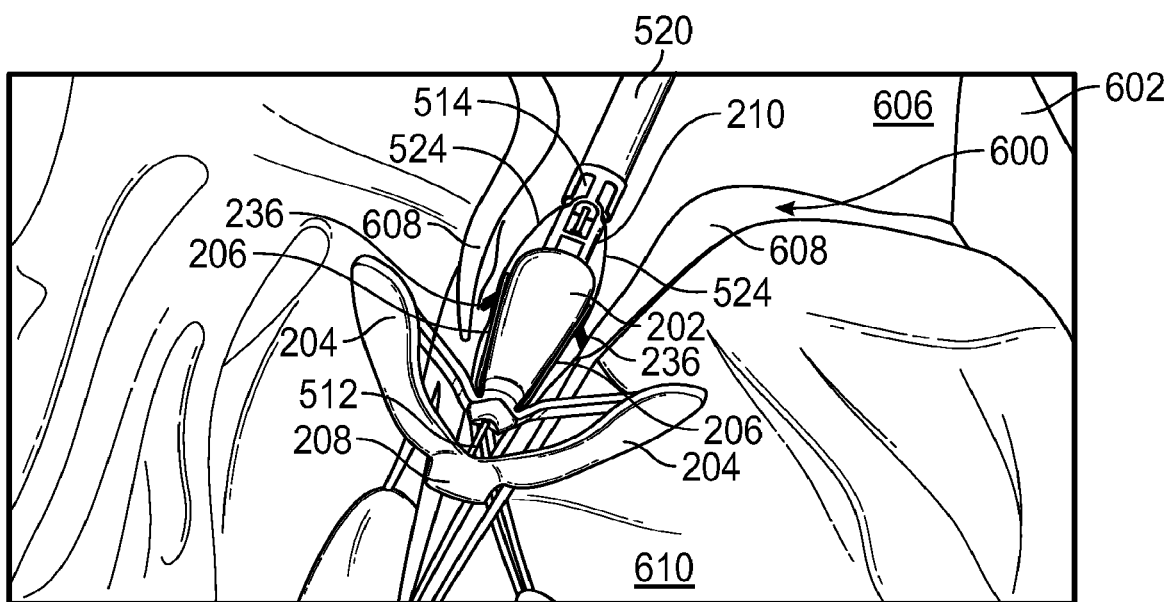

The anchors 204 of the prosthetic spacer device 200 can then be partially opened (i.e., moved radially outwardly relative to the spacer member 202) to the configuration shown in FIG. 23 by moving the knob 526 distally relative to the housing 546. The prosthetic spacer device 200 can then be advanced through the annulus of the native mitral valve 600 and at least partially into the left ventricle 610 by advancing the handle 522 of the third catheter 508 relative to the second catheter 506. The prosthetic spacer device 200 can then be partially retracted such that the anchors 204 are positioned behind the ventricular portions of the native leaflets 608 (e.g., at the A2/P2 positions) and the spacer member 202 is disposed on the atrial side of the native leaflets 608. Alternatively, the prosthetic spacer device 200 can be advanced through the native valve in the fully folded configuration (as shown in FIG. 22), after which the anchors 204 can be opened.

Figure 24:
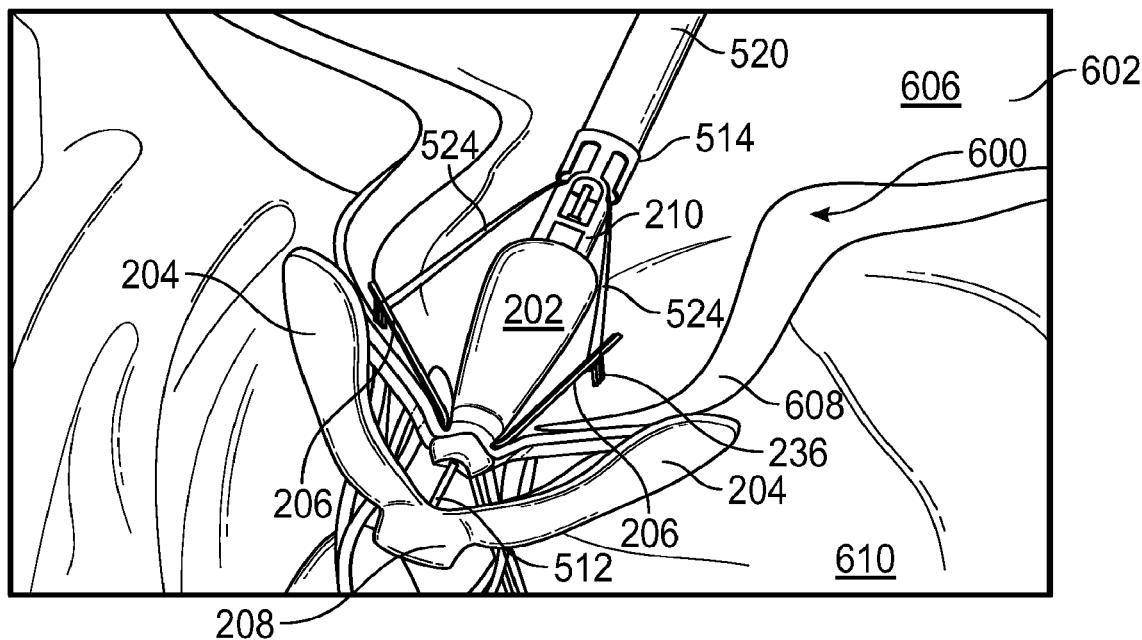

In this configuration, the native leaflets 608 can be secured relative to the anchors 204 by capturing the native leaflets with the clasps 206. The native leaflets 608 can be captured simultaneously or separately by actuating the actuator member 590. For example, FIG. 24 shows separate leaflet capture. This can be accomplished by removing the connecting pin 598 from the actuator member 590 and moving the first or second side portions 594, 596 relative to each other, the knob 526, and the housing 546. Moving the first or second side portions 594, 596 distally relative to the knob 526 and the housing 546 closes the clasps 206 on the native leaflets 608 (e.g., as shown by the left clasp 206 as illustrated in FIG. 24). Moving the first or second side portions 594, 596 proximally relative to the knob 526 and the housing 546 opens the clasps 206 (e.g., as shown by the right clasp 206 as illustrated in FIG. 24). Once a clasp 206 is closed, a physician can re-open the clasp 206 to adjust the positioning of the clasp 206.

As the clasps 206 re-open, the clasps 206 initially move radially inwardly toward the spacer member 202 (e.g., as shown with the right clasp 206 in FIG. 24) until the clasps 206 contact the spacer member 202 (e.g., as shown in FIG. 23). In some instances, barbs 236 of the clasps 206 may retain and pull the native leaflets 608 toward the spacer member 202 as the clasps 206 are re-opened. Once the clasps 206 contact the spacer member 202, further tensioning the clasp control member 524 moves the clasps 206 slightly proximally relative to the spacer member 202 (and causes the anchors 204 to slightly unfold). The proximal movement of the clasps 206 can, for example, withdraw the barbs 236 from the native leaflets 608, which can facilitate repositioning and/or retrieval of the prosthetic spacer device 200.

Figure 25:
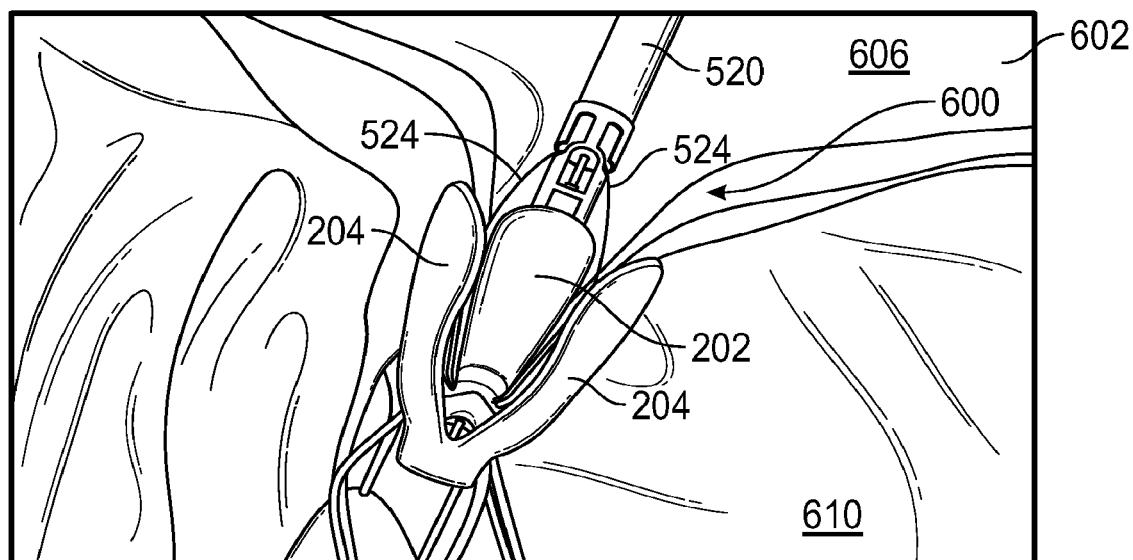

With both of the native leaflets 608 secured within the clasps 206, the physician can move the knob 526 proximally relative to the housing 546. This pulls the anchors 204 and thus the native leaflets 608 radially inwardly against the spacer member 202, as shown in FIG. 25. The physician can then observe the positioning and/or reduction in regurgitation. If repositioning or removal is desired the physician can re-open the anchors 204 and/or the clasps 206.

Figure 26:
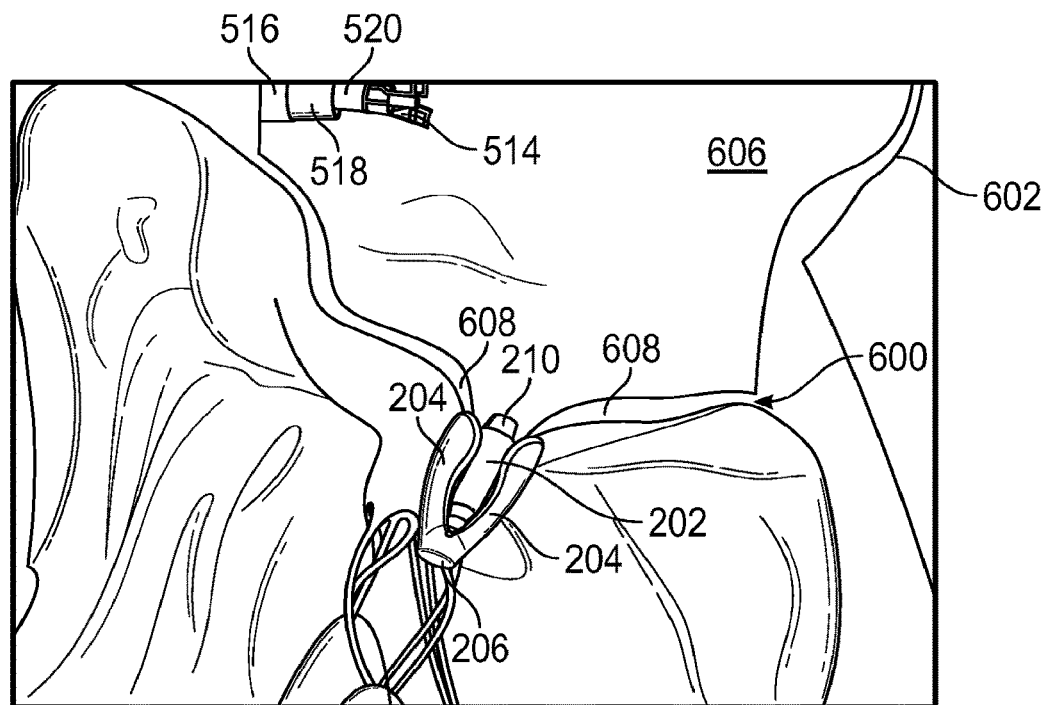

Once the desired positioning and/or reduction in regurgitation is achieved, the physician can release the prosthetic spacer device 200 from the delivery apparatus 502. The clasps 206 can be released from the delivery apparatus 502 by releasing the clasp control members 524 from the locking members 592 and unthreading the clasp control members 524 from the openings 234 of the clasps 206. The distal collar 208 of the prosthetic spacer device 200 can be released from the delivery apparatus 502 by rotating the knob 526 in the second direction relative to the housing 546 such that the actuation shaft 512 withdraws from the bore 226. The actuation shaft 512 can then be retracted proximally through the prosthetic spacer device 200 by pulling the knob 526 proximally relative to the housing 546. The proximal collar 210 of the prosthetic spacer device 200 can be released from the delivery apparatus 502 by retracting the actuation shaft 512 proximally relative to the coupler 514 such that the distal end portion of the actuation shaft 512 withdraws from the eyelets 534 of the coupler 514. This allows the flexible arms 528 of the coupler 514 to move radially outwardly away from the projections 230 of the proximal collar 210. The stabilizer members 530 of the coupler 514 can then be withdrawn from the guide openings 232 of the proximal collar 210 by pulling the housing 546 proximally, thereby releasing the prosthetic spacer device 200 from the delivery apparatus 502 as shown in FIG. 26.

The shafts 512, 520 of the third catheter 508 can then be retracted proximally into the second sheath 518 of the second catheter 506, and the second sheath 518 of the second catheter 506 can be retracted proximally into the first sheath 516 of the first catheter 504. The catheters 504, 506, 508 can then be retracted proximally and removed from the patient's vasculature.

Figure 27:
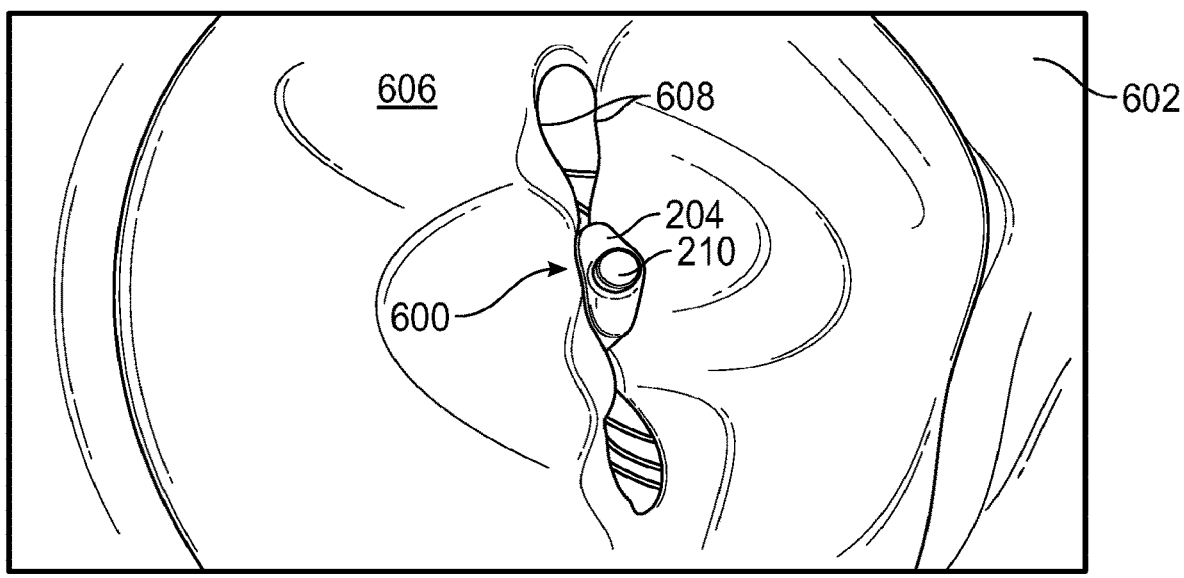

With the prosthetic spacer device 200 implanted at the A2/P2 position, the native mitral valve 600 can, in some embodiments, comprise a double orifice during ventricular diastole, as shown in FIG. 27. During ventricular systole, the native leaflets 608 can coapt together and/or against the prosthetic spacer device 200 to prevent or reduce mitral regurgitation, as shown in FIG. 28.

Figure 28:
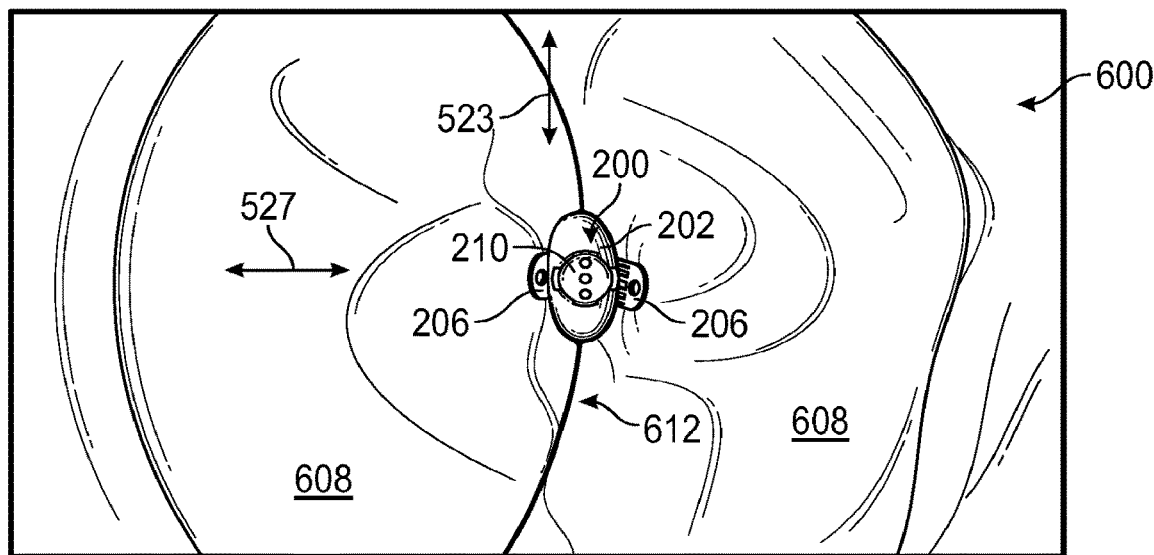
Figure 29:
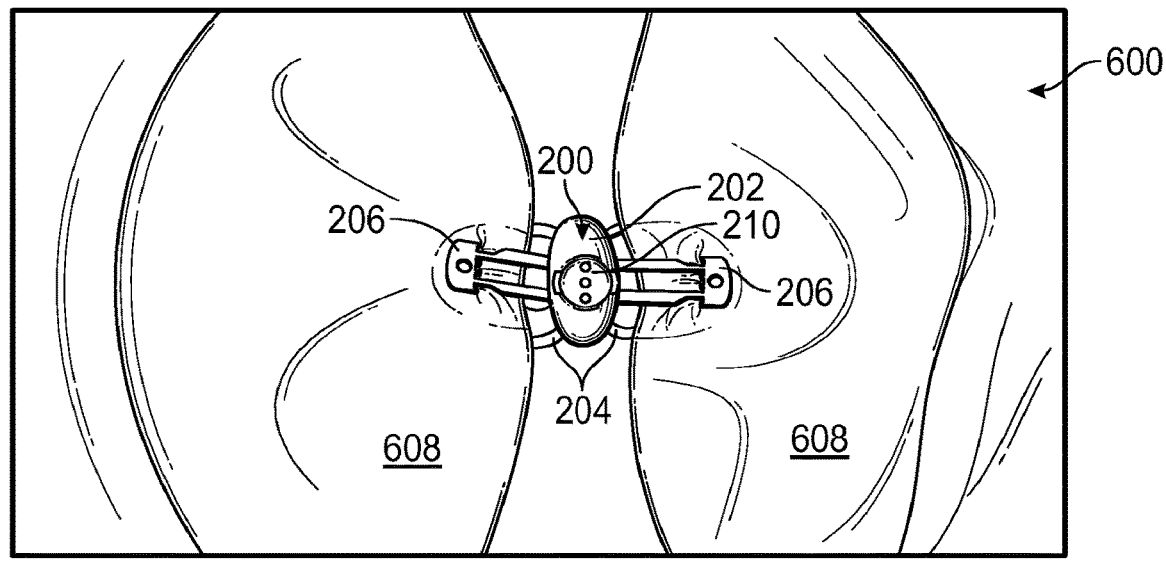

In other embodiments, the anchors 204 can move radially outwardly relative to the spacer member 202 to a partially open configuration during ventricular diastole such that the native mitral valve 600 has a single orifice, as shown in FIG. 29. The anchors 204 can move radially inwardly relative to the spacer member 202 to a closed configuration during ventricular systole such that the native leaflets 608 coapt together and/or against the prosthetic spacer device 200 to prevent or reduce mitral regurgitation, as shown in FIG. 28.

As the anchors 204 open and close during the natural cardiac cycles, the clasps 206 can retain the native leaflets 608 against the anchors 204, as shown in FIGS. 28-29.

Configuring the prosthetic spacer device 200 in this manner allows the native leaflets 608 to move naturally upon implantation. This can, for example, promote antegrade blood flow during ventricular diastole, while still reducing or preventing retrograde blood flow during ventricular systole. It can also reduce or prevent native tissue damage to the native leaflets. Overtime, endothelialization can form a tissue bridge between the anchors and the spacer member.

FIGS. 30-31 show another exemplary embodiment of a handle 700 for the delivery apparatus 502, in particular for use with the third catheter 508. Referring to FIG. 30, the handle 700 can comprise a housing 702, an actuation control mechanism 704, the clasp control mechanism 550, and a flushing mechanism (not shown, but see, e.g., the flushing mechanism 552 in FIG. 17). The housing 702 can include a main body 706 and the nose portion 556. The nose portion 556 of the housing 702 can be coupled to a proximal end portion of the outer shaft 520. The actuation control mechanism 704, the clasp control mechanism 550, and a flushing mechanism 552 can be coupled to a proximal end of the main body 706 of the housing 702.

The handle 700 can be configured similar to the handle 522, except that the handle 700 is configured such that rotational movement of a first knob 718 of the actuation control mechanism 704 relative to the housing 702 causes axial movement of the actuation tube 568 and the actuation shaft 512; whereas, the handle 522 is configured such that axial movement of the knob 526 (e.g., pushing and pulling) relative to the housing 546 causes axial movement of the actuation tube 568 and the actuation shaft 512.

As mentioned above, the housing 702 can include a main body 706 and the nose portion 556. Referring to FIG. 31, the main body 706 of the housing 702 can comprise an actuation lumen 708, control member lumens 710, and a flange portion 712. The flange portion 712 can extend axially from a proximal end portion of the main body 706 and annularly around the actuation lumen 708.

The flange portion 712 of the main body 706 can comprise one or more circumferential grooves 714, a bore (not shown), and a guide pin 716. The grooves 714 can be configured to interact with the actuation control mechanism 704, as further described below. The bore can extend radially inwardly from an outside diameter to an inside diameter of the flange portion 712 and can be configured to receive the guide pin 716. The guide pin 716 can be partially disposed in the bore and can extend radially inwardly from the bore such that the guide pin 716 protrudes into the actuation lumen 708.

Referring still to FIG. 31, the actuation control mechanism 704 can comprise a first knob 718, attachment pins 720, a drive screw 722, a collet 724, and a second knob 726. The first knob 718 can have a distal end portion 728 and a proximal end portion 730. The first knob 718 can be configured such that the inside diameter of the distal end portion 728 is relatively larger than the inside diameter of the proximal end portion 730. The distal end portion 728 can comprise side openings 732 that extend radially inwardly from an outside diameter to the inside diameter of the distal end portion 728.

Referring again to FIG. 30, the inside diameter of the distal end portion 728 can be configured such that the distal end portion 728 of the first knob 718 can extend over the flange portion 712 of the main body 706. The openings 732 (FIG. 31) can be configured to axially align with the grooves 714 when the first knob 718 is disposed over the flange portion 712. The attachment pins 720 can be configured so as to extend through the openings 732 of the first knob 718 and into grooves 714 of the flange portion 712. In this manner, the attachment pins 720 allow relative rotational movement and prevent relative axial movement between the first knob 718 and the flange portion 712.

The inside diameter of the proximal end portion 730 of the first knob 718 can have internal threads (not shown) configured to engage corresponding external threads 734 of the drive screw 722. As best shown in FIG. 31, the drive screw 722 can have a slot 736 that extends axially across the external threads 734. The slot 736 can be configured to receive the guide pin 716 of the flange portion 712. As such, when the handle 700 is assembled (FIG. 30) and the first knob 718 is rotated relative to the flange portion 712, the guide pin 716 prevents the drive screw 722 from rotating together with the first knob 718 and causes the drive screw 722 to move axially relative to the first knob 718 and the flange portion 712. In this manner, rotating the first knob 718 in a first direction (e.g., clockwise) moves the drive screw distally relative to the housing 702, and rotating the first knob 718 in a second direction (e.g., counterclockwise) moves the drive screw proximally relative to the housing 702.

The drive screw 722 can also have a lumen 738, as shown in FIG. 31. The lumen 738 can be configured such that the actuation tube 568 can extend through the drive screw 722. The lumen 738 can be configured such that a distal end portion 740 of the collet 724 can also be inserted into a proximal end portion of the lumen 738.

The second knob 726 can comprise a first, distal portion 742 and a second, proximal portion 744. The distal portion 742 can include internal threads (not shown) corresponding to the external threads 734 of the drive screw 722. The proximal portion 744 can comprise a conical inside surface configured to engage a proximal end portion 746 of the collet 724.

When assembled (FIG. 30), the actuation tube 568 can extend through the lumen 738 of the drive screw 722, through the collet 724, and through the second knob 726. The second knob 726 can be disposed over the collet 724 and the internal threads of the distal portion 742 of the second knob can threadably engage the external threads 734 of the drive screw 722. Accordingly, rotating the second knob 726 in a first direction (e.g., clockwise) relative to the drive screw 722 causes the proximal portion 744 of the second knob 726 to move toward the proximal end portion 746 of the collet 724 and thus urges the collet 724 radially inwardly against the actuation tube 568. As a result, the actuation tube 568 and the drive screw 722 move axially together when the first knob 718 is rotated relative to the housing 702. Rotating the second knob 726 in a second direction (e.g., counterclockwise) relative to the drive screw 722 causes the distal portion 742 of the second knob 726 to move away from the proximal end portion 746 of the collet 724 and thus allows the collet 724 to move radially outwardly relative to the actuation tube 568. As a result, the actuation tube 568 and the drive screw 722 can move relative to each other.

In lieu of or in addition to the collet 724, the actuation control mechanism 704 of the handle 700 can include a release member (e.g., a set screw or a pin). The release member can extend into the housing 702 (e.g., near the proximal end of the housing 702) and can selectively engage (e.g., threadably) the drive screw 722 and the actuation tube 568. When the release member is engaged with the drive screw 722 and the actuation tube 568 (e.g., by inserting the release member into the housing 702 and into contact with the drive screw 722 and the actuation tube 568), the release member can, for example, prevent the actuation tube 568 from moving relative to the drive screw 722, thus preventing the actuation shaft 512 from being completely withdrawn from their respective lumens 568, 580 (e.g., when actuating the anchors 204). When the release member is released from the drive screw 722 and the actuation tube 568 (e.g., by withdrawing it from the housing 702 and/or moving it out of contact with the actuation tube 546), the actuation tube 568 and thus the actuation shaft 512 can move relative to the drive screw 722 and can therefore be completely withdrawn from their respective lumens 568, 580 (e.g., when releasing the prosthetic spacer device 200 from the delivery apparatus).

With the prosthetic spacer device 200 coupled to the actuation shaft 512 and the outer shaft 520 of the delivery apparatus 502, the physician can use the actuation control mechanism 704 of the handle 700 to manipulate the anchors 204 of the prosthetic spacer device 200 relative to the spacer member 202 of the prosthetic spacer device 200. The actuation control mechanism 704 can be activated by rotating the second knob 726 in the first direction relative to the drive screw 722 to secure the actuation tube 568 and thus the actuation shaft 512 to the drive screw 722. The physician can then rotate the first knob 718 relative to the housing 702, which causes the drive screw 722 and thus the actuation tube 568 and the actuation shaft 512 to move axially relative to the relative to the housing 702 and thus the outer shaft 520. This, in turn, causes the anchors 204 (which are coupled to the actuation shaft 512 via the distal collar 208) to move relative to the spacer member 202 (which is coupled to the outer shaft 520 via coupler 514 and the proximal collar 210).

The prosthetic spacer device 200 can be released from the delivery apparatus 502 by rotating the second knob 726 in the second direction relative to the drive screw 722. This allows the actuation tube 568 and thus the actuation shaft 512 to move relative to the drive screw 722. The shafts 512, 520 of the delivery apparatus 502 can then be removed from the respective collars 208, 210 of the prosthetic spacer device 200, as described above.

Configuring a delivery apparatus with the actuation control mechanism 704 can provide several advantages. For example, the rotational forces required to actuate the first knob 718 of the handle 700 can be less than the axial forces required to actuate the knob 526 of the handle 700.

The actuation control mechanism 704 can also provide relatively more precise control of the anchors 204 because the axial movement of the actuation shaft 512 is controlled by rotation of the first knob 718 and the thread pitch of the drive screw 722 rather than be axial movement of the knob 526. In other words, the actuation control mechanism 704 can be configured, for example, such that one rotation of the first knob 718 moves the actuation shaft 512 a small axial distance (e.g., 1 mm); whereas, it may be relatively more difficult to axially move the knob 526 and thus the actuation shaft 512 in small increments (e.g., 1 mm).

Additionally, the actuation control mechanism 704 can prevent or reduce inadvertent movement and release of the actuation shaft 512. For example, because the actuation control mechanism 704 requires rotational movement of the first knob 718 to move the actuation shaft 512, it can prevent or reduce the likelihood that the actuation shaft 512 will move if the knob 526 is inadvertently contacted. Also, the physician has to rotate the second knob 726 to release the actuation tube 568 from the drive screw 722 by before the physician can rotate the knob 526 to release the actuation shaft 512 from the distal collar 208 of the prosthetic spacer device 200 and proximally retract the actuation shaft 512. This two-step release process could reduce the likelihood of a physician inadvertently releasing the prosthetic spacer device 200 from the delivery apparatus 502.

Figure 32:
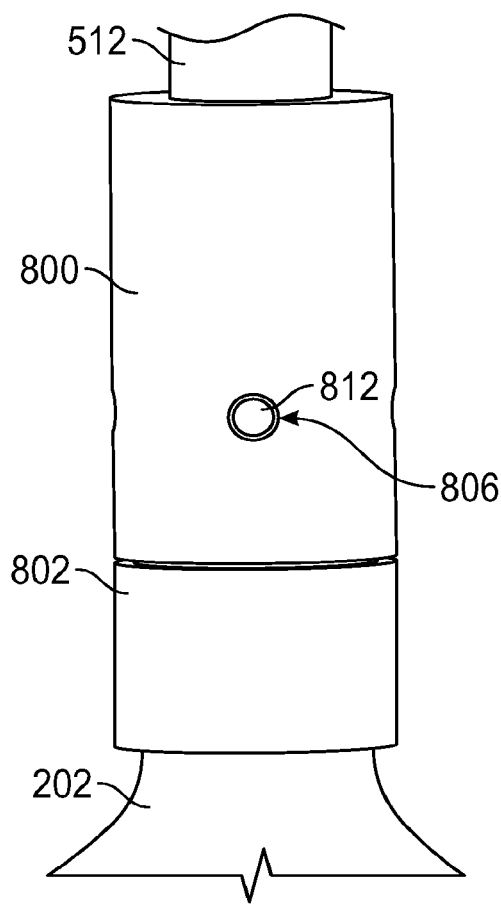
FIG. 32 illustrates other exemplary embodiments of a coupler and a proximal collar for the delivery assembly of FIG. 11, showing the coupler releasably coupled to the proximal collar.
Figure 33:
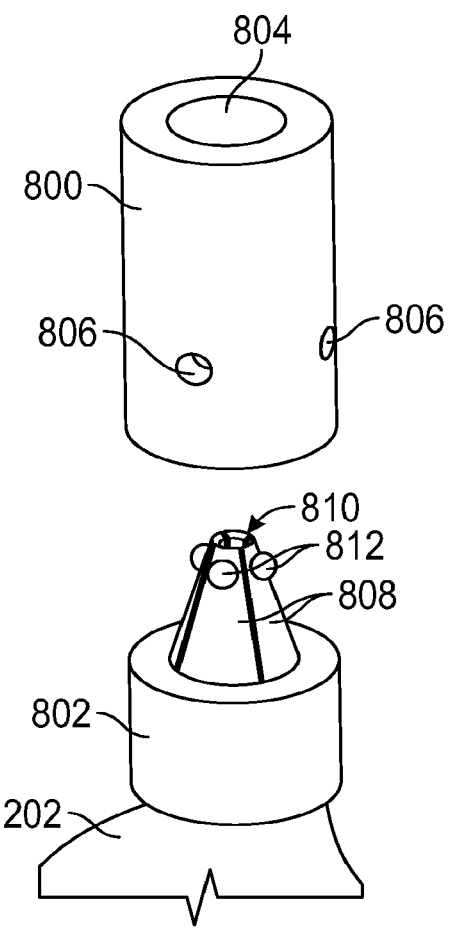
FIG. 33 is a perspective view of the coupler and proximal collar of FIG. 32, showing the coupler released from the proximal collar.

FIGS. 32-33 show exemplary embodiments of a coupler 800 and a proximal collar 802. Although not shown, the coupler 800 can be coupled to the distal end portion of the outer shaft 520 (FIG. 16) in a manner similar to the coupler 514. As shown, the proximal collar 802 can be coupled to a proximal end portion of the spacer member 202 in a manner similar to the proximal collar 210 (FIG. 13). As such, the coupler 800 and the proximal collar 802 can be used, for example, in lieu of the coupler 514 and the proximal collar 210 of the delivery assembly 500, respectively, to releasably couple the prosthetic spacer device 200 to the outer shaft 520 (FIG. 16).

Referring to FIG. 33, the coupler 800 can comprise an axially-extending lumen 804 and a plurality of radially-extending openings 806. The lumen 804 can be configured to receive the actuation shaft 512 (FIG. 32). The openings 806 can be configured to receive the proximal collar 802, as further described below.

The proximal collar 802 can comprise a plurality of proximally-extending tabs or fingers 808. Free end portions 810 of the fingers 808 can have radially-extending projections 812 formed thereon. The fingers 808 can be configured to pivot between a first or resting state (FIG. 33) and a second or deflected state (FIG. 32). In the first state, the free end portions 810 of the fingers 808 press radially inwardly against each other. In the second state, the free end portions 810 of the fingers 808 are radially spaced from each other.

Referring to FIG. 32, the coupler 800 and the proximal collar 802 be releasably coupled together by positioning the fingers 808 of the proximal collar 802 within the coupler 800. The actuation shaft 512 can then be advanced through the lumen 804 of the coupler 800 and through the fingers 808 of the proximal collar 802, thus causing the free end portions 810 of the fingers 808 to pivot radially-outwardly from the first state to the second state. The projections 812 of the fingers 808 and the openings 806 of the coupler 800 can be rotationally aligned such that the projections 812 extend into the openings 806, thereby releasably coupling the coupler 800 to the proximal collar 802. The coupler 800 can be released from the proximal collar 802 by retracting the actuation shaft 512 from the fingers 808 of the proximal collar 802. This allows the free end portions 810 of the fingers 808 to pivot from the second state back to the first state and causes the projections 812 of the fingers 808 to withdraw from the openings 806 of the coupler 800, thus releasing the coupler 800 from the proximal collar 802.

In some embodiments, the fingers 808 of the proximal collar 802 can be configured to create a hemostatic seal when the fingers 808 are in the first state. This can, for example, prevent or reduce blood from flowing through the proximal collar 802 when the prosthetic spacer device 200 is implanted in a patient.

Figure 34:
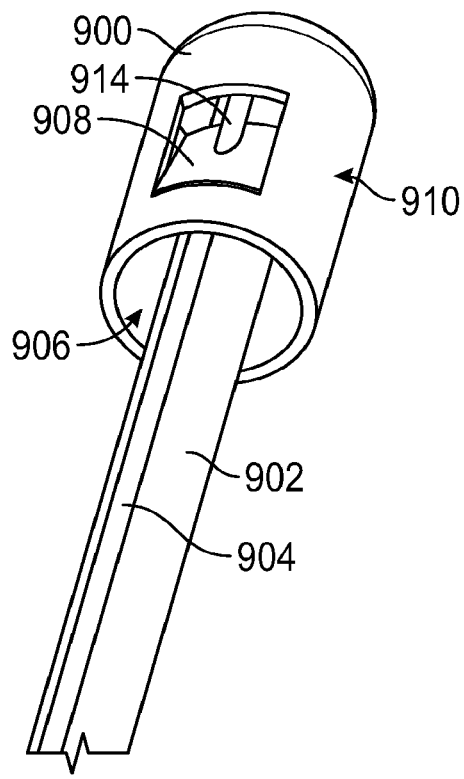
FIG. 34 illustrates other exemplary embodiments of a distal collar, actuation shaft, and release wire for the delivery assembly of FIG. 11, showing the distal collar releasably coupled to the actuation shaft by the release wire.
Figure 35:
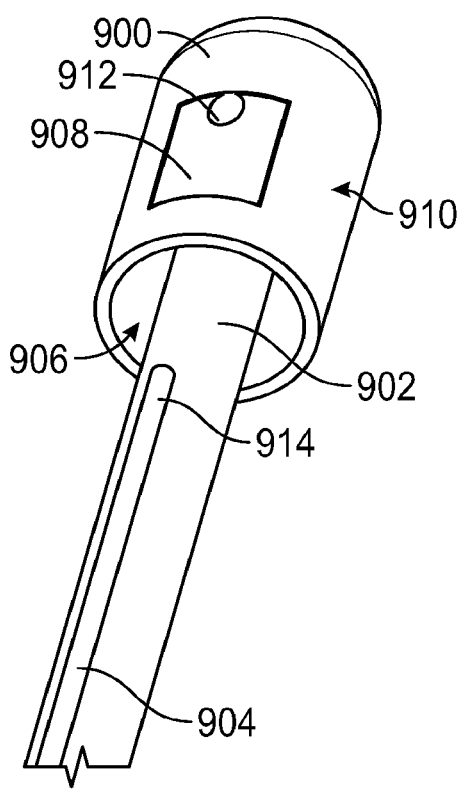
FIG. 35 is a perspective view of the distal collar, actuation shaft, and the release wire of FIG. 32, showing the distal collar released from the actuation shaft and the release wire.

FIGS. 34-35 show exemplary embodiments of a distal collar 900, an actuation shaft 902, and a release member (e.g., a wire) 904, which can be used, for example, with the delivery assembly 500. Although not shown, the distal collar 900 can be coupled to the distal end portion of the prosthetic spacer device 200. A proximal end portion (not shown) of the actuation shaft 902 can be coupled to the actuation tube 568 and the knob 526. From the proximal end portion, the actuation shaft 902 can extend distally through the handle 522 (FIG. 17), through the outer shaft 520 (FIG. 17), and into the prosthetic spacer device 200 (FIG. 12). A distal end portion of the actuation shaft 902 can be releasably coupled to the distal collar 900 of the prosthetic spacer device 200. As such, the distal collar 900 and the actuation shaft 902 can be used, for example, in lieu of the distal collar 208 and the actuation shaft 512 of the delivery assembly 500, respectively.

Referring to FIG. 35, the distal collar 900 can comprise a central bore 906 and a tab or tongue 908 formed (e.g., laser cut) in a side surface 910 of the distal collar 900. The tongue 908 can have an opening 912 formed (e.g., laser cut) therein.

The central bore 906 can be configured to receive a distal end portion of the actuation shaft 902. The tongue 908 can be pivotable relative to the side surface 910 of the distal collar 900 from a first or resting configuration (FIG. 35) to a second or deflected configuration (FIG. 34). In the first configuration, the tongue 908 can be flush with the side surface 910. In the second configuration, the tongue 908 can extend radially inwardly relative to the side surface 910 so as to protrude into the central bore 906. The tongue 908 can be biased (e.g., shaped set) toward the first configuration.

The tongue 908 can be used, for example, to releasably couple the distal collar 900 to the actuation shaft 902, as shown in FIG. 34. For example, the actuation shaft 902 can be inserted into the central bore 906 of the distal collar 900. The tongue 908 can then be pushed radially inwardly from the first configuration to the second configuration such that the tongue 908 presses against the actuation shaft 902 and frictionally retains the actuation shaft 902 relative to the collar 900. The release member 904 can then be advanced distally such that a distal end portion 914 of the release member 904 extends through the opening 912 of the tongue 908. Thus, the release member 904 retains the tongue 908 in the second configuration against the actuation shaft 902, thereby releasably coupling the distal collar 900 to the actuation shaft 902.

The distal collar 900 can be released from the actuation shaft 902 by retracting the release member 904 proximally such that the distal end portion 914 of the release member 904 withdraws from the opening 912 of the tongue 908. This allows the tongue to move radially outwardly from the second state back to the first state, thereby releasing the distal collar 900 from the actuation shaft 902.

This configuration can provide several advantages. For example, in some embodiments, the distal collar 900 and the actuation shaft 902 can be formed without threads. Removing the threads can make manufacturing the distal collar 900 and the actuation shaft 902 easier and/or less expensive. Removing the threads from the actuation shaft 902 can also reduce the likelihood the actuation shaft 902 could catch or snag on another component of the delivery assembly 500.

Figure 36:
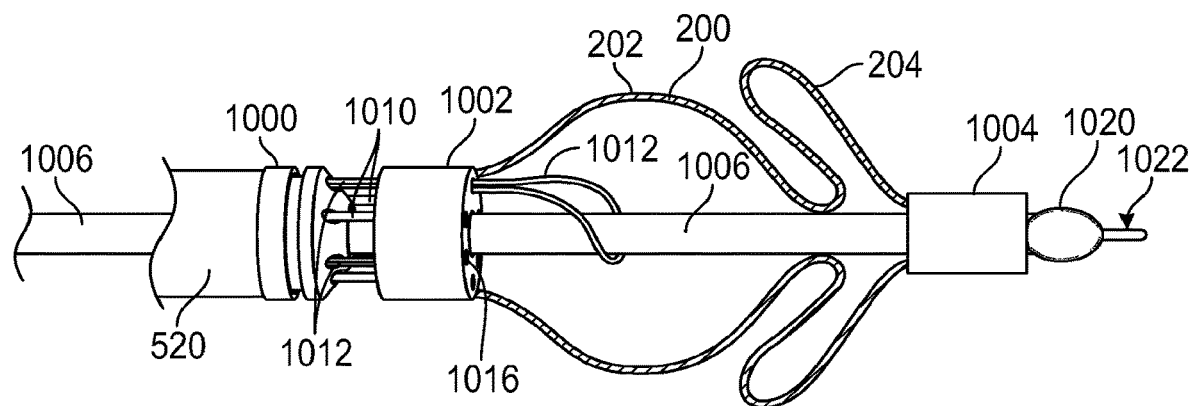
FIG. 36 illustrates other exemplary embodiments of a coupler, a proximal collar, a distal collar, and an actuation shaft of the delivery assembly of FIG. 11.
Figure 37:
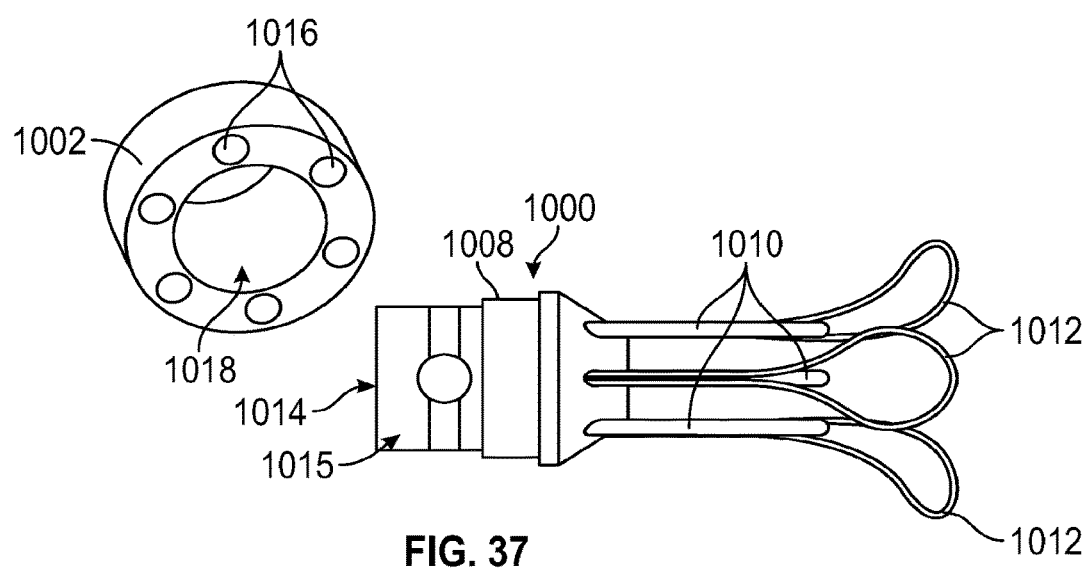
FIG. 37 is a perspective view of the coupler and proximal collar of FIG. 36.

FIGS. 36-37 show exemplary embodiments of a coupler 1000, a proximal collar 1002, a distal collar 1004, and an actuation shaft 1006, which can be used, for example, with the delivery assembly 500. Referring to FIG. 36, the coupler 1000 can be coupled to the distal end portion of the outer shaft 520. The proximal collar 1002 can be coupled to the proximal end portion of the prosthetic spacer device 200 (shown schematically in partial cross-section), and the distal collar 1004 can be coupled to the to the distal end portion of the prosthetic spacer device 200. A proximal end portion (not shown) of the actuation shaft 1006 can be coupled to the actuation tube 568 and the knob 526. From the proximal end portion, the actuation shaft 1006 can extend distally through the handle 522 (FIG. 17), through the outer shaft 520 (FIG. 17), and into the prosthetic spacer device 200 (FIG. 12). A distal end portion of the actuation shaft 1006 can be releasably coupled to the distal collar 1004 of the prosthetic spacer device 200. As such, the coupler 1000, the proximal collar 1002, the distal collar 1004, and the actuation shaft 1006 can be used, for example, in lieu of the coupler 514, the proximal collar 210, the distal collar 208, and the actuation shaft 512 of the delivery assembly 500, respectively.

Referring to FIG. 37, the coupler 1000 can comprise a connection portion 1008, a plurality of pins 1010 (e.g., three in the illustrated embodiment), and one or more securing members 1012 (e.g., three in the illustrated embodiment). The pins 1010 and the securing members can be coupled to and extend distally from the connection portion 1008.

The connection portion 1008 can have an axially-extending lumen 1014 configured to slidably receive the actuation shaft 1006. In some embodiments, the connection portion 1008 can also have a recessed outwardly facing surface 1015 (FIG. 37) configured to be inserted into the distal end portion of the outer shaft 520, as shown in FIG. 36.

As best shown in FIG. 37, the pins 1010 can be spaced circumferentially relative to each other and relative to the securing members 1012. The securing members 1012 can be spaced circumferentially relative to each other. In some embodiments, the pins 1010 and the securing members 1012 can be arranged in an alternating type pattern (e.g., pin-securing member-pin and so on) on the connection portion 1008.

Referring to FIG. 36, the pins 1010 can be configured to extend into openings 1016 of the proximal collar 1002. In certain embodiments, the securing members 1012 can be suture loops. The securing members 1012 can be configured to extend through the openings 1016 of the proximal collar 1002 and around the actuation shaft 1006. For clarity, only one securing member 1012 is shown extending around the actuation shaft 1006 in FIG. 36.

Referring again to FIG. 37, in addition to the openings 1016, the proximal collar 1002 can comprise a central lumen 1018 disposed radially inward from the openings 1016. The central lumen 1018 can extend axially and can be configured to slidably receive the actuation shaft 1006, as shown in FIG. 36.

The distal collar 1004 can be configured in a sleeve-like manner such that the actuation shaft 1006 can slidably extend through the distal collar 1004, as shown in FIG. 36.

The actuation shaft 1006 can comprise a radially-expandable portion 1020 disposed at or near the distal end portion 1022 of the actuation shaft 1006. The radially-expandable portion 1020 can be configured to be selectively expandable from a compressed configuration to an expanded configuration. For example, the radially-expandable portion 1020 can be an inflatable balloon or an expandable mesh (e.g., braided) basket.

The radially-expandable portion 1020 can be configured such that an outside diameter of the radially-expandable portion 1020 is less than the inside diameter of the distal collar 1004, the central lumen 1018 of the proximal collar 1002, and the lumen 1014 of the coupler 1000 when the radially-expandable portion 1020 is in the compressed configuration. When the radially-expandable portion 1020 is in the expanded configuration, the outside diameter of the radially-expandable portion 1020 is greater than the inside diameter of the distal collar 1004. Thus, in the expanded configuration, the radially-expandable portion 1020 can prevent the distal end portion 1022 from moving proximally relative to the distal collar 1004.

As shown in FIG. 36, the prosthetic spacer device 200 can be releasably coupled to the outer shaft 520 and the actuation shaft 1006 by inserting the pins 1010 and the securing members 1012 through respective openings 1016 in the proximal collar 1002. With the radially-expandable portion 1020 in the compressed configuration, the actuation shaft 1006 can be advanced distally through the lumen 1014 of the coupler 1000, through the central lumen 1018 and the securing members 1012 of the proximal collar 1002, and through the distal collar 1004 such that the radially-expandable portion 1020 is disposed distal relative to the distal collar 1004. The radially-expandable portion 1020 of the actuation shaft 1006 can then be expanded from the compressed configuration to the expanded configuration, thus releasably coupling the prosthetic spacer device 200 to the outer shaft 520 and the actuation shaft 1006.

The prosthetic spacer device 200 can be released from the outer shaft 520 and the actuation shaft 1006 by compressing the radially-expandable portion 1020 of the actuation shaft 1006 and proximally retracting the actuation shaft 1006 through the distal collar 1004, through the securing members 1012 and the central lumen 1018 of the proximal collar 1002. The outer shaft 520 can then be retracted proximally relative to the prosthetic spacer device 200 such that the pins 1010 and the securing members 1012 withdraw from the openings 1016 in the proximal collar 1002, thus releasing the prosthetic spacer device 200 from the outer shaft 520 and the actuation shaft 1006.

Figure 38:
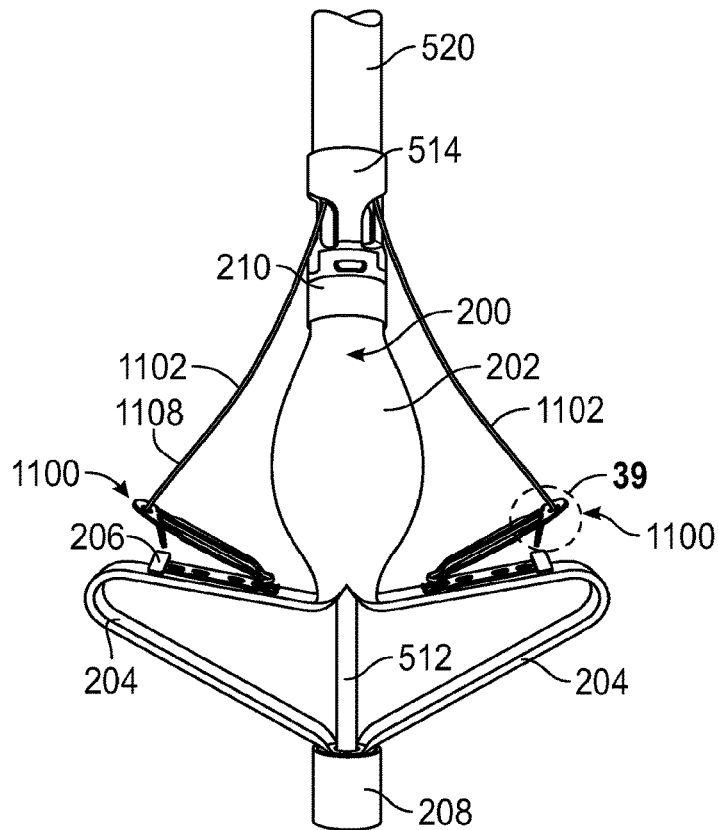
FIG. 38 illustrates another exemplary embodiment of a clasp control member of the delivery apparatus of FIG. 11.
Figure 39:
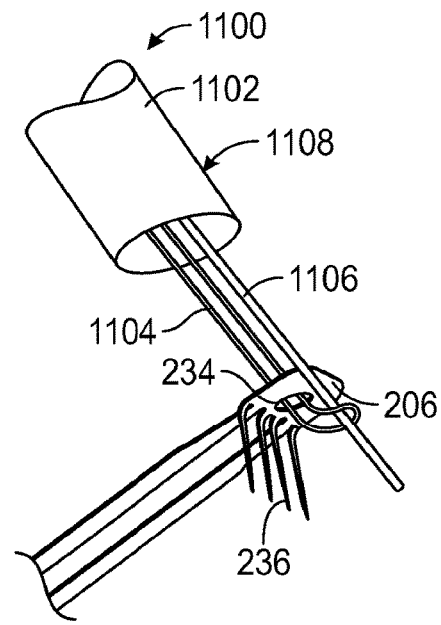
FIG. 39 is a detail view of the clasp control member of FIG. 38, taken from the perspective 39 shown in FIG. 38.

FIGS. 38-39 show an exemplary embodiment of clasp control members 1100, which can be used, for example, in lieu of the clasp control members 524 of the delivery assembly 500. Referring to FIG. 39, the clasp control members 1100 can comprise sleeves 1102, connecting members 1104, and release members 1106. The connecting members 1104 and the release members 1106 can extend axially through and can be movable relative to the sleeves 1102.

Proximal end portions (not shown) of the sleeves 1102 can be coupled to the control member tubes 570, and distal end portions of the sleeves 1108 can be releasably coupled to the clasps 206 of the prosthetic spacer device 200 by the connecting members 1104 and the release members 1106, as further described below.

The connecting members 1104 can, for example, be suture loops that extend distally from the clasp control mechanism 550 of the delivery apparatus 502, through the control member tubes 570, through the sleeves 1102, and through the openings 234 of the clasps 206. The connecting members 1104 can be releasably coupled to the clasps 206 the prosthetic spacer device 200 by the release members 1106.

The release members 1106 can, for example, be wires that extend distally from the clasp control mechanism 550 of the delivery apparatus 502, through the control member tubes 570, through the sleeves 1102, and through the loops of the connecting members 1104. In this manner, the release members 1106 releasably couple the connecting members 1104 and thus the sleeves 1102 to the clasps 206 by preventing the connecting members 1104 from withdrawing through the openings 234 of the clasps 206. The connecting members 1104 can be released from the clasps 206 by withdrawing the release members 1106 from the loops of the connecting members 1104 and withdrawing the connecting members 1104 from the openings 234 of the clasps 206.

With the sleeves 1102 releasably coupled to the clasps 206 of the prosthetic spacer device 200 by the connecting members 1104 and the release members 1106, the clasps 206 can be actuated (either together or separately) by moving the sleeves 1102 axially relative to the outer shaft 520 and the actuation shaft 512. This can be accomplished, for example, by moving the actuator member 590, which are coupled to the sleeves 1102 via the control member tubes 570, relative to the housing 546 and actuation tube 568. Moving the actuator member 590 proximally relative to the housing 546 and actuation tube 568 can open the clasps 206, and moving the actuator member 590 distally relative to the housing 546 and actuation tube 568 can close the clasps 206.

Because the sleeves 1102 are relatively rigid (e.g., compared to the clasp control members 524), the sleeves 1102 can be used to push the clasps 206 closed (either in lieu of or in addition to the bias of the clasps 206 to the closed position). This pushability can help to ensure the native leaflets are captured within the clasps 206 and thus secured to the anchors 204.

Figure 40:
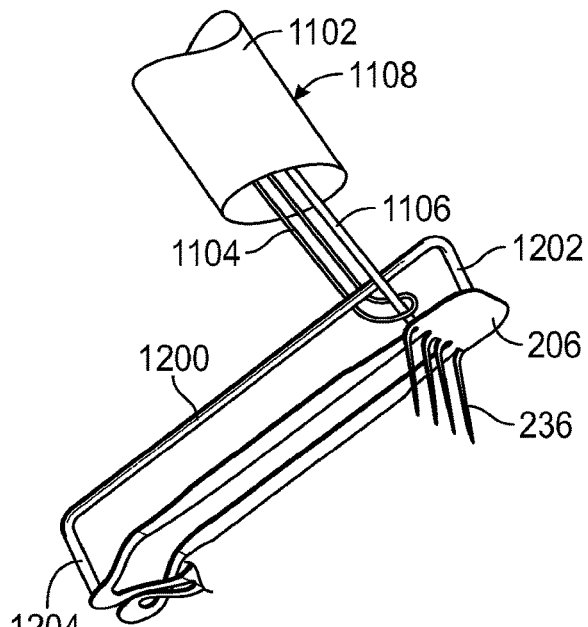
FIG. 40 illustrates an exemplary embodiment of a guide rail for the clasp control member of FIG. 38.

FIG. 40 shows an exemplary embodiment of a guide rail 1200. The guide rail 1200 can, for example, be coupled to a respective clasp 206 of the prosthetic spacer device 200. In some embodiments, the clasp control member 1100 can be releasably coupled to the guide rail 1200 in a snare-like manner similar to that described above with respect to FIG. 39.

Coupling the clasp control member 1100 to the guide rail 1200 rather than directly to the clasps 206 allows the clasp control member 1100 to slide longitudinally along the guide rail 1200 as the clasp 206 moves between the open and the closed configurations. This can, for example, allow the clasp control member 1100 to maintain a relatively constant angle relative to the anchors 204 as the clasps 206 are actuated. For example, the clasp control member 1100 can slide outwardly toward a first side portion 1202 of the guide rail 1200 when the clasp 206 is pulled open, and the clasp control member 1100 can slide inwardly toward a second side portion 1204 of the guide rail 1200 when the clasp 206 is pushed closed. This can therefore reduce the force required to actuate the clasp control member 1100.

Figure 41:
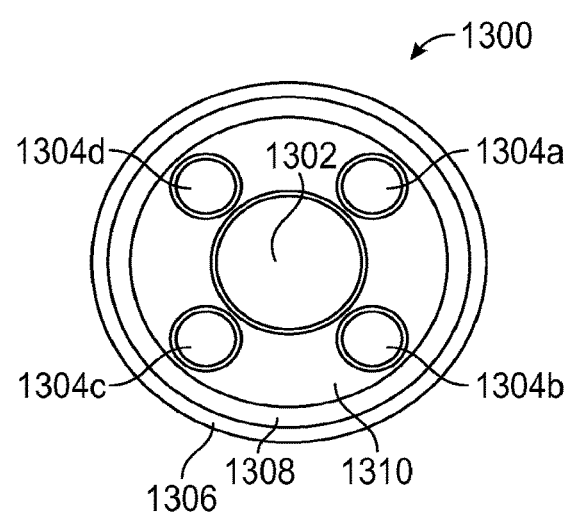
FIG. 41 illustrates another exemplary embodiment of a shaft of the delivery apparatus of FIG. 11.

FIG. 41 shows an exemplary embodiment of a shaft 1300. The shaft 1300 can be used, for example, with the delivery apparatus 502 in lieu of the outer shaft 520 of the third catheter 508. The shaft 1300 can comprise a plurality of axially extending lumens, including an actuation shaft lumen 1302 and a plurality of control member lumens 1304 (e.g., four in the illustrated embodiment 1304a, 1304b, 1304c, 1304d—collectively referred to as "the control member lumens 1304") disposed radially outwardly from the actuation shaft lumen 1302. The control member lumens 1304 can be spaced relative to each other and can be evenly distributed circumferentially around the actuation shaft lumen 1302. For example, each of the control member lumens 1304 can be located approximately 90 degrees from an adjacent control member lumen 1304.

The actuation shaft lumen 1302 can be configured to receive the actuation shaft 512, and the control member lumens 1304 can be configured to receive the clasp control members 524. The lumens 1302, 1304 can also be configured such that the actuation shaft 512 and clasp control members 524 can be movable (e.g., axially and/or rotationally) relative to the lumens 1302, 1304, respectively. In particular embodiments, the lumens 1302, 1304 can comprise a liner or coating (e.g., PTFE) configured to reduce friction between the lumens 1302, 1304 and the actuation shaft 512 and clasp control members 524, respectively.

Each of the clasp control members 524 can extend through one or more of the control member lumens 1304 and extend around a clasp 206 of the prosthetic spacer device 200. For example, in some embodiments, each clasp control member 524 can extend through a pair of control member lumens 1304 that are circumferentially offset by 90 degrees.

In one particular embodiment, a first clasp control member 524 can extend through the lumens 1304a, 1304b and around a first clasp 206 of the prosthetic spacer device 200, and a second clasp control member 524 can extend through the lumens 1304c, 1304d and around a second clasp 206 of the prosthetic spacer device 200.

In such embodiments, when the shaft 1300 is deflected in a direction oriented between two lumens corresponding to one of clasp control members 524 (e.g., to the right as illustrated in FIG. 41), the lumens 1304a, 1304b both foreshorten because they are on the inner diameter of the curve, and the lumens 1304c, 1304d both elongate because they are on the outer diameter of the curve. Because the clasp control members 524 are free to move axially within the lumens 1304, the tension of the first clasp control member 524 (which is disposed on the inner diameter of the curve) is reduced and thus the first clasp 206 can move slightly toward the closed configuration due to the bias of the claps; whereas, the tension of the second clasp control member 524 (which is disposed on the outer diameter of the curve) is increased and thus the second clasp 206 can move slightly toward the open configuration. When the shaft 1300 is rotated 180 degrees, the lumens 1304a, 1304b and the first clasp control member 524 move from the inner diameter of the curve to the outer diameter of the curve, thus increasing tension and slightly opening the first clasp 206, and the lumens 1304c, 1304d and the second clasp control member 524 move from the outer diameter of the bend to the inner diameter of the bend, thus reducing tension and slightly closing the clasp 206.

In other embodiments, the first clasp control member 524 can extend through the lumen 1304a, extend around the first clasp 206, and extend through the lumen 1304c. The second clasp control member 524 can extend through the lumen 1304b, extend around the second clasp 206, and extend through the lumen 1304d. Threading each clasp control member 524 through a pair of control member lumens 1304 that are circumferentially offset by 180 degrees can provide several advantages. For example, this configuration allows the clasp control members 524 to maintain uniform tension on the clasps 206 as the shaft 1300 is deflected and/or rotated (e.g., during positioning of the prosthetic spacer device 200). This is because a length in which each lumen 1304 foreshortens/elongates when the shaft 1300 is deflected and/or rotated is offset by an equal and opposite length in which a respective, diametrically-opposite lumen 1304 elongates/foreshortens and because the clasp control members 524 can move relative to the lumens 1304 and the clasps 206 as the lumens 1304 foreshorten/elongate. The clasps 206 of the prosthetic spacer device 200 therefore maintain their open and/or closed configuration regardless of the deflection and/or rotation of the shaft 1300.

The shaft 1300 can be formed from various materials, including metals and polymers. For example, in one particular embodiment, the shaft 1300 can comprise a first portion or layer 1306, a second portion or layer 1308, and a third portion or layer 1310. The first portion 1306 be the radially outermost portion, the third portion 1310 can be the radially innermost portion, and the second portion 1308 can be disposed radially between the first and third portions 1306, 1310. In certain embodiments, the first and third portions 1306, 1310 can be formed from polymeric material (e.g., PEBA having a Type D Shore durometer value of 55D), and the second portion 1308 can be formed from a metallic material (e.g., braided stainless steel).

Configuring the shaft 1300 in this manner can, for example, further improve control of the distal end portion of the shaft 1300. For example, this configuration can prevent or reduce "whipping" (e.g., sudden or abrupt movement) at the distal end portion of the shaft 1300 when the shaft 1300 is rotated at the proximal end portion (e.g., by rotating the housing 546 of the handle 522). As such, a physician can more precisely control of the distal end portion of the shaft 1300 and thus of a prosthetic spacer device (e.g., the prosthetic spacer device 200) during the implantation procedure such as when the physician rotates the prosthetic spacer device to align the anchors of the prosthetic spacer device with the native leaflets.

It should be noted that in certain embodiments the housing 546 of the handle 522 can comprise four control member lumens 564, 582 (i.e., four of each) that are coupled to the control member lumens 1304. As such, each longitudinally-extending section of each clasp control member 524 can extend distally in a separate lumen from the clasp control mechanism 550 of the handle 522 to the prosthetic spacer device 200.

Figure 42:
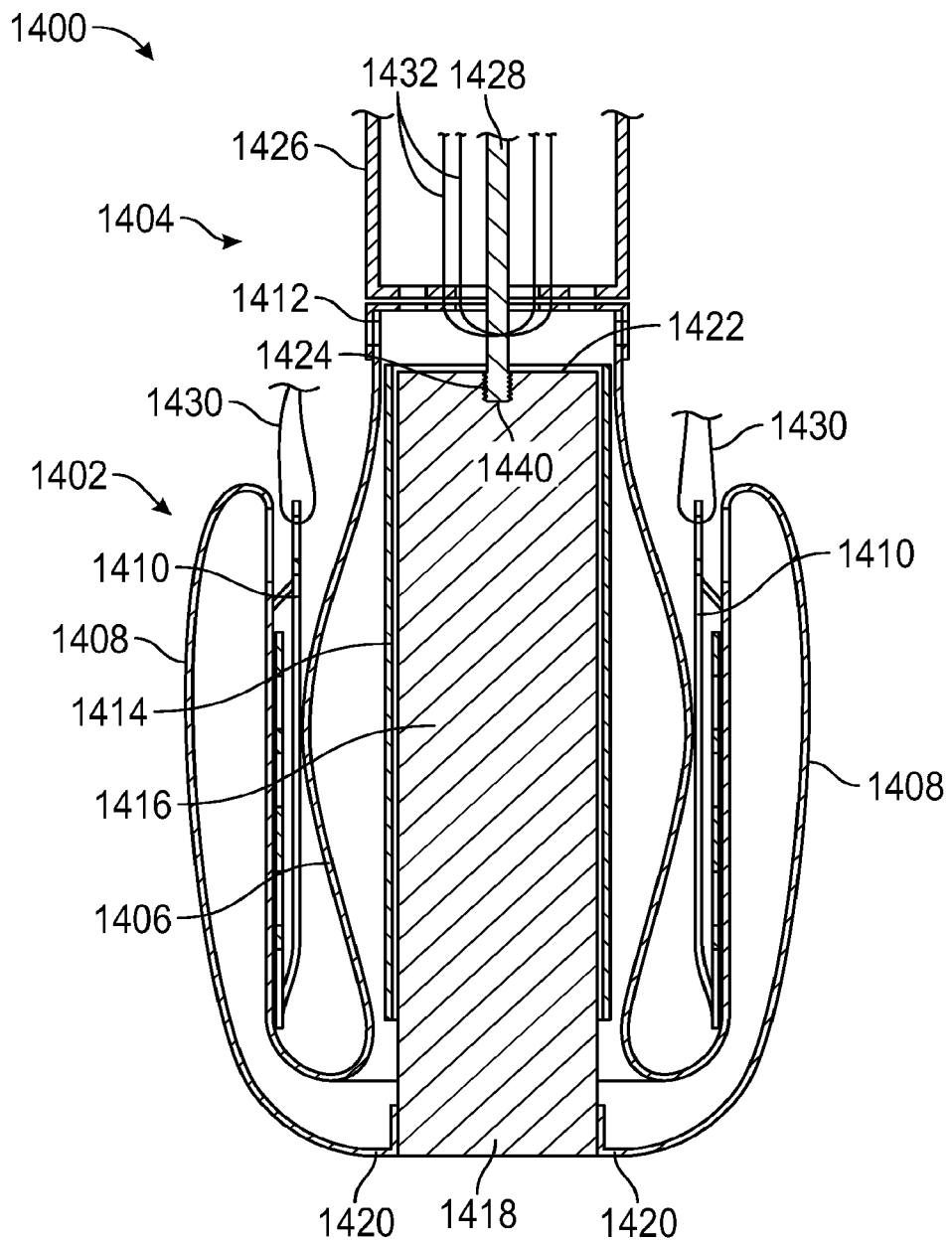
FIGS. 42-45 illustrate another exemplary delivery assembly and its components.
Figure 43:
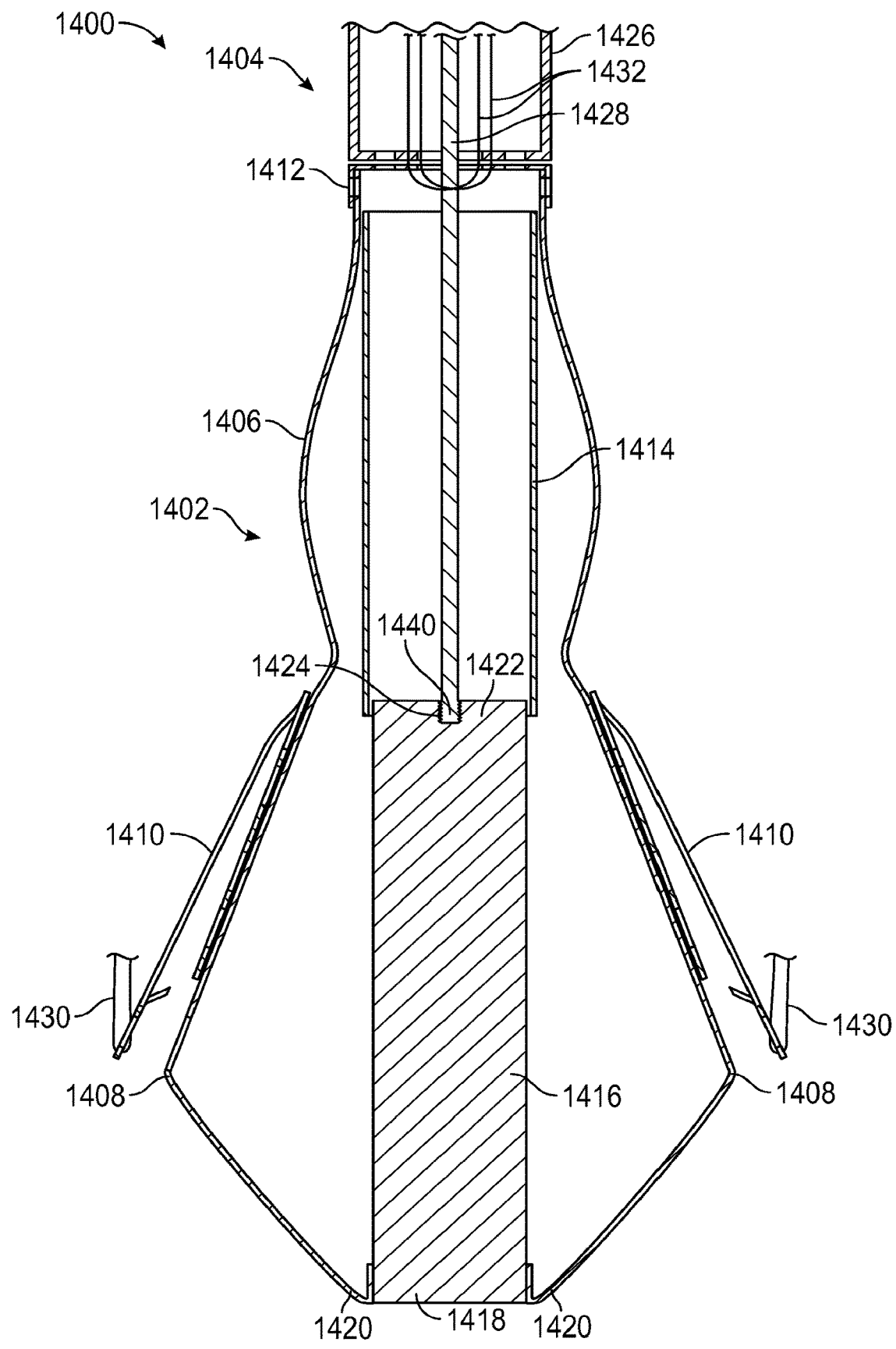
Figure 44:
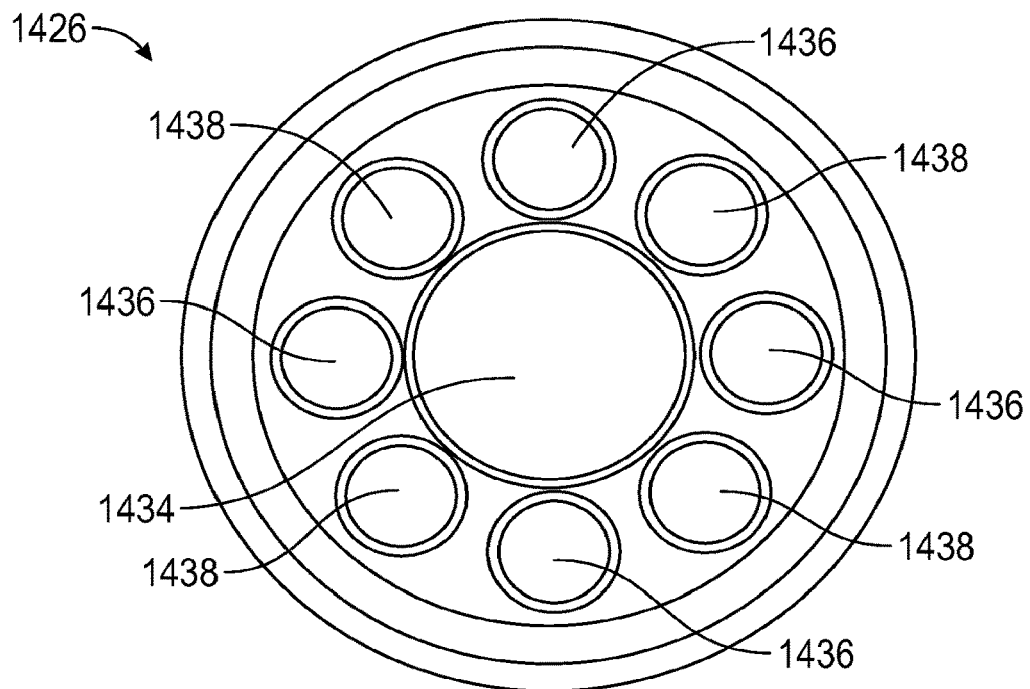
Figure 45:
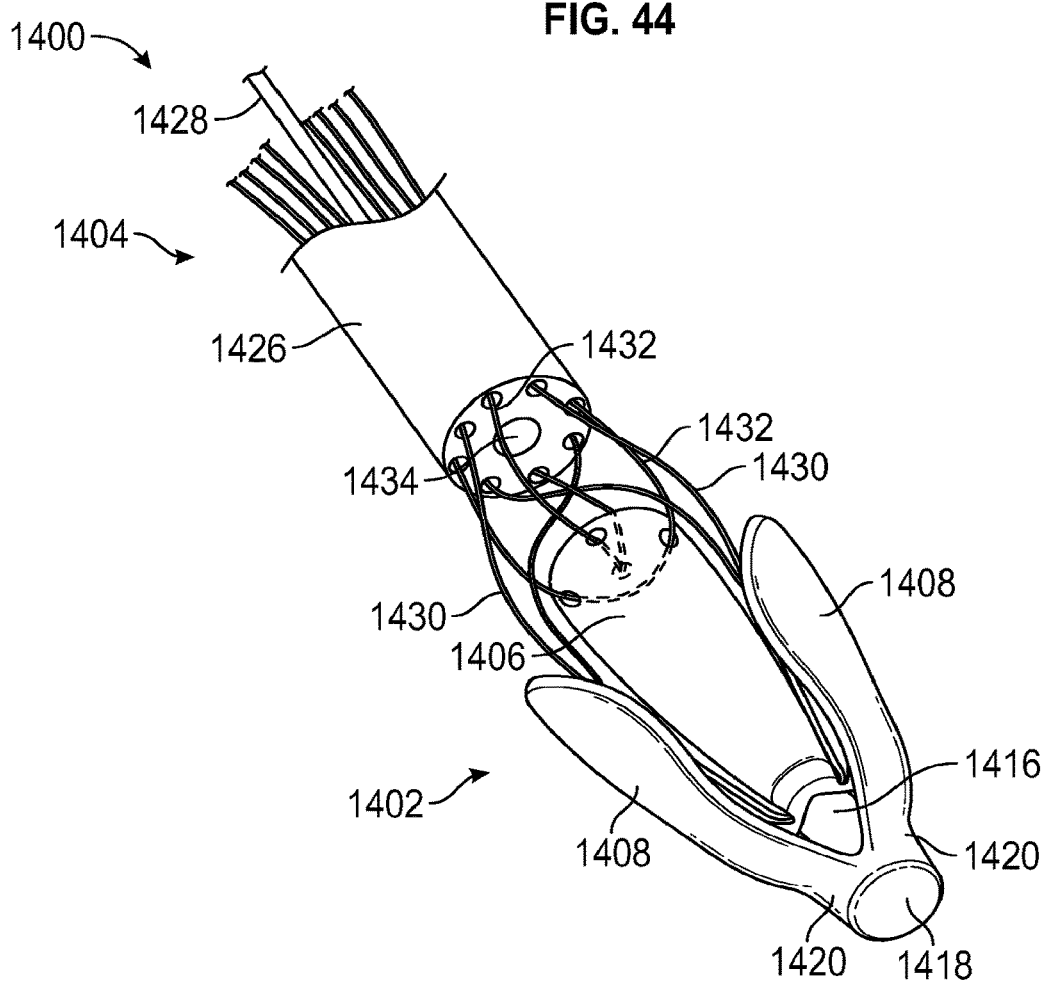

FIGS. 42-45 show an exemplary delivery assembly 1400 comprising a prosthetic spacer device 1402 and a delivery apparatus 1404. The prosthetic spacer device 1402 can be configured to reduce or prevent regurgitation through a native heart valve (e.g., a native mitral valve). As shown in FIGS. 42-43 and 45, the prosthetic spacer device 1402 can be releasably coupled to the delivery apparatus 1404, which can be used to implant the prosthetic spacer device.

Referring to FIG. 42, the prosthetic spacer device 1402 can comprise a spacer member 1406, a plurality of anchors 1408, and a plurality of clasps 1410. In some embodiments, the spacer member 1406, the anchors 1408, and the clasps 1410 can be configured in a manner similar to the spacer member 202, the anchors 204, and the clasps 206 of the prosthetic spacer device 200, respectively.

The prosthetic spacer device 1400 can also comprise a proximal collar 1412, a sleeve or cylinder 1414, and a piston 1416. The proximal collar 1412 and the cylinder 1414 can be coupled to the spacer member 1406, and the piston 1416 can be coupled to the anchors 1408.

The proximal collar 1412 can be coupled to and extend annularly around the proximal end portion (i.e., the upper end portion as illustrated) of the spacer member 1406. The proximal collar 1412 can be used, for example, for coupling the prosthetic spacer device 1400 to the delivery apparatus 1404, as further described below. In some embodiments, the proximal collar 1412 can have connector members for receiving tethers 1432 of the delivery apparatus 1404. The connector members can, for example, include openings, eyelets, and/or other suitable means for connecting the tethers to the proximal collar 1412.

The cylinder 1414 can be coupled to and extend coaxially through at least a portion of the spacer member 1406. The cylinder 1414 can be coupled to the spacer member 1406 in various ways such as with fasteners, sutures, adhesive, welding, and/or other means for coupling. The cylinder 1414 can be sized and configured such the piston 1416 can move axially through the cylinder 1414. As such, the cylinder 1414 can be used, for example, as a guide for the piston 1416 as the prosthetic spacer device 1400 is moved between various configurations such as a foreshortened/functional configuration (e.g., FIG. 42) and an elongate/delivery configuration (e.g., FIG. 43).

The distal end portion 1418 of the piston 1416 can be coupled to distal end portions 1420 of the anchors 1408. This can be accomplished in various ways such as with fasteners, sutures, adhesive, welding, and/or other coupling means. The proximal end portion 1422 of the piston 1416 can be coupled to the delivery apparatus 1404. For example, in some embodiments, the proximal end portion 1422 of the piston 1416 can comprise a bore or opening 1424 having internal threads configured to receive corresponding external threads of an actuation shaft 1428 of the delivery apparatus 1404. The piston 1416 (in combination with the delivery apparatus) can be used, for example, to move the anchors 1408 between various configurations such as a folded/functional configuration (e.g., FIG. 42) and a straight/delivery configuration (e.g., FIG. 43).

The delivery apparatus 1400 can comprise an implant catheter (e.g., similar to the third catheter 508 of the delivery apparatus 502) having an outer shaft 1426, an actuation shaft 1428, a plurality of clasp control members 1430, and a plurality of tethers 1432. The outer shaft 1426 can be used, for example, to position the prosthetic spacer device 1402 during the implantation procedure of the prosthetic spacer device 1402. The actuation shaft 1428 can be used, for example, to move the prosthetic spacer device 1402 between the functional configuration (FIG. 42) and the delivery configuration (e.g., FIG. 43). The clasp control members 1430 can be used, for example, to move the clasps 1410 between an open configuration and a closed configuration. The tethers 1432 can be used, for example, to couple the prosthetic spacer device 1402 to the outer shaft 1426.

Referring to FIG. 44, the outer shaft 1426 can comprise a plurality of lumens, including an actuation shaft lumen 1434, a plurality of control member lumens 1436, and a plurality of tether lumens 1438. The outer shaft 1426 can otherwise be configured similar to the outer shaft 520 and/or the shaft 1300.

Referring again to FIG. 42, the actuation shaft 1428 can be configured similar to the actuation shaft 512. In some embodiments, the distal end portion of the actuation shaft 1428 can comprise external threads 1440 configured to threadably mate with the internal threads of the opening 1424 in the proximal end portion 1422 of the piston 1416.

In other embodiments, the actuation shaft 1428 can be coupled to the anchors 1408 of the prosthetic spacer device 1402 in various other ways. Although not shown, the prosthetic spacer device 1402 can, for example, include a distal collar that is configured similar to the distal collars 108, 208, 900, and/or 1004 in lieu of or in addition to the piston 1416, and the actuation shaft 1428 can be configured similar to the actuation shafts 512, 902, and/or 1006.

The clasp control members 1430 can be configured similar to the clasp control members 524 of the delivery apparatus 502. The clasp control members 1430 can extend through the control member lumens 1436 of the outer shaft 1426 and around the clasps 1410 of the prosthetic spacer device 1402. Tensioning the clasp control members 1430 can move the clasps 1410 to the open configuration. Slackening the clasp control members 1430 can allow the clasps 1410 to move to the closed configuration (due to bias of the clasp 1410 toward the closed configuration).

In some embodiments, each of the clasp control members 1430 can extend through two of the control member lumens 1436 of the outer shaft 1426. In certain embodiments, each clasp control member 1430 can extend through two control member lumens 1436 that are circumferentially offset from each other by 180 degrees similar to the manner described above with respect to the shaft 1300.

The tethers 1432 can extend through the tether lumens 1438 of the outer shaft 1426 and around the proximal end (e.g., through the proximal collar 1412) of the prosthetic spacer device 1402. Tensioning the tethers 1432 can draw the proximal end portion of the prosthetic spacer device 1402 toward the distal end portion of the outer shaft 1426 (e.g., FIGS. 42-43. Slackening the tethers 1432 can allow the proximal end portion of the prosthetic spacer device 1402 to separate from the distal end portion of the outer shaft 1426 (e.g., FIG. 45).

In some embodiments, each of the tethers 1432 can extend through two of the tether lumens 1438 of the outer shaft 1426. In certain embodiments, each tether 1432 can extend through two tether lumens 1438 that are circumferentially offset from each other by 180 degrees.

With prosthetic spacer device 1402 coupled to the delivery apparatus 1404 by the outer shaft 1426 (via the tethers 1432), the actuation shaft 1428, and the clasp control members 1430, the delivery assembly 1400 can be used, for example, to implant the prosthetic spacer device 1402 in a native heart valve of a patient's heart. This can be accomplished, for example, by advancing the prosthetic spacer device 1402 through the first and second catheters 504, 506 of the delivery apparatus 502 into the patient's heart with the prosthetic spacer device 1402 in the delivery configuration (e.g., FIG. 43). The prosthetic spacer device 1402 can be advanced out of the distal ends of the first and second catheters 504, 506. The prosthetic spacer device 1402 can then be moved from the delivery configuration to the functional configuration (e.g., FIG. 42) by moving the actuation shaft 1428 proximally relative to the outer shaft 1426 such that the piston 1416 moves through the cylinder 1414 and the proximal end portion 1422 of the piston 1416 is disposed adjacent the proximal collar 1412.

The actuation shaft 1428 and/or the clasp control members 1430 of the delivery apparatus 1404 can be actuated to capture the native heart valve leaflets with the clasps 1410, and the native leaflets can be secured against the spacer member 1406. This can be performed in a manner similar to that described above with respect the delivery assembly 500 and shown in FIGS. 22-25.

With the prosthetic spacer device 1402 secured to the native leaflets, the functionality and/or positioning of the prosthetic spacer device 1402 can be evaluated. To evaluate, the physician can, for example, release the actuation shaft 1428 from the piston 1416 and move the actuation shaft proximally such that the distal end portion of the actuation shaft is disposed within the central lumen 1434 of the outer shaft 1426. The clasp control members 1430 and the tethers 1432 can be slackened such that the outer shaft 1426 can be retracted away from the proximal end portion of the prosthetic spacer device 1402 so that the distal end of the shaft 1426 is spaced from the prosthetic spacer device 1402. In this manner, the prosthetic spacer device 1402 is partially released from the delivery apparatus 1400, but the clasp control members 1430 and the tethers 1432 remain coupled to the prosthetic spacer device 1402. Due to the flexibility and slack of the clasp control members 1430 and the tethers 1432, the prosthetic spacer device 1402 can move and/or function as if it were fully released from the delivery apparatus 1404. As a result, the partially released configuration can, for example, allow the physician to better evaluate the functionality and/or positioning of the prosthetic spacer device 1402 prior to fully releasing the prosthetic spacer device 1402 than when evaluating the prosthetic spacer device 1402 while it is connected to the outer shaft 1426 and/or the actuation shaft 1428. This is because the outer shaft 1426 and/or the actuation shaft 1428 are relatively more rigid than the clasp control members 1430 and the tethers 1432, and can thus alter the position and/or hemodynamics of the prosthetic spacer device 1402 compared to when the prosthetic spacer device 1402 is partially or fully released from the delivery apparatus 1404.

If the physician would like to adjust the positioning of the prosthetic spacer device 1402, the tethers 1432 can be tightened and the distal end portion of the outer shaft 1426 can be advanced distally over the tethers 1432 such that it abuts the proximal end portion of the prosthetic spacer device 1402. The actuation shaft 1428 can be advanced distally through the central lumen 1434 of the outer shaft 1426 and reconnected to the proximal end portion 1422 of the piston 1416. The prosthetic spacer device 1402 can then be moved/repositioned relative to the native leaflets by actuating the actuation shaft 1428 and/or the clasps control members 1430 to manipulate the anchors 1408 and/or the clasps 1410, respectively. The physician can then re-evaluate the positioning and/or functionality of the prosthetic spacer device 1402 and, if desired, make additional adjustments.

From the partially released configuration, the prosthetic spacer device 1402 can be fully released from the delivery apparatus 1404 by withdrawing the clasp control members 1430 from the clasps 1410 of the prosthetic spacer device 1402 and by withdrawing the tethers 1432 from proximal end portion of the prosthetic spacer device 1402. The clasp control members 1430 and the tethers 1432 can then be retracted proximally into the lumens 1436, 1438 of the outer shaft 1426, and the outer shaft together with the actuation shaft 1428 can be retracted proximally through the first and second catheters 504, 506 and removed from the patient's body.

The tethers 1432 can be incorporated into any of the embodiments disclosed herein to allow a prosthetic implant to be implanted while still tethered to the delivery apparatus to evaluate the operation of the implant, and then fully release the implant from the delivery apparatus once the operation of the implant is confirmed by the practitioner.

Figure 46:
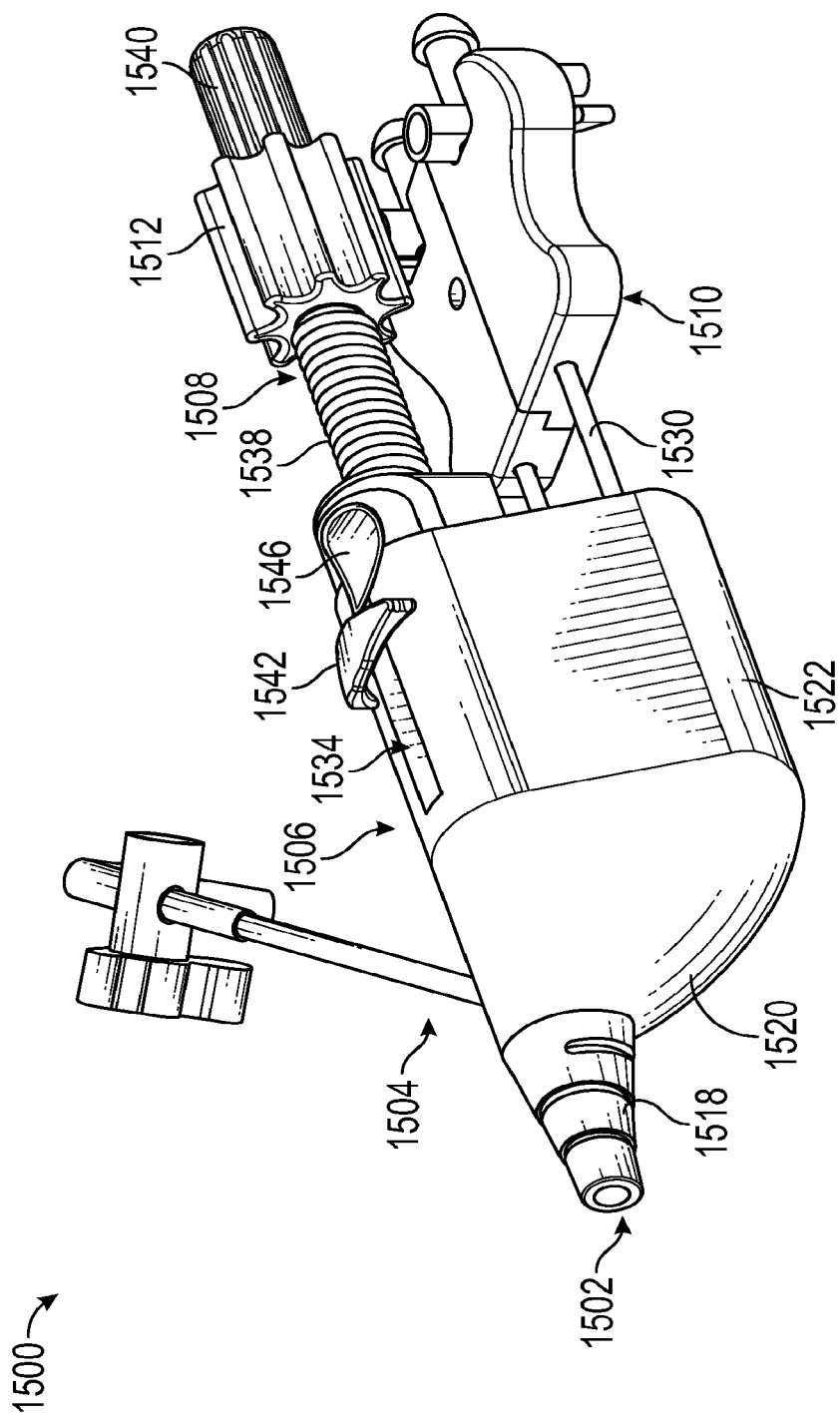
FIGS. 46-54 illustrate another exemplary handle for a delivery apparatus and its components.

FIGS. 46-54 show an exemplary embodiment of a handle 1500 and it components. The handle 1500 can be used, for example, with the third catheter 508 of the delivery apparatus 502 in lieu of the handle 522. Referring to FIG. 46, the handle 1500 has five main components: a connection member 1502, a flushing mechanism 1504, a housing 1506, an anchor actuation mechanism 1508, and a clasp actuation mechanism 1510.

The configuration of the handle 1500 is generally similar to the configuration of the handles 522, 700. The anchor actuation mechanism 1508 of the handle 1500 is configured to allow a user to actuate anchors of a prosthetic spacer device (e.g., the anchors 204) by axially moving (e.g., pushing/pulling) an actuation knob 1512 of the anchor actuation mechanism 1508 (e.g., similar to the actuation of the knob 526 described above) or by rotating the actuation knob 1512 (e.g., similar to actuation of the knob 718 described above), as further described below. In this manner, the anchor actuation mechanism 1508 provides both axial and rotational actuation of the anchor actuation mechanism 1508, which is also referred to herein as "hybrid actuation."

Referring still to FIG. 46, the connection member 1502 can be coupled the distal end portion of the housing 1506 and to the proximal end portion 520a of the outer shaft 520 (not shown). The connection member 1502 can be configured to a provide strain relief to the outer shaft 520. Reducing the strain on the outer shaft can, for example, reduce kinking of the outer shaft 520 near the housing 1506.

Figure 47:
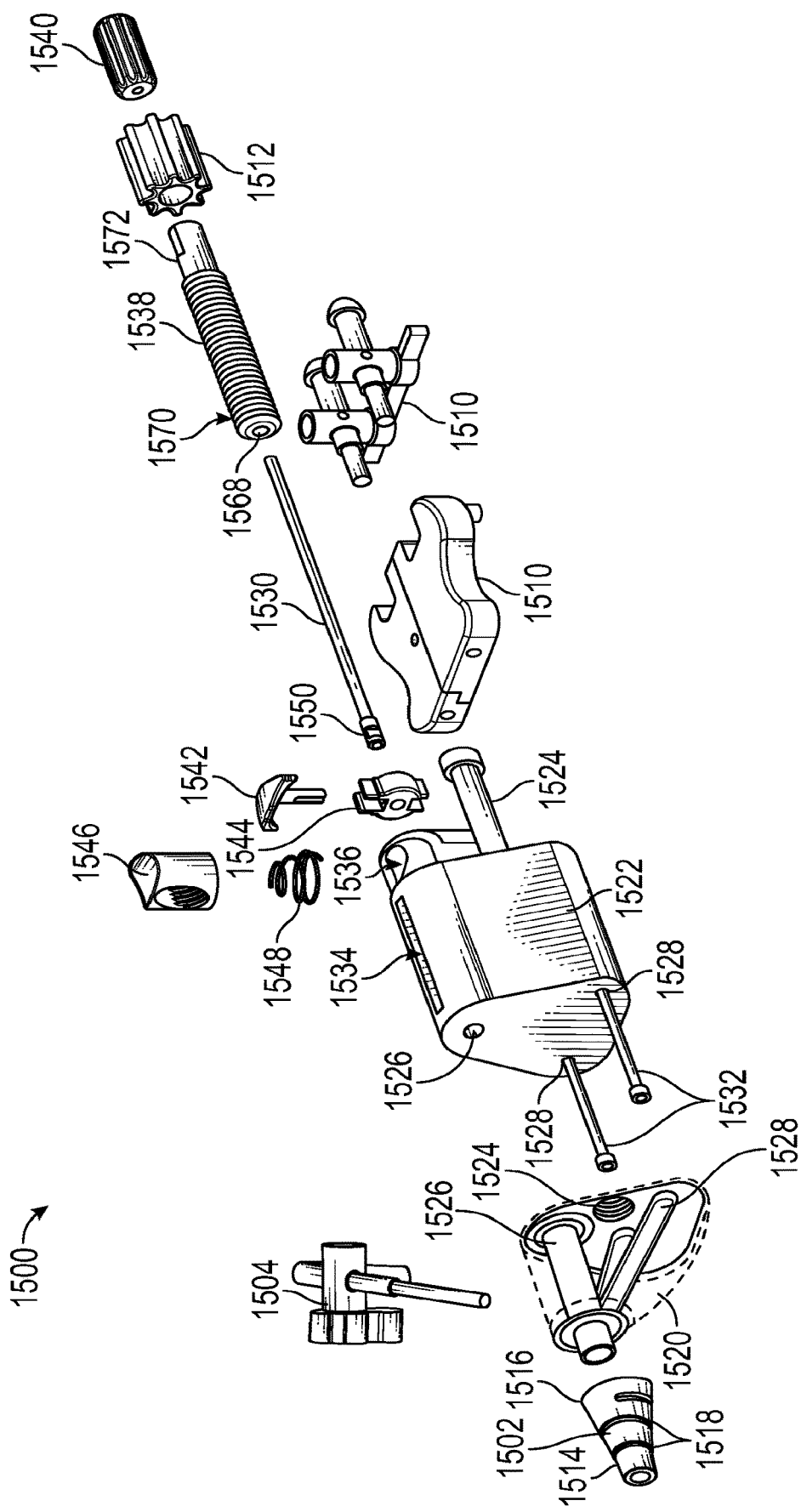

Referring now to FIG. 47, the connection member 1502 can, for example, have a generally conical shape that tapers radially outwardly from a distal end portion 1514 to a proximal end portion 1516. The connection member 1502 can also have one or more slits or grooves 1518, which can facilitate flexing. The slits 1518 can extend circumferentially around the connection member 1502.

As shown in FIG. 46, the flushing mechanism 1504 of the handle 1500 can be coupled to and in fluidic communication with the housing 1506 and the outer shaft (not shown). In this manner, the flushing mechanism 1504 can be used to flush the outer shaft (e.g., with a saline solution) prior to inserting the third catheter 508 into a patient's body.

As shown in FIG. 47, the housing 1506 of the handle 1500 can include a nose portion 1520 and a main body 1522. The nose portion 1520 and the main body 1522 can, for example, be coupled together with a fastener (e.g., a bolt) 1524. The nose portion 1520 and the main body 1522 can include a plurality of lumens, including an actuation shaft lumen 1526 and control member lumens 1528. Actuation tube 1530 can be disposed in and axially movable relative to the actuation shaft lumen 1526. Clasp control tubes 1532 can be disposed in an axially movable relative to the control member lumens 1528.

The main body 1522 of the housing 1506 can also include a slot 1534 and a bore 1536 that are configured for receiving one or more components of the anchor actuation mechanism 1508, as further described below. The slot 1534 can extend radially into and axially along the actuation shaft lumen 1526 of the housing 1506. The bore 1536 can be disposed proximal to the slot 1534 and can extend radially into the actuation shaft lumen 1526 of the housing 1506.

In some embodiments, the housing 1506 can have a generally triangular cross-sectional shape taken in a plane perpendicular to the longitudinal axis of the actuation lumen 1526. In other embodiments, the housing can be a variety of other shapes such as rectangular, circular, etc.

The anchor actuation mechanism 1508 can be used to move the actuation shaft 512 axially relative to the housing 1506 (and thus the outer shaft 520), and thus the anchors 204 of the prosthetic spacer device 200 (which can be coupled to the actuation shaft 512). The anchor actuation mechanism 1508 can also be used to release the actuation shaft from the prosthetic spacer device. The anchor actuation mechanism 1508 can include the actuation tube 1530, a drive screw 1538, the actuation knob 1512, a release knob 1540, a release pin 1542, a bushing 1544, a mode selector button 1546, and a biasing element (e.g., a spring) 1548.

Figure 48:
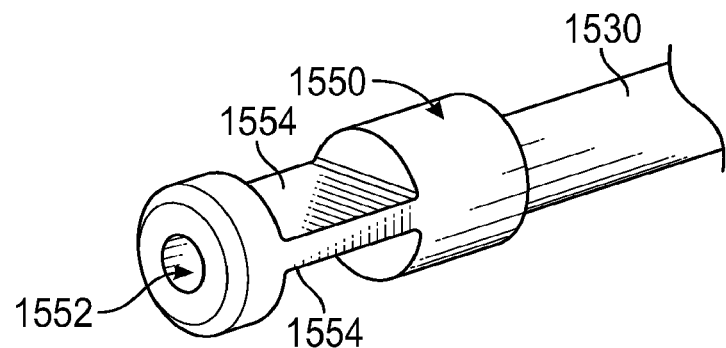
Figure 49:
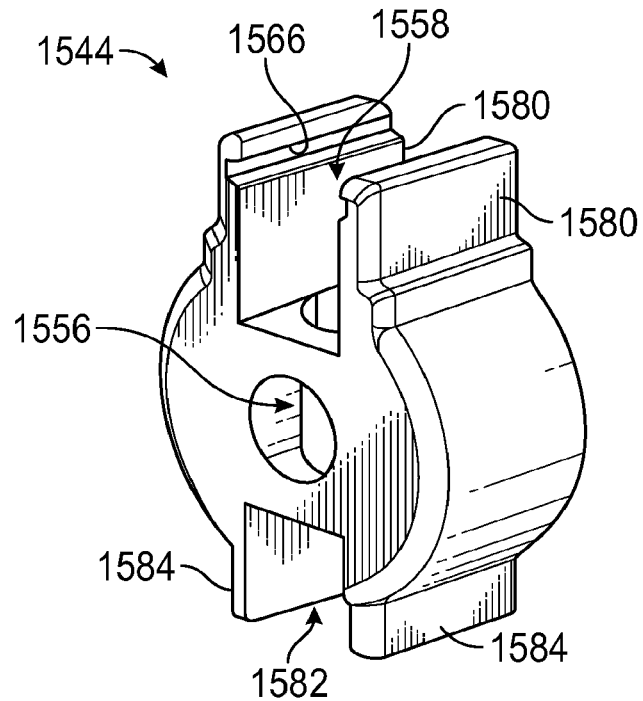

Referring to FIG. 48, the actuation tube 1530 can have a flange 1550 disposed at the distal end portion of the actuation tube and a lumen 1552 extending from the distal end portion to a proximal end portion of the actuation tube. The flange 1550 can be used, for example, to couple the actuation tube 1530 to the release pin 1542 and the bushing 1544. The lumen 1552 can, for example, receive an actuation shaft (e.g., the actuation shaft 512).

Figure 50:
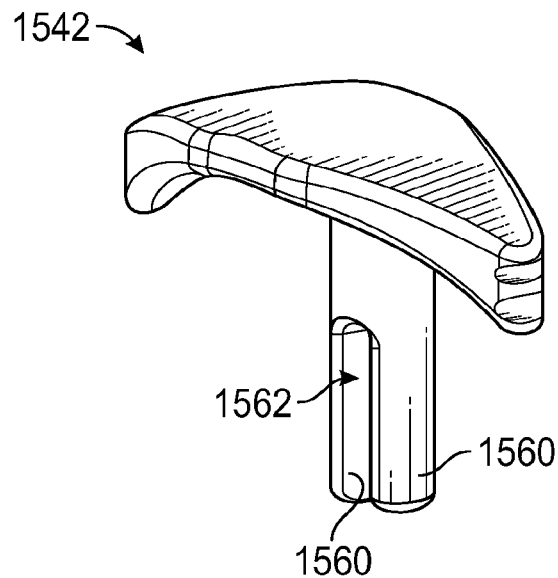
Figure 51:
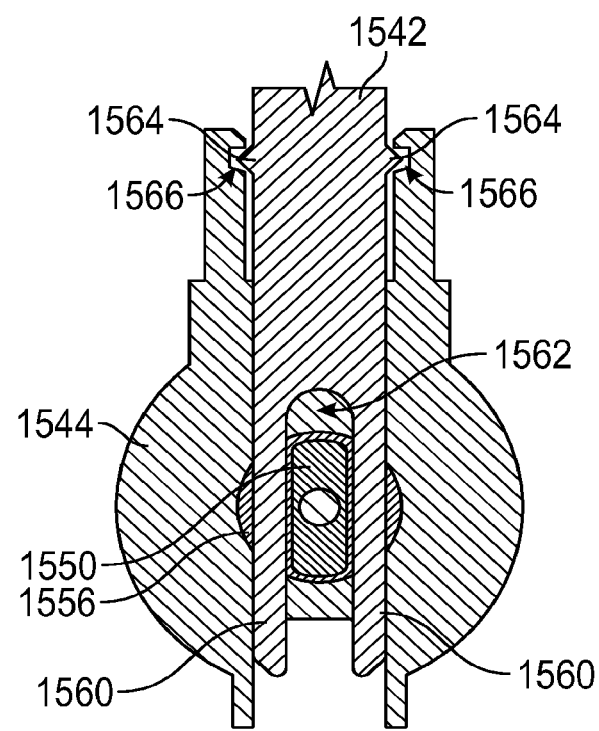

As shown in FIG. 48, the flange 1550 can have one or more recessed portions or "flats" 1554 (e.g., two on diametrically opposite sides of the flange 1550). In this manner, the flange 1550 of the actuation tube 1530 can be inserted into a first opening 1556 (FIG. 49) of the bushing 1544, and the release pin 1542 can be inserted into a second opening 1558 (FIG. 49) of the bushing 1544 to couple actuation tube 1530 and the bushing 1544 together, as shown in FIG. 51. Referring to FIG. 50, the release pin 1542 can have one or more tabs 1560 (e.g., two in the illustrated embodiment) that are spaced apart by a groove 1562. Referring again to FIG. 51, the tabs 1560 and groove 1562 of the release pin 1542 and/or the flange 1550 of the actuation tube 1530 can be sized and configured such that tabs 1560 of the release pin 1542 extend alongside and engage the flats 1554 of the actuation tube 1530. In the engaged configuration (e.g., FIG. 51), the release pin 1542 restricts relative movement (e.g., rotational and axial) between the actuation tube 1530 and the bushing 1544.

In some embodiments, the release pin 1542 and the bushing 1544 can have locking elements 1564, 1566, respectively. The locking elements 1564, 1566 can, for example, help retain the release pin 1542 and the bushing 1544 in the engaged configuration. The locking elements 1566 can be slots formed on an inner surface of the bushing 1544 and the locking elements 1564 can be tabs or protrusions formed on the release pin 1542 and sized to be received within corresponding slots 1566. Alternatively, the tabs 1564 can be formed on the bushing and the slots 1566 can be formed on the release pin. The tabs 1564, when received in the slots 1566, prevent inadvertent movement of the release pin relative to the bushing, yet allow the release pin to be manually removed from the bushing when so desired by the user.

Referring to FIG. 47, the drive screw 1538 can comprise a lumen 1568, a distal portion 1570, and a proximal portion 1572. The lumen 1568 can extend from the distal portion 1570 of the drive screw 1538 to the proximal portion 1572 of the drive screw 1538.

The lumen 1568 of the drive screw 1538 and/or the actuation tube 1530 can be sized and configured such that the actuation tube 1530 can extend through the lumen 1568 and such that the actuation tube 1530 can move rotationally and axially relative to the drive screw 1538.

The distal portion 1570 of the drive screw 1538 can comprise threads (e.g., external treads) that are configured to engage corresponding threads (e.g., internal threads) of the mode selector button 1546, as further described below.

The proximal portion 1572 of the drive screw 1538 can be fixedly coupled to the actuation knob 1512. As such, movement (e.g., rotational and axial) of the actuation knob 1512 can result in corresponding movement of the drive screw 1538. In some embodiments, the actuation knob 1512 can be fixedly coupled to the drive screw with a fastener (e.g., a set screw), adhesive, and/or other means for fastening. In other embodiments, the actuation knob 1512 can be fixedly coupled to the drive screw 1538 by integrally forming the actuation knob 1512 and the drive screw 1538 as a single, unitary component.

The release knob 1540 can be fixedly coupled to a proximal end portion of the actuation tube 1530. As such, movement (e.g., rotational and/or axial) of the release knob 1540 can result in corresponding movement of the actuation tube 1530. In some embodiments, the actuation knob 1512 can be fixedly coupled to the drive screw 1538 with a fastener (e.g., a set screw), adhesive, and/or other means for fastening.

Figure 52:
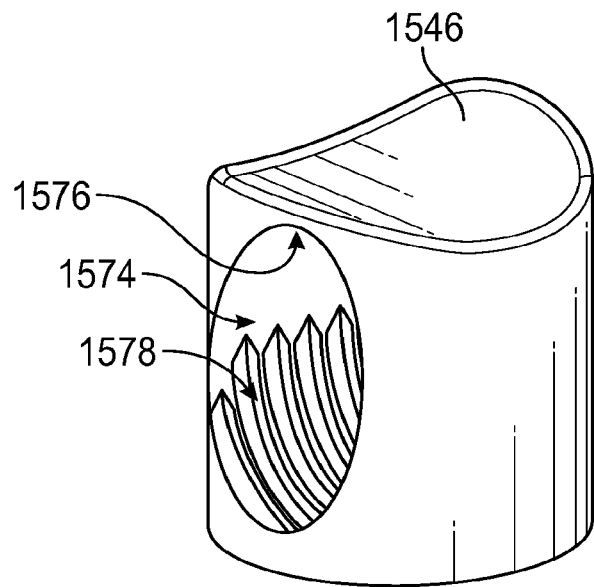
Figure 53A:
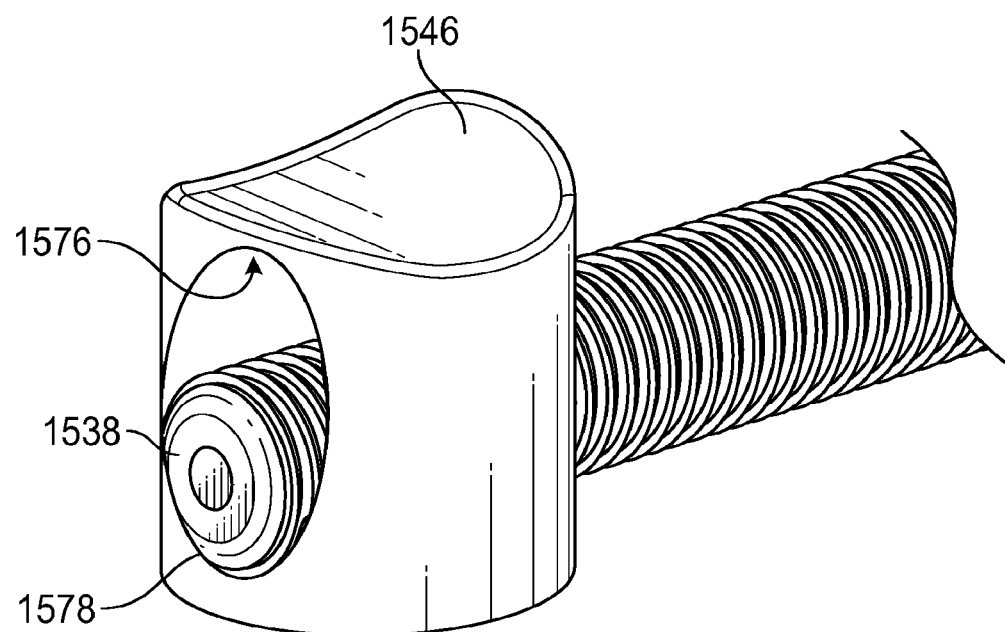
Figure 53B:
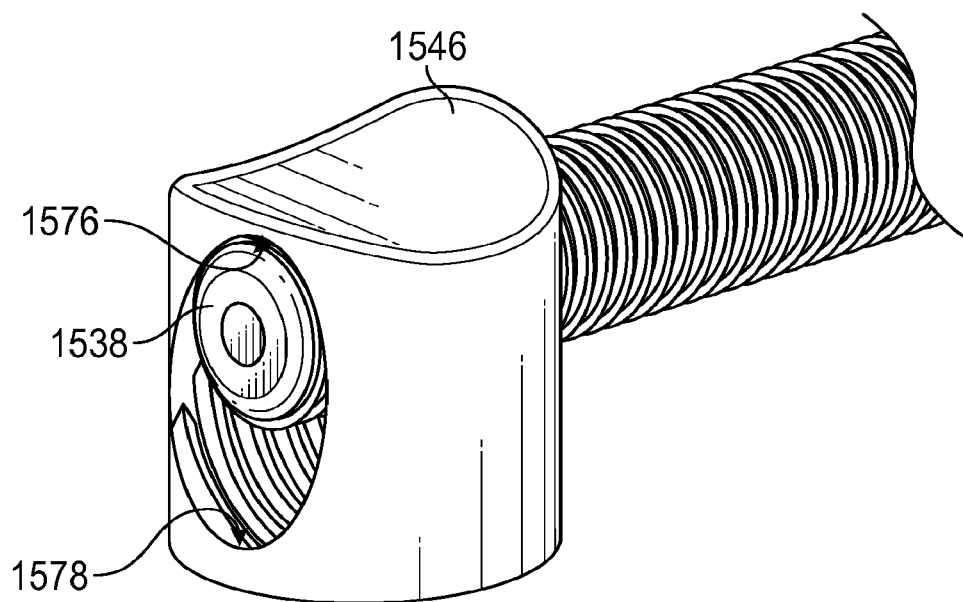
Figure 54:
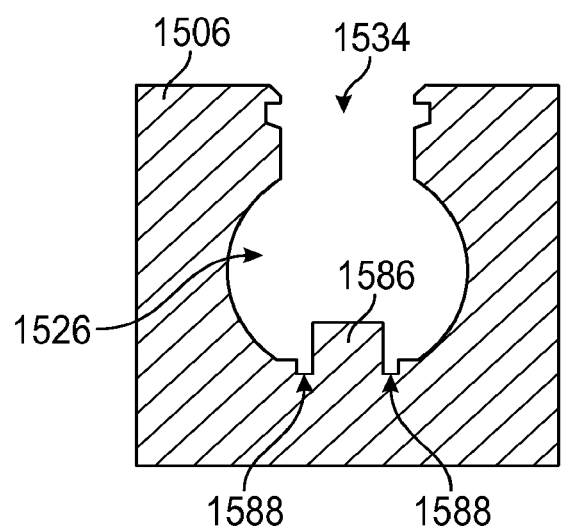

Referring to FIG. 52, the mode selector button 1546 can have an opening 1574. The opening 1574 can be elliptical and configured to receive the drive screw 1538. The annular surface defining the opening 1574 can have a first portion 1576 (i.e., the upper portion in the depicted orientation) and a second portion 1578 (i.e., the lower portion in the depicted orientation). The first portion 1576 can be generally smooth. The second portion 1578 can have threads (e.g., internal threads) configured to engage corresponding threads of the distal portion 1570 of the drive screw 1538, as shown in FIG. 53A. The opening 1574 of the button 1546 can be sized and configured such that when the first portion 1576 of the button 1546 contacts the drive screw 1538, the threads of the second portion 1578 of the button 1546 disengage the threads of the drive screw 1538, as shown in FIG. 53B. This configuration allows relative movement (e.g., axial) between the button 1546 and the drive screw 1538, as further described below.

Referring to FIGS. 46-47, the anchor actuation mechanism 1508 of the handle 1500 can be assembled by inserting the bushing 1544 into the actuation lumen 1526 of the housing 1506 such that ears 1580 (FIG. 49) of the bushing 1544 extend out of the slot 1534 of the housing 1506. In this manner, the slot 1534 of the housing 1506 can act as a track or guide for the bushing 1544 that allows relative axial movement of the bushing 1544 within the actuation lumen 1526 of the housing 1506 and restricts relative rotational movement between the bushing 1544 and the housing 1506. In some embodiments, the bushing 1544 can have additional mating features (e.g., a slot 1582 and/or tabs 1584 (FIG. 49)) that can engage with corresponding mating features (e.g., rails 1586 and/or notches 1588 (FIG. 54)) of the actuation lumen 1526 of the housing 1506 to restrict relative rotational movement between the bushing 1544 and the housing 1506.

The biasing member 1548 can be positioned within the bore 1536 of the housing 1506, and the mode selector button 1546 can be disposed on the biasing member 1548 and within the bore 1536. The button 1546 can then be pressed inwardly relative to the bore 1536 of the housing 1506 (to overcome the outward force of the biasing member 1548 on the button 1546) such that the opening 1574 of the button 1546 radially aligns with the actuation lumen 1526 of the housing 1506.

In this configuration, the drive screw 1538 can be inserted into the actuation lumen 1526 of the housing and through the opening 1574 of the button 1546 such that the distal end portion 1570 of the drive screw 1538 abuts the bushing 1544.

The actuation tube 1530 can be inserted through the lumen 1568 of the drive screw 1538 such that the release knob 1540 abuts the actuation knob 1512 and such that the flange 1550 of the actuation tube 1530 extends distally from the lumen 1568 of the drive screw 1538 and into the first opening 1556 of the bushing 1544. The release pin 1542 can be inserted into the second opening 1558 of the bushing 1544 and such that the tabs 1560 of the release pin 1560 engage the flats 1554 of the flange 1550, as shown in FIG. 51. Accordingly, with the release pin 1542 engaged, the actuation tube 1530 cannot rotate relative to bushing 1544 or the housing 1506. Also, the actuation shaft 1530 and the drive screw 1538 move together axially. This is because the actuation shaft cannot move proximally relative to the drive shaft 1538 due to the bushing 1544 (which cannot extend into the lumen 1568 of the drive screw 1538 and because the actuation shaft cannot move distally relative to the drive shaft 1538 due to the release knob 1540 (which cannot extend past the actuation knob 1512). The drive screw 1538 can, however, rotate relative to the actuation shaft 1530.

Once assembled (e.g., FIG. 46), the anchor actuation mechanism 1508 can be operated in rotational mode and sliding mode. Due to the biasing member 1548 urging the threaded second portion 1578 of the mode selector button 1546 against the threads of the drive screw 1538 (see e.g., FIG. 53A), the default mode of operation is the rotational mode.

In alternative embodiments, the mode selector button 1546 can be configured such that the default mode of operation is the sliding mode. This can be accomplished, for example, by switching the placement of the threaded portion 1578 and the smooth portion 1576 of the button 1546.

In the rotational mode, anchors of a prosthetic spacer device can be actuated by rotating the actuation knob 1512 relative to the housing 1506. This moves the drive screw 1538 axially relative to the button 1546. As the drive screw 1538 moves axially, the drive screw 1538 carries the actuation tube 1530 (and the actuation shaft 512 which can be coupled to the actuation tube 1530) axially along with it. Also, the release pin 1542 moves axially relative to the slot 1532, and the bushing 1544 moves axially relative to the actuation lumen 1526.

Rotating the actuation knob 1512 in a first direction (e.g., clockwise) relative to the housing 1506 can result in the anchors of the prosthetic spacer device opening or unfolding away from the spacer body. Rotating the actuation knob 1512 in a second direction (e.g., counterclockwise) relative to the housing 1506 can result in the anchors of the prosthetic spacer device closing or folding toward the spacer body.

To switch from rotational mode to sliding mode, the user can press the mode selector button 1546 inwardly relative to the housing 1506. This movement disengages the threads of the button 1546 from the threads of the drive screw 1538, thereby allowing the user to open the anchors of the prosthetic spacer device by pushing the actuation knob 1512 distally relative to the housing 1506 or to close the anchors of the prosthetic spacer device by pulling the actuation knob 1512 proximally relative to the housing 1506.

Due to the dual/hybrid actuation modes, the handle 1500 provides several significant advantages. For example, the handle 1500 allows a user to have both the quick and/or course adjustment of push/pull actuation and the precise and/or fine adjustment of rotational actuation. The handle 1500 also provides a locking mechanism in either mode of operation because the actuation shaft 512 cannot be moved relative to the housing 1506 without the user rotating the actuation knob 1512 and/or pressing the mode selector button 1546 and moving the actuation knob 1512 axially.

To release the actuation shaft from the prosthetic spacer device, the user can withdraw the release pin 1542 from the actuation tube 1530, the bushing 1544, and the slot 1534. This allows the user to rotate the release knob 1540 (e.g., counterclockwise) relative to the housing 1506, which in turn, results in the actuation tube 1530 and the actuation shaft rotating relative to the housing 1506 and the prosthetic spacer device. This can retract the actuation shaft from the distal collar of the prosthetic spacer device. The release knob 1540 can then be moved proximally relative to the housing 1506 to withdraw the actuation shaft from the prosthetic spacer device and the coupler 514 of the outer shaft 520, thereby releasing the prosthetic spacer device from the delivery apparatus.

In some embodiments, the release knob 1540 and the release pin 1542 can be a first color (e.g., blue), the actuation knob 1512 can be a second color (e.g., black), and the mode selector button 1546 can be a third color (e.g., gray). This can, for example, provide the user with visual indicators that the release knob 1540 and the release pin 1542 are related (i.e., because they are the same color) and that the actuation knob 1512, release knob 1540, and mode selector button 1546 preform separate functions (i.e., because they are different colors).

Additionally or alternatively, the release knob 1540 and the release pin 1542 can have other indicators or features such as lettering (e.g., "Release"), symbols (e.g., an unlocked lock), and/or texturing (e.g., ribs) to make the components easier and/or more intuitive to use. Similarly, the mode selector button 1546 and/or the actuation knob 1512 can have one or more such indicators or features.

The clasp control mechanism 1510 of the handle 1500 can be configured similar to the clasp control mechanism 550 described above.

Figure 55:
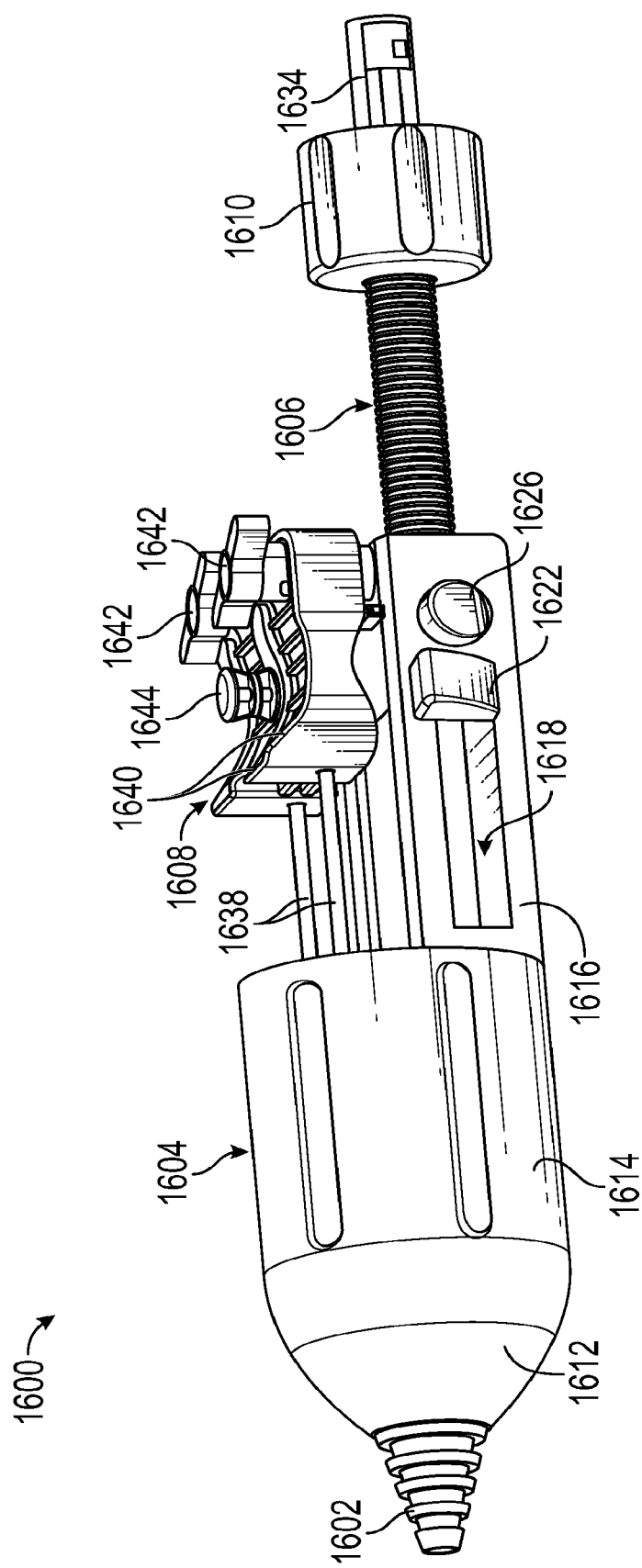
FIGS. 55-61D illustrate another exemplary handle for a delivery apparatus and its components.

FIGS. 55-61D show an exemplary embodiment of a handle 1600 and it components. The handle 1600 can be used, for example, with the third catheter 508 of the delivery apparatus 502 in lieu of the handle 522. Referring to FIG. 55, the handle 1600 has five main components: a connection member 1602, a flushing mechanism (not shown), a housing 1604, an anchor actuation mechanism 1606, and a clasp actuation mechanism 1608.

The handle 1600 is configured similar to the handle 1500. The anchor actuation mechanism 1606 of the handle 1600 is configured to allow a user to actuate anchors of a prosthetic spacer device (e.g., the anchors 204) by axial (i.e., distal/proximal) movement of an actuation knob 1610 of the anchor actuation mechanism 1606 and by rotational movement (i.e., clockwise/counterclockwise) of the actuation knob 1610, as further described below. In this manner, the anchor actuation mechanism 1508 provides hybrid anchor actuation (e.g., similar to the handle 1500).

The housing 1604 of the handle 1600 can include a nose portion 1612, a main body 1614, and a support portion 1616. The distal end of the nose portion 1612 can be coupled to the connection member 1602 and/or the outer shaft 520, and the proximal end of the nose portion 1612 can be coupled to the distal end of the main body 1614. The support portion 1616 can be coupled to the proximal end of the main body 1614.

The nose portion 1612, the main body 1614, and the support portion 1616 of the housing 1604 can include an actuation lumen (not shown). The nose portion 1612 and the main body 1614 can also include a plurality (e.g., two) of clasp control lumens (not shown).

The main body 1614 of the housing 1604 can have a generally cylindrical or rounded shape. The cylindrical shape can, for example, allow the handle 1600 to be placed or secured to an object (e.g., a table) in any rotational orientation (e.g., when rotating the outer shaft 520). The cylindrical shape can also help the handle 1600 maintain its rotational orientation relative to the object because the handle 1600 does not have flat sides for the handle to pivot or flop toward.

The support portion 1616 of the housing 1604 can have a generally rectangular shape. In some embodiments, the edges of the support portion 1616 can be rounded and have radii similar to the radius of the main body 1614.

Figure 56:
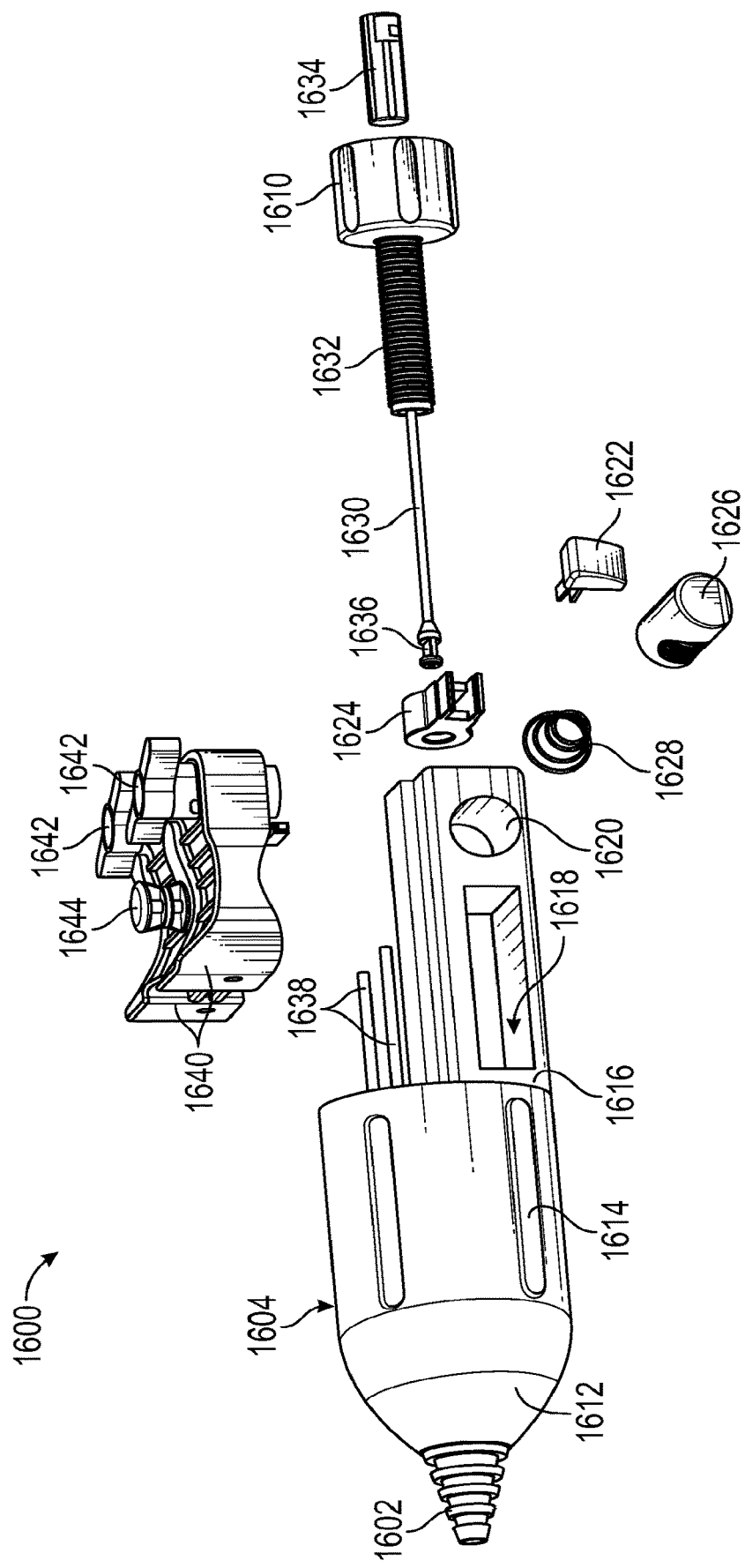
Figure 57:
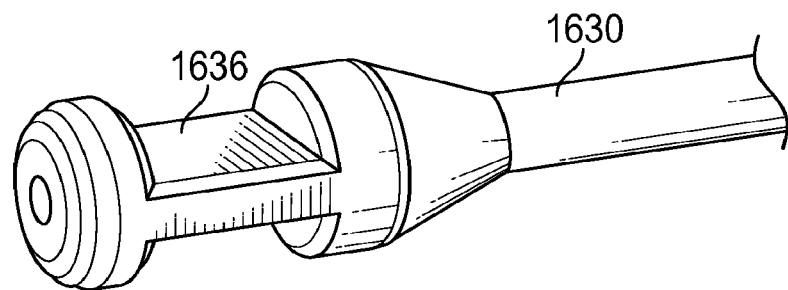
Figure 58:
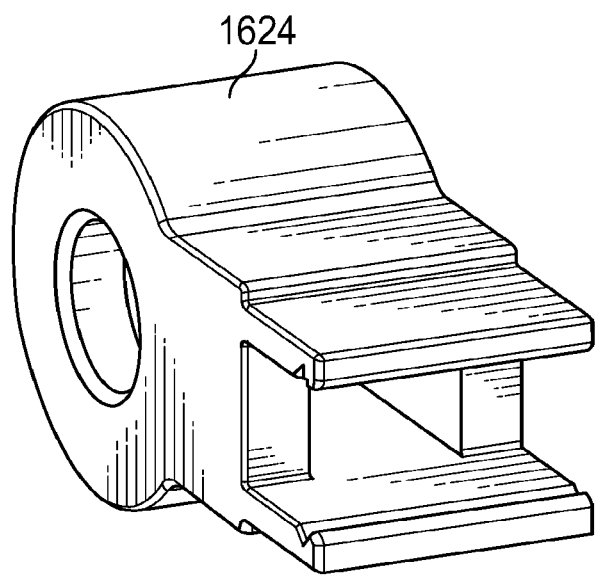
Figure 59:
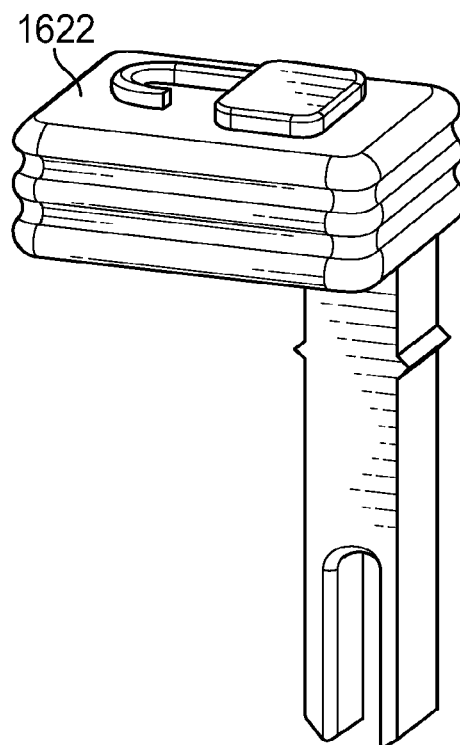

Referring to FIG. 56, the support portion 1616 of the housing 1604 can include a slot 1618 extending from the actuation lumen. The slot 1618 can be configured to receive a release pin 1622 and/or bushing 1624 of the actuation mechanism 1606 (e.g., similar to the slot 1534 of the handle 1500). The support portion 1616 can also include a bore 1620. The bore 1620 can be configured to receive a mode selector button 1626 and a biasing member (e.g., a spring) 1628 of the actuation mechanism 1606.

Figure 60:
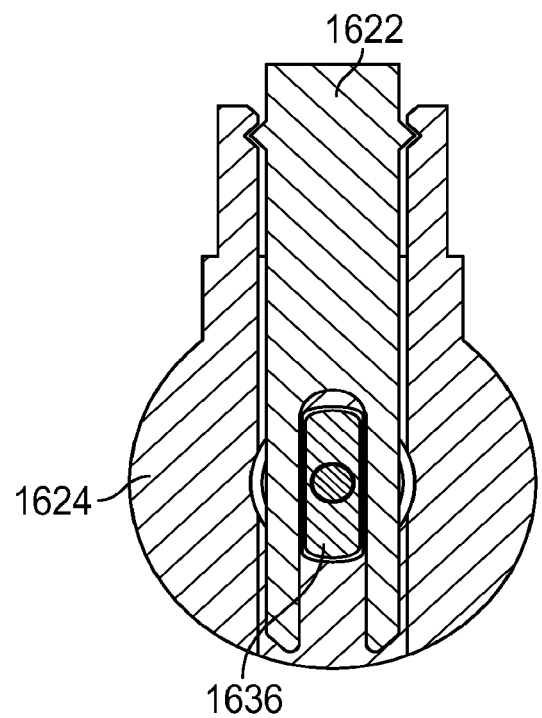

Referring to FIG. 56, the actuation mechanism 1606 of the handle 1600 can include an actuation tube 1630, a drive screw 1632, the actuation knob 1610, a release knob 1634, a release pin 1622, a bushing 1624, a mode selector button 1626, and a biasing member 1628. The actuation mechanism 1606 can be configured, assembled, and operated in a manner similar to the actuation mechanism 1508 of the handle 1500. For example, FIGS. 57-59 respectively show detailed views of a distal portion 1636 of the actuation tube 1630, the bushing 1624, and the release pin 1622. FIG. 60 shows the distal portion 1636 of the actuation tube 1630 coupled to the bushing 1624 by the release pin 1622. FIG. 55 shows the entire actuation mechanism 1606 assembled and coupled to the housing 1604.

Referring to FIG. 55, the clasp control mechanism 1608 of the handle 1600 can include clasp tubes 1638, actuators 1640, and locking members 1642. In the illustrated embodiment, there are two tubes clasp tubes 1632, two actuators 1640, and two locking members 1642. In other embodiments, the clasp control mechanism 1608 can have more (e.g., three) or less (e.g., one) than two of the tubes, actuators, and locking members.

A distal end portion of each of the clasp tubes 1638 can be disposed in and axially moveable relative to a respective control lumen of the main body 1614. A proximal end portion of each of the clasp tubes 1638 can be coupled to a respective actuator 1640. Each of the locking members 1642 (e.g., stop cocks) can be coupled to a respective actuator 1640. The clasp control members 524 (FIG. 15) can extend through the clasp tubes 1638 and can be releasably secured to actuators by the locking members 1642.

The actuators 1640 can be selectively coupled together, for example, by a removable pin 1644. As such, the actuators 1640 can be moved together to actuate the clasp control members 524 (and thus the clasps 206 of the prosthetic spacer device) simultaneously when the pin 1644 is inserted into the actuators 1640. When the pin 1644 is removed, the actuators 1640 (the clasps 206) can be moved individually.

Figure 61A:
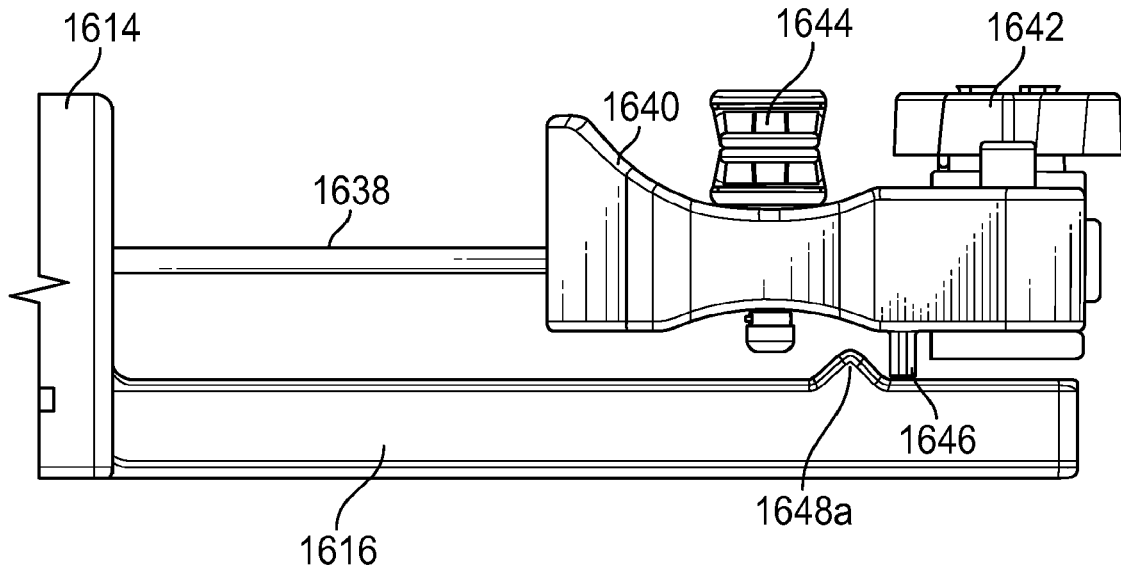

Referring to FIG. 61A, in some embodiments, each of the actuators 1640 can have a retention member (e.g., a pin) 1646 disposed on and/or extending from a surface of the actuator 1640 that faces the support portion 1616 of the housing 1604. The retention member 1646 can be configured to engage the support portion 1616 of the housing 1604 to retain the relative position of the actuators 1640 and the housing 1604, which in turn retains the positioning of the clasps of the prosthetic spacer device.

In some embodiments, the retention members 1646 can be sized and/or configured so as to position the clasp tubes 1638 slightly off-axis relative to the control lumens of the housing 1604. In this manner, the clasp tubes 1638 act as biasing members that force the retention members 1646 against the support portion 1616. This force results in a frictional engagement between the clasp tubes 1638 and the support portion 1616, thus reducing the likelihood that the actuators 1640 will be inadvertently moved relative to the support portion 1616. The frictional engagement can also help to retain the positioning of the clasps of the prosthetic device in the open position by overcoming the tensile force on the clasp control members and the actuators that is caused by the bias of the clasps toward the closed position.

In other embodiments, the retention members 1646 can be sized and/or configured so as to position the clasp tubes 1638 coaxial to the control lumens of the housing 1604, and the support portion 1616 of the housing 1604 can have one or more holding elements (see holding elements 1648a, 1648b, 1648c, and 1648d shown in FIGS. 61A-61D, respectively, and which are also be referred to generically and/or collectively as "the holding elements 1648"), that are disposed on and/or extend from a surface of the support portion 1616 that faces the actuators 1640. The holding elements 1648 can be configured to engage the actuators 1640 and/or the retention members 1646 to retain the relative position of the actuators 1640 and the housing 1604, which in turn retains the positioning of the clasps of the prosthetic spacer device.

FIG. 61A shows an exemplary holding element 1648a. The holding element 1648a comprises a projection or ridge that extends toward and/or or engages the retention members 1646 of the actuators 1640. Thus, in order for the actuators 1640 to move relative to the housing 1604, the retention members 1646 have to be moved over the holding element 1648a. As the retention members 1646 move over the holding element 1648a, the clasp tubes 1648 are pushed slightly off-axis relative to the control lumens of the housing, thus increasing the frictional engagement between the control lumens and the clasp tubes 1638. This in turn makes it relatively more difficult to move the actuators 1640 relative to the housing 1604. To open the clasps on the prosthetic spacer device, the actuators 1640 are moved to a proximal-most position (as shown in FIG. 61A). The engagement of the retention members 1646 with the holding element 1648a resists movement of the actuators 1640 under the tensile force of the clasps, thereby retaining the clasps in their open position. To close the clasps, the user can push the actuators 1640 distally (to the left in FIG. 61A) with sufficient force to push the retention members 1646 over the holding element 1648a. If desired, the user can slightly lift the actuators away from the support portion 1616 while pushing them distally to allow the retention members 1646 to clear the holding element 1648a.

Figure 61B:
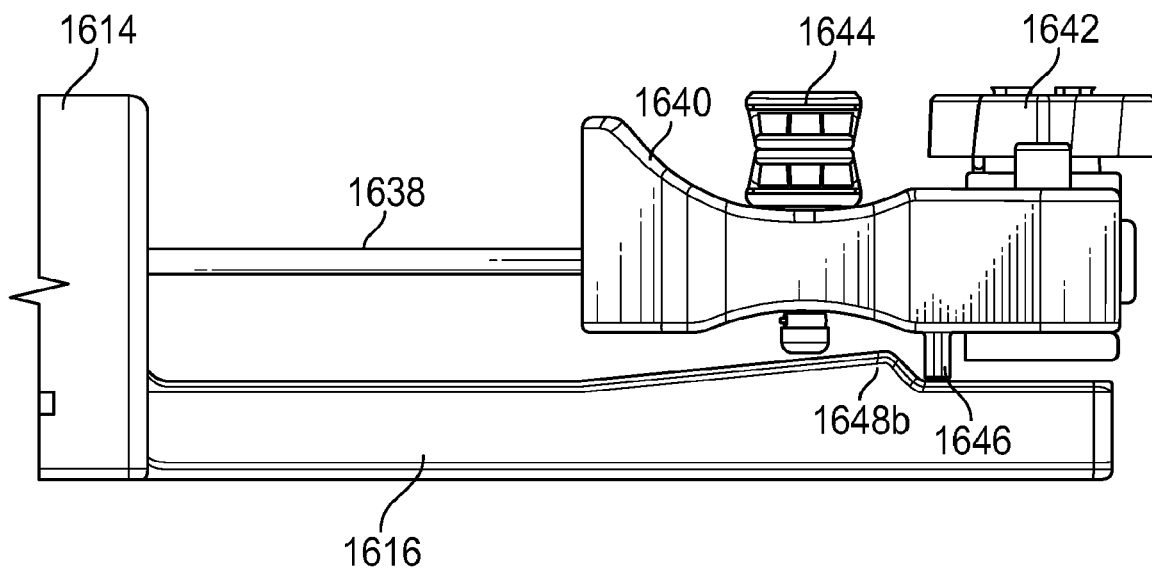

FIG. 61B shows another exemplary holding element 1648b, which can be used, for example, in lieu of the holding element 1648a. The holding element 1648b has a relatively gradual-sloped distal portion and a relatively steep-sloped proximal portion. The steep-sloped proximal portion of the holding element 1648b can act as a lock to selectively hold the retention members 1646 (and thus the actuators 1640) in the proximal-most position. The actuators 1640 can be moved from the proximal-most position by applying sufficient distal force (and/or vertical force) on actuators 1640 so that the retention members 1646 "climb" the steep-sloped proximal portion of the holding element 1648b and move onto the gradual-sloped distal portion of the holding element 1648b. Once the retention members 1648 pass the apex of the holding element 1648b, the actuators tend to move relatively easily in the distal direction due to the gradual-sloped distal portion (and the tension on the clasp control members 524). The actuators 1640 can be moved to the proximal-most position by moving the actuators 1640 proximally with sufficient force for the retention members 1646 to "climb" the gradual-sloped distal portion of the holding element 1648b and move onto the steep-sloped proximal portion of the holding element 1648b. Since the gradual-sloped portion is less abrupt than the steep-sloped portion, the force needed to move the actuators 1640 proximally over the distal portion of the holding element 1648b is relatively less noticeable (i.e., seems easier) to a user than the force needed to move the actuators 1640 distally of the proximal portion of the holding element 1648b. This is in contrast to the holding element 1648a shown in FIG. 61A, which has similar slopes on the proximal and distal sides of the holding element 1648a.

Figure 61C:
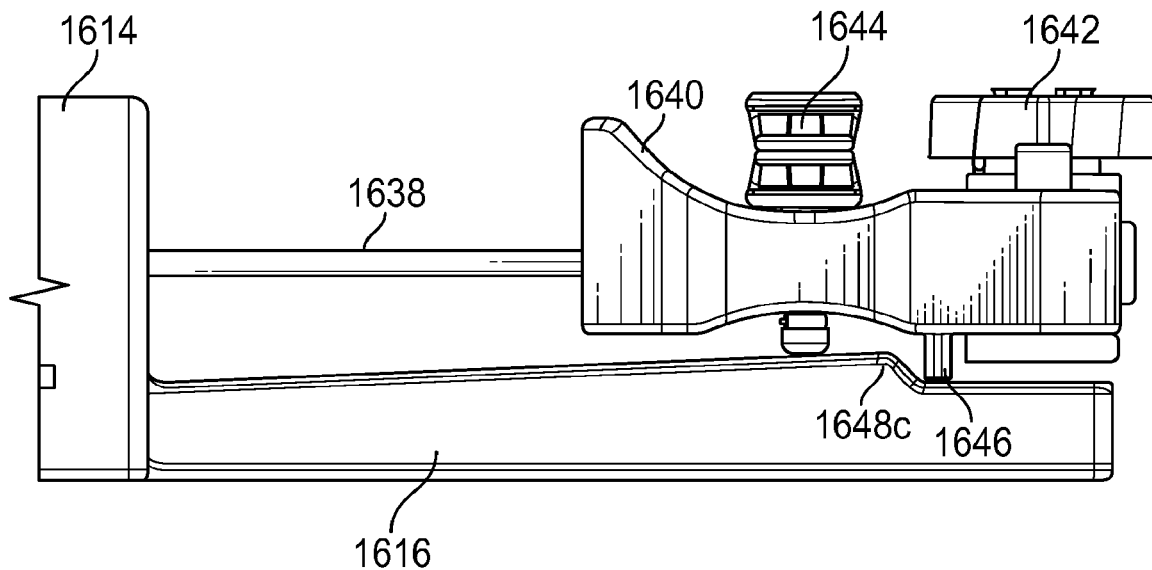

FIG. 61C shows another exemplary holding element 1648c, which can be used, for example, in lieu of the holding elements 1648a, 1648b. The holding element 1648c has a relatively gradual-sloped distal portion and a relatively steep-sloped proximal portion. The proximal portion of the holding element 1648c has a slope that is substantially similar to the slope of the proximal portion of the holding element 1648b (FIG. 61B). The distal portion of the holding element 1648c has a slope that is even more gradual than the slope of the distal portion of the holding element 1648b shown in FIG. 61B.

Figure 61D:
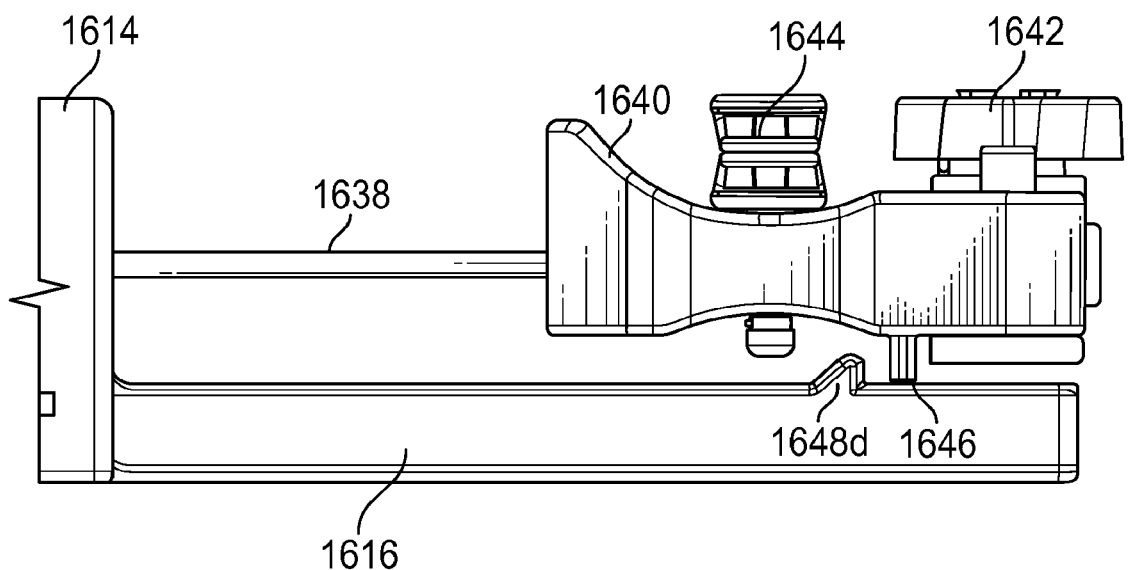

FIG. 61D shows yet another exemplary holding element 1648d, which can be used, for example, in lieu of the holding elements 1648a, 1648b, 1648c. The holding element 1648d has a vertically extending wall or lip on the proximal side and a relatively steep-sloped portion on the distal side. As such, to move the actuators 1640 distally, a user can lift and move the actuators 1640 distally over the holding element 1648d to allow the clasps to move from their open configuration toward the closed configuration. In this manner, the vertical lip of the holding element 1648d can reduce the likelihood that the actuators are inadvertently moved distally compared to the holding elements 1684a, 1684b, and/or 1684c.

In some embodiments, the holding elements 1648 can be configured and/or positioned to retain the actuators 1640 near the proximal end of the support portion 1616. This can, for example, help to retain the clasps of the prosthetic spacer device in the open configuration.

In certain embodiments, the support portion 1616 can have a plurality of holding elements 1648 at various locations along the length of the support portion. For example, a first holding element can be positioned near the proximal end of the support portion (e.g., to hold the actuators 1640 in a proximal-most position to hold the clasps in their open configuration), and a second holding element can be positioned near the distal end of the support portion (e.g., to hold the actuators in a distal-most position to the hold the claps in their closed configuration).

Figure 62:
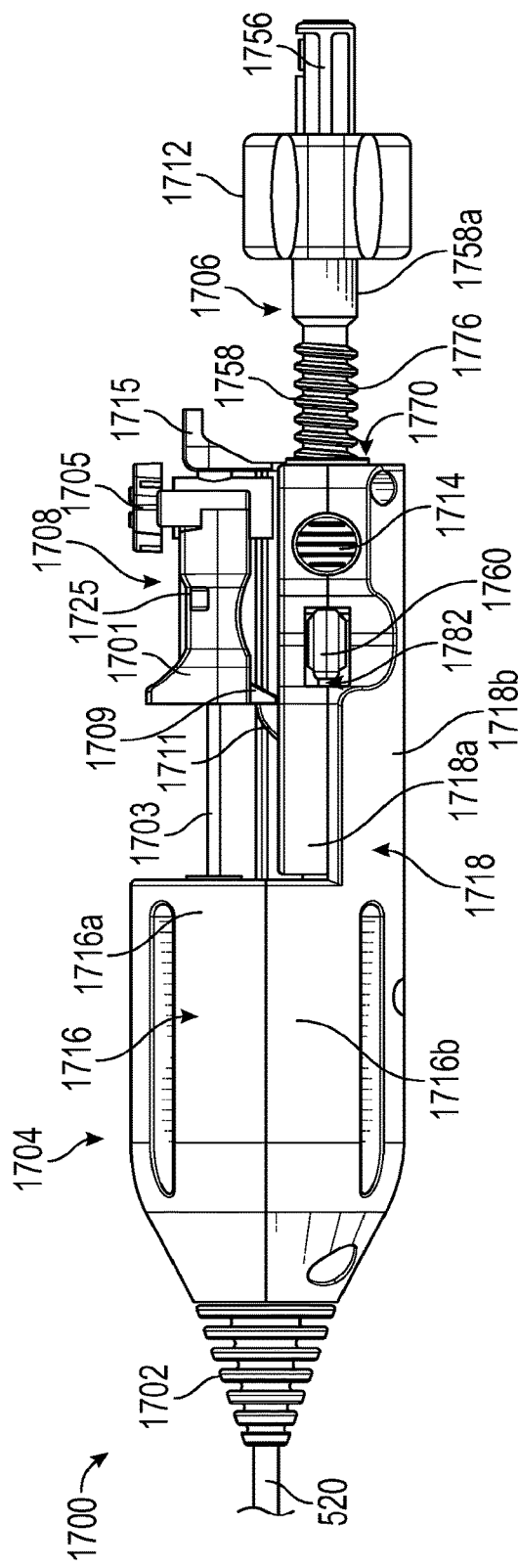
FIGS. 62-75 illustrate another exemplary handle for a delivery apparatus and its components.

FIGS. 62-75 show an exemplary embodiment of a handle 1700 and it components. The handle 1700 can be used, for example, with the third catheter 508 of the delivery apparatus 502 in lieu of the handle 522 to position, secure, and/or deploy a prosthetic spacer device. Referring to FIG. 62, the handle 1700 has five main components: a connection member (which can also be referred to as a strain relief) 1702, a housing 1704, an anchor actuation mechanism 1706, a clasp actuation mechanism 1708, and a flushing mechanism 1710 (which is partially shown in FIG. 63).

The handle 1700 is configured and functions in a manner that is generally similar to the handles 1500, 1600. The anchor actuation mechanism 1706 of the handle 1700 is configured to allow a user to actuate anchors of a prosthetic spacer device (e.g., the anchors 204 of the prosthetic spacer device 200) by either pushing/pulling an actuation knob 1712 of the anchor actuation mechanism 1706 while pressing a mode selector button 1714 or by rotating the actuation knob 1712 without pressing the mode selector button 1714. In this manner, the anchor actuation mechanism 1706 provides hybrid anchor actuation (e.g., similar to the handle 1600).

The housing 1704 of the handle 1700 can include a main body portion 1716 and a support portion 1718. The distal end of the main body 1716 can be coupled to the connection member 1702 and/or the outer shaft 520. The main body 1716 can have a first portion 1716a (i.e., the upper portion in the orientation shown in FIG. 62) and a second portion 1716b (i.e., the lower portion in the orientation shown in FIG. 62). The support portion 1718 can extend from the proximal end of the main body 1716 (e.g., from the second portion 1716b of the main body 1716). The support portion 1718 can have a first portion 1718a (i.e., the upper portion in the orientation shown in FIG. 62) and a second portion 1718b (i.e., the lower portion in the orientation shown in FIG. 62).

Figure 63:
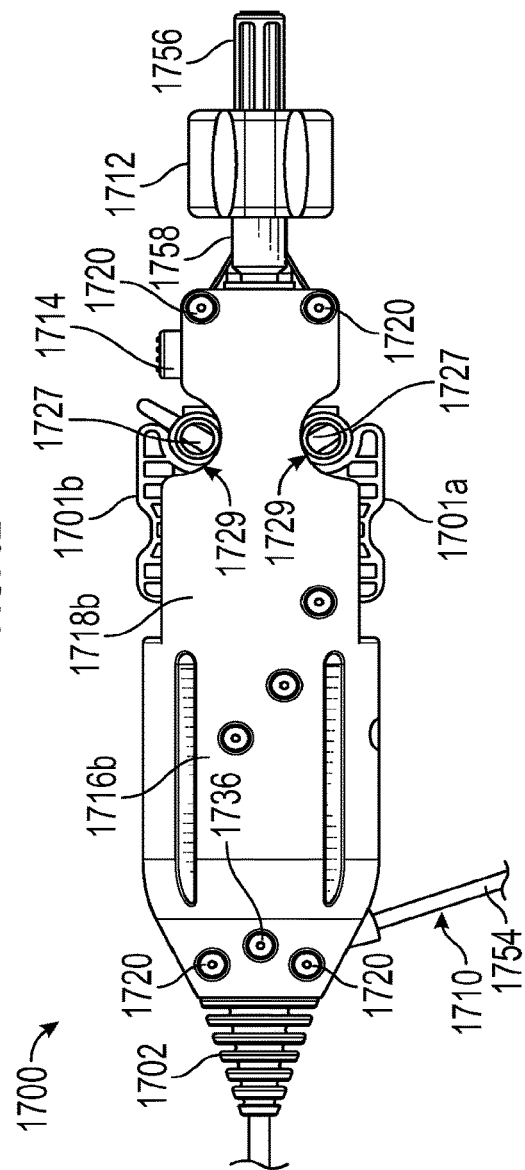

In some embodiments, one or more portions of the main body 1716 and/or one or more portions of the support portion 1720 can be integrally formed (e.g., molded) as a single unitary component or formed as separate components that are coupled together (e.g., with fasteners, frictional engagement (e.g., tabs), adhesive, welding, and/or other means for fastening). For example, as shown in FIGS. 62-63, the second portions 1716b, 1718b of the main body 1716 and the support portion 1718 can be integrally formed, the first and second portions 1716a, 1716b of the main body 1716 can be coupled together with fasteners (e.g., screws 1720), and the first and second portions 1718a, 1718b of the support portion 1718 can be coupled together with fasteners (e.g., screws 1720). In other embodiments, the first and second portions 1716a, 1716b of the main body 1716 can be integrally formed.

Figure 64:
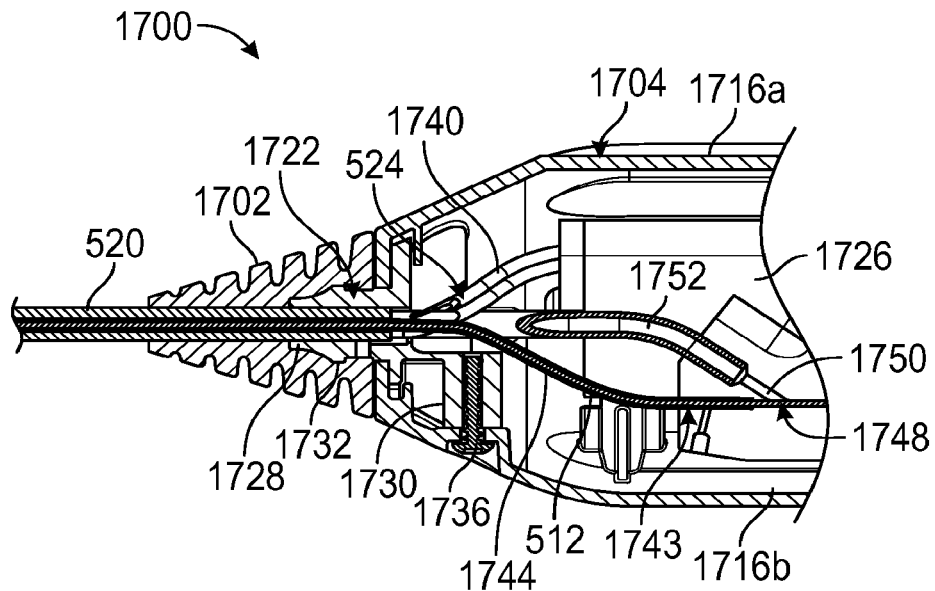
Figure 65:
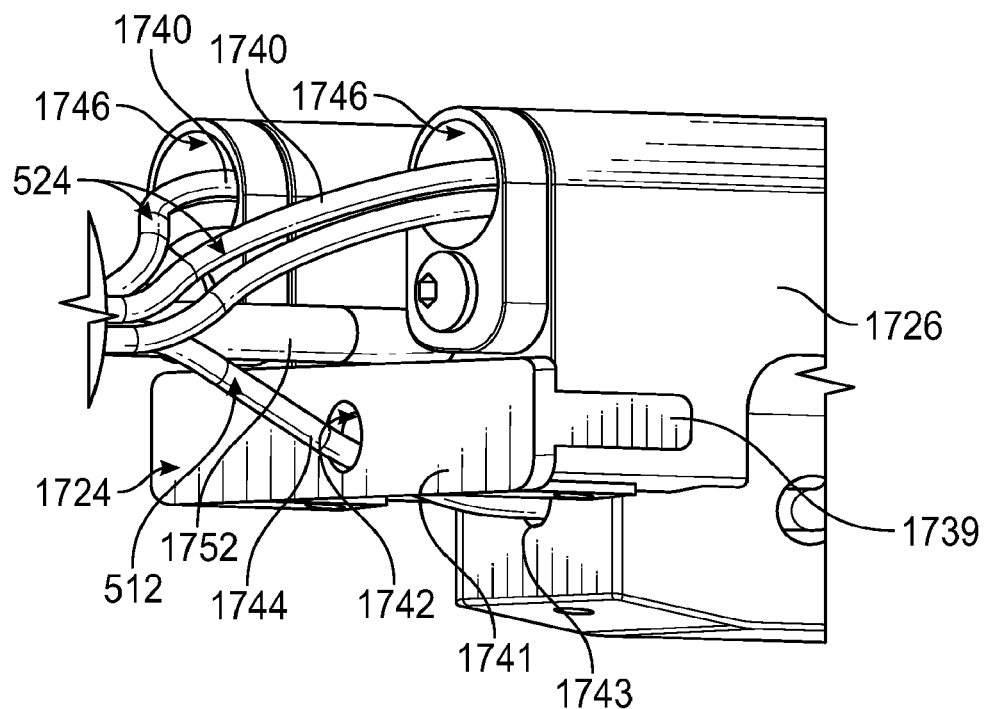

Referring to FIGS. 64-65, the handle 1700 can further comprise various components that are disposed within and/or coupled to the housing 1704. For example, in some embodiments, the handle 1700 can optionally include a coupling member 1722, a stabilizer member 1724, and/or a shaft guide member 1726.

Figure 66:
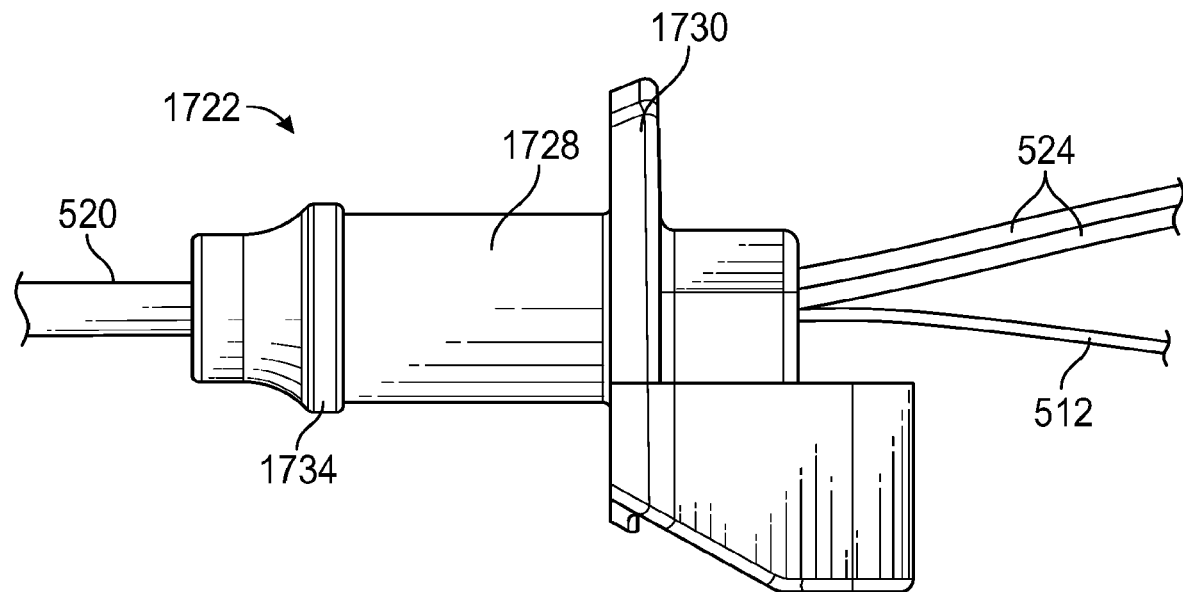
Figure 67:
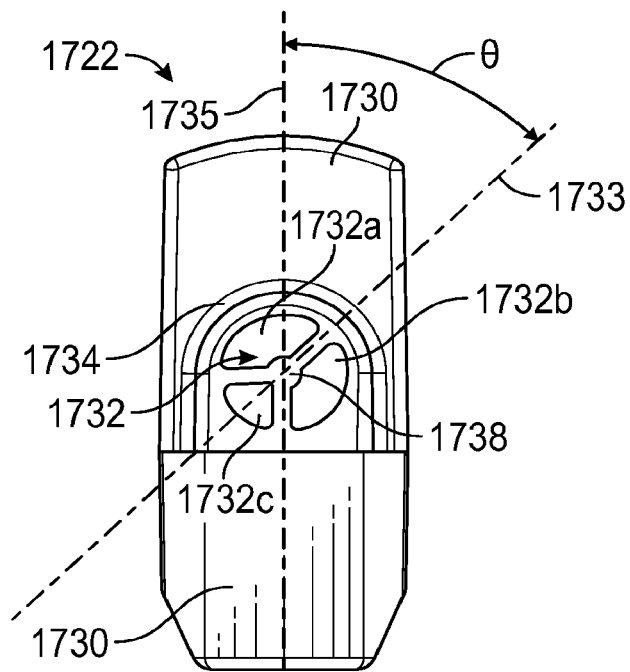

Referring to FIGS. 66-67, the coupling member 1722 can have a shaft portion 1728, a flange portion 1730 extending radially outwardly from the shaft portion 1728, and a lumen 1732 extending axially through the shaft portion 1728 from distal end to a proximal end of the coupling member 1722. In some embodiments, the shaft portion 1728 can have a projection or ridge 1734 that extends radially outwardly.

As shown FIG. 64, the connection member 1702 can extend partially over the shaft portion 1728 of the coupling member 1722 and the ridge 1734 can help prevent relative movement therebetween. The flange portion 1730 can be configured for connecting the coupling member 1722 to the housing 1704 (e.g., with a fastener 1736). The outer shaft 520 can extend into the distal end portion of the lumen 1732, and the actuation shaft 512 and the clasp control members 524 can extend from the proximal end of the outer shaft 520 and lumen 1730.

In certain embodiments, the coupling member 1722 can have a divider 1738 that divides the lumen 1732 into a plurality of segments. The divider 1738 can be disposed in a proximal end portion of the lumen 1732. In the illustrated embodiment, the divider 1738 is generally "Y"-shaped and thus divides the lumen 1732 into three segments 1732a, 1732b, 1732c. For example, the segment 1732a can be configured for receiving one of the clasp control members 524, the segment 1732b can be configured for receiving another of the clasp control members 524, and the segment 1732c can be configured for receiving the actuation shaft 512.

In particular embodiments, the divider 1738 can be configured to orient the outer shaft 520 (and thus the prosthetic spacer device which is coupled to the distal end portion of the outer shaft 520) relative to the coupling member 1722 (and thus the handle 1700) at a pre-determined rotational orientation. This can be accomplished by positioning an axis 1733 of the divider 1738 at an angle θ relative to an axis 1735 of the coupling member 1722. The angle θ between the axes 1733, 1735 can in the range of 0-360 degrees. In certain embodiments, the angle θ between the axes 1733, 1735 can in the range of 15-90 degrees. In one particular embodiment, the angle θ between the axes 1733, 1735 can about 45 degrees. The coupling member 1722 can be coupled to the outer shaft of the third catheter by aligning pairs of the clasp control lumens of the outer shaft (see e.g., the lumens 1304a-1304d of the outer shaft 1300 shown in FIG. 41) with respective segments 1732a, 1732b of the coupling member 1722. The coupling member 1722 together with the outer shaft can be coupled to the shaft guide member 1726 and the housing 1704. Because the coupling member 1722 can only be coupled to the shaft guide member 1726 and the housing 1704 in one rotational orientation (e.g., due to its asymmetrical shape), the rotational orientation of the coupling member 1722 thus determines the rotational orientation of the outer shaft relative to the handle 1700.

The pre-determined orientation between the outer shaft and the handle 1700 can, for example, be selected (e.g., via the angle θ) to rotationally align the prosthetic spacer device relative to the native anatomy when the prosthetic spacer device is coupled to the outer shaft 520 and advanced through a patient's vasculature to an implantation location. For example, for a delivery assembly (e.g., the prosthetic spacer device 200 and delivery apparatus 502 with the handle 1700) that is configured for implanting a prosthetic spacer device at a patient's native mitral valve via a transseptal delivery approach, the divider 1738 can be oriented with an angle θ that is about 45 degrees as shown in FIG. 67. When oriented in this manner, the prosthetic spacer device will be oriented relative to the native anatomy such that the anchors of the prosthetic spacer device are at least substantially rotationally aligned with the native leaflets of the mitral valve when the prosthetic spacer device is deployed from the sheath 518 and positioned coaxially to the mitral valve (see, e.g., FIGS. 20-23) and the handle 1700 is rotationally oriented such that the clasp actuation mechanism is facing upwardly (e.g., in the orientation shown in FIG. 62).

This can, for example, reduce the time a physician spends aligning the prosthetic spacer device during the implantation procedure. It can also improve efficiency and precision of the manufacturing process by reducing the amount of guesswork that is needed to orient the outer shaft 520 relative to the coupling member 1722.

The divider 1738 can also improve hemostatic sealing between the outer shaft 520 and the handle 1700, for example, by reducing leakage at the joints of sleeves 1740 (FIG. 65) (through which the clasp control members 524 extend) and the outer shaft 520.

As shown in FIG. 65, the stabilizer member 1724 can be coupled to a distal end portion of the shaft guide member 1726, such as by fasteners, adhesive, and/or other coupling means (e.g., tabs 1739). The stabilizer member 1724 can include a support portion 1741 that is spaced between the proximal end of the outer shaft 520 (FIG. 64) and a port 1743 in the distal end portion of the shaft guide member 1726. The stabilizer member 1724 can also include an opening 1742 through which the actuation shaft 512 and its sleeve 1744 can extend. In this manner, the stabilizer member 1724 can, for example, support the portions of the actuation shaft 512 and the sleeve 1744 that are disposed between the outer shaft 520 and the shaft guide member 1726. As such, the stabilizer member 1724 can, for example, reduce buckling or kinking of the actuation shaft 512 when actuating the anchor actuation mechanism 1706. This in turn improves the functionality and/or reliability of the anchor actuation mechanism 1706 and thus anchor actuation of the prosthetic spacer device.

It should be noted that the stabilizer member 1724 and the divider 1738 are not shown in FIG. 64 in order to better illustrate other components of the handle 1700.

The shaft guide member 1726 can include clasp control lumens 1746 (e.g., two in the illustrated embodiment), an actuation shaft lumen 1748, and a flushing lumen 1750. The clasp control members 524 can extend through the clasp control lumens 1746 and can be coupled to the clasp control mechanism 1708. The actuation shaft 512 can extend through the actuation shaft lumen 1748 and can be coupled to the anchor actuation mechanism 1706. The flushing lumen 1750 can be coupled to a first portion 1752 of a flushing tube (FIG. 64) and a second portion 1754 of the flushing tube (FIG. 63) of the flushing mechanism 1710 (FIG. 63).

The anchor actuation mechanism 1706 can be coupled to the actuation shaft 512. As mentioned above, the anchor actuation mechanism 1706 of the handle 1700 is configured to allow a user to actuate the actuation shaft 512 and thus the anchors of the prosthetic spacer device by either pushing/pulling the actuation knob 1712 of the anchor actuation mechanism 1706 while pressing the mode selector button 1714 or by rotating the actuation knob 1712 without pressing the mode selector button 1714.

Figure 68:
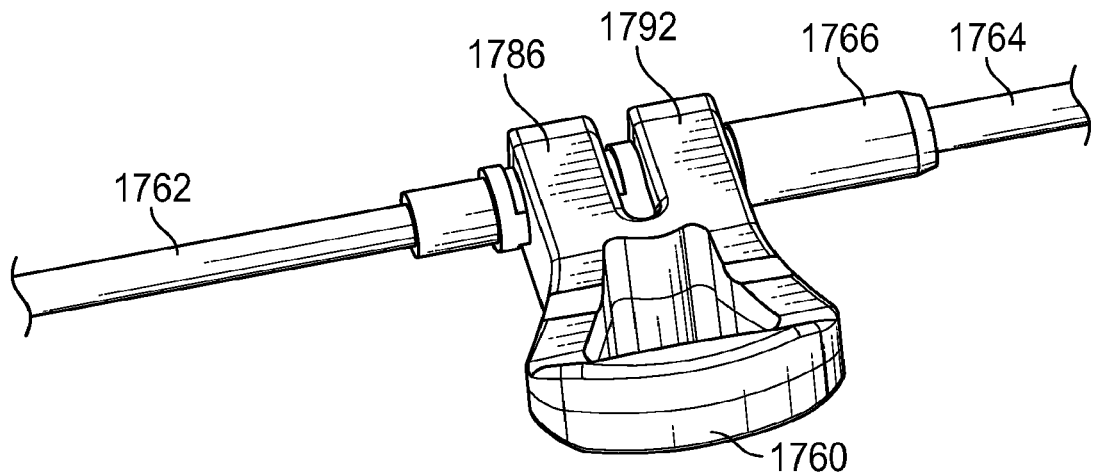
Figure 69:
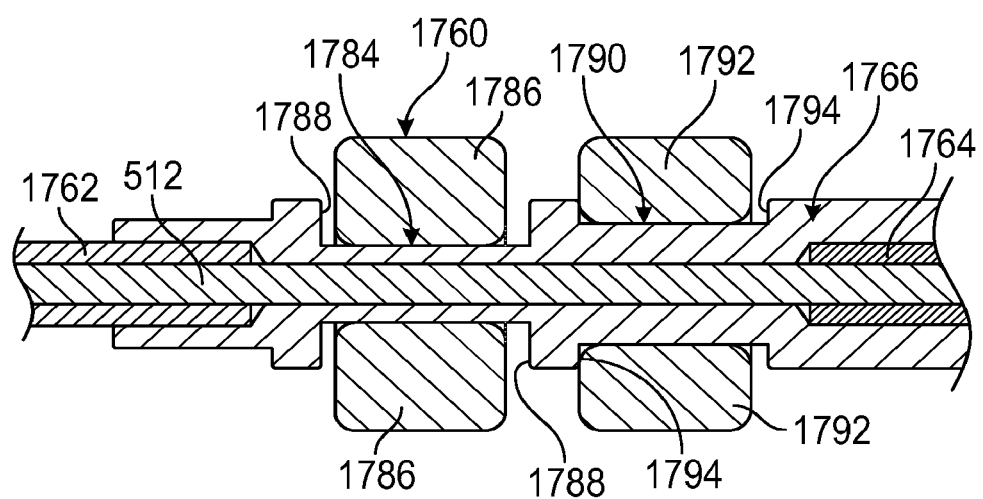
Figure 75:
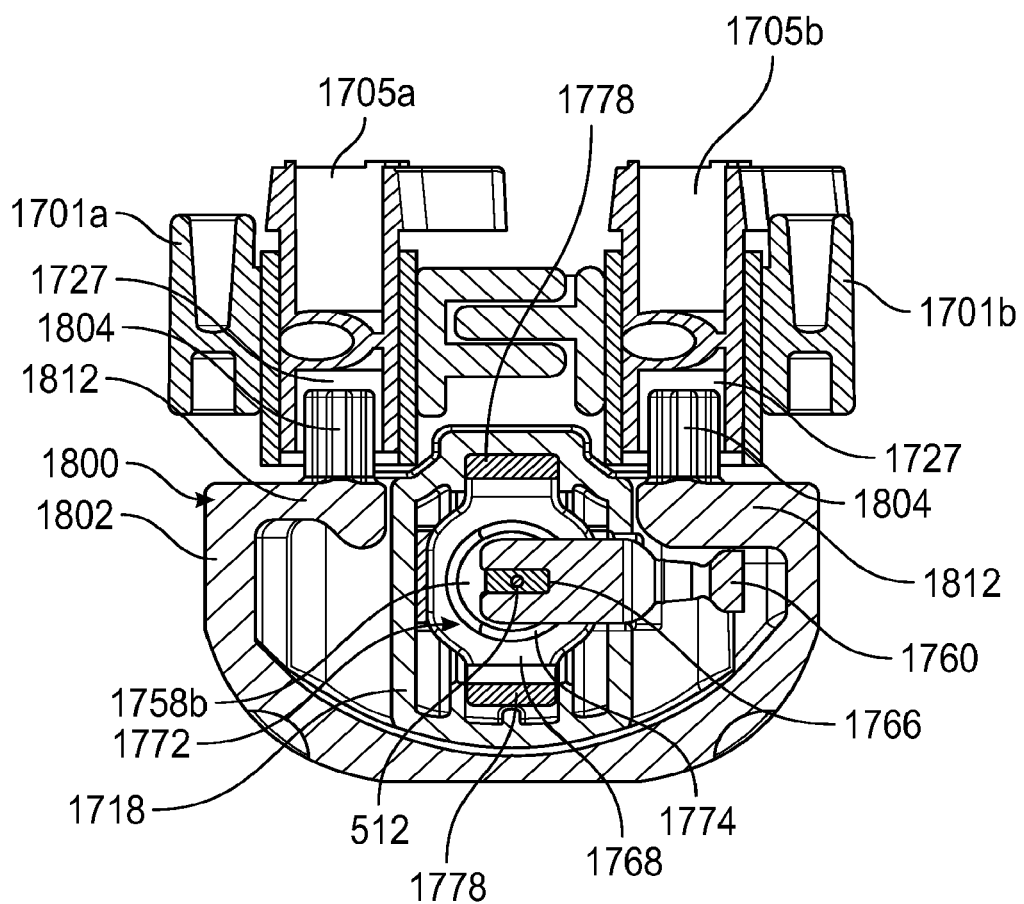

Referring to FIG. 62 and beginning at the proximal end portion and moving toward the distal end portion of the handle 1700, the anchor actuation mechanism 1706 can include a release knob 1756, the actuation knob 1712, a drive shaft 1758, the mode selector button 1714, and a release pin 1760. Referring to FIGS. 68-69, the anchor actuation mechanism 1706 (FIG. 62) can also include distal and proximal actuation sleeves 1762, 1764, respectively, and a ferrule 1766 coupled to and extending between the sleeves 1762, 1764. As shown in FIG. 69, the actuation shaft 512 can extend though and be fixedly coupled to the sleeves 1762, 1764 and the ferrule 1766. In this manner, the actuation shaft 512, the sleeves 1762, 1764, and the ferrule 1766 move together both axially and rotationally. Referring to FIG. 75, the anchor actuation mechanism 1706 can also include a bushing 1768. The components and operation of the actuation mechanism are further described below.

Referring again to FIG. 62, a proximal end portion 1758a of the drive shaft 1758 can be disposed outside of the housing 1704, and the actuation knob 1712 can be fixedly coupled thereto. The drive shaft 1758 can extend through a proximal opening 1770 of the housing 1704. Referring now to FIG. 75, the drive shaft 1758 can extend through an opening of the mode selector button 1714 (not shown, but see, e.g., the opening 1574 of the mode selector button 1546 shown in FIG. 52) and through an opening 1772 of the bushing 1768. The distal end portion 1758b of the drive shaft 1758 can be coupled to the bushing 1768 such that the drive shaft 1758 can rotate relative to the bushing 1768 but cannot move axially relative to the bushing 1768. This can be accomplished, for example, by coupling the distal end portion 1758b of the drive shaft 1758 to the bushing 1768 with fasteners (e.g., C-clips 1774) on the distal and proximal sides of the bushing 1768.

As shown in FIG. 62, the drive shaft 1758 can comprise a threaded portion 1776. The mode selector button 1714 (which is movably coupled to the housing 1704) can comprise a threaded portion configured to threadably engage the threaded portion 1776 of the drive shaft 1758 when the mode selector button 1714 is in a first mode of operation. In the first mode of operation, the drive shaft 1758 can be moved axially relative to the mode selector button 1714 by rotating the actuation knob 1712 relative to the housing 1704. In the illustrated embodiment, the threaded portions of the drive shaft 1758 and the mode selector button 1714 are "left-hand" threads. As such, rotating the drive shaft 1758 clockwise relative to the mode selector button portion 1714 moves the drive shaft 1758 proximally relative to the housing 1704, and rotating the drive shaft 1758 counterclockwise relative to the mode selector button portion 1714 moves the drive shaft 1758 distally relative to the housing 1704. In other embodiments, the threaded portions of the drive shaft 1758 and the mode selector button 1714 can be "right-hand" threads. In those embodiments, rotating the drive shaft 1758 counterclockwise relative to the mode selector button portion 1714 moves the drive shaft 1758 proximally relative to the housing 1704, and rotating the drive shaft 1758 clockwise relative to the mode selector button portion 1714 moves the drive shaft 1758 distally relative to the housing 1704.

The mode selector button 1714 can also comprise a non-threaded portion configured to engage the drive shaft 1758 when the mode selector button 1714 is in a second mode of operation. In the second mode of operation, the drive shaft 1758 can be moved axially relative to the mode selector button 1714 by pushing or pulling the actuation knob 1712 relative to the housing 1704. The mode selector button 1714 can be biased (e.g., with a biasing member such as a spring) to either the first mode of operation or the second mode of operation as the default mode of operation and can be moved from the default mode of operation to the other mode of operation by pressing the mode selector button 1714.

To help keep the drive shaft 1758 and the opening of the mode selector button 1714 coaxial as the drive shaft 1758 moves axially relative to the mode selector button 1714 in both the first and second modes of operation, the bushing 1768 and the housing 1704 can comprise respective mating features. For example, in the illustrated embodiment, the bushing 1768 comprises tabs or projections 1778 that can be disposed in respective slots of the housing 1704, as shown in FIG. 75. The tabs 1778 of the bushing 1768 and the slots of the housing 1704 allow the bushing 1768 and thus the drive shaft 1758 to move axially relative to the housing 1704 and the mode selector button 1714 and prevent lateral (e.g., left/right in the orientation shown in FIG. 75) and vertical (e.g., up/down in the orientation shown in FIG. 75) movement therebetween. As a result, the bushing 1768 helps to keep the drive shaft 1758 and the opening of the mode selector button 1714 coaxial. Maintaining coaxiality can, for example, reduce or prevent the drive shaft 1758 from binding relative to the mode selector button 1714 and/or promote smooth and controllable movement between the components.

Figure 71:
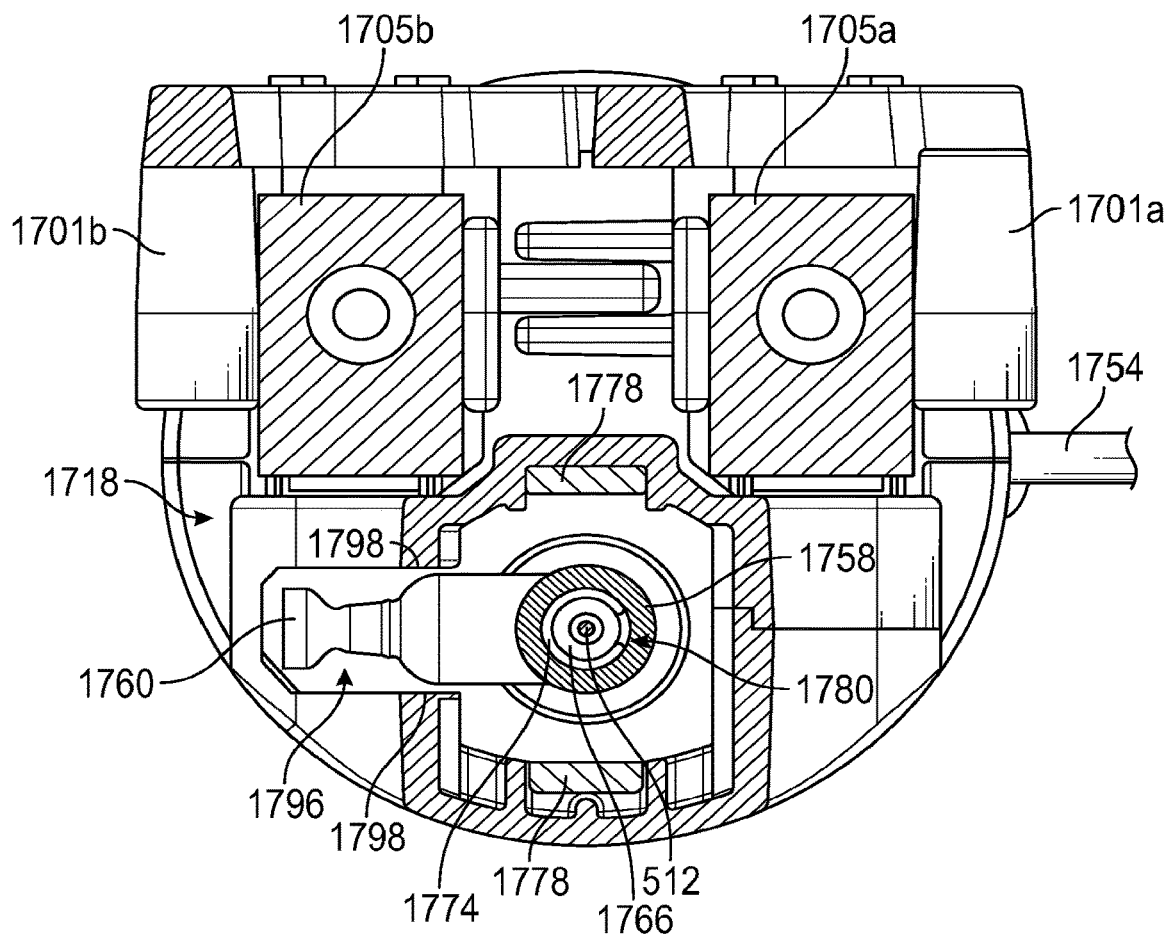

Referring to FIG. 62, the proximal end portion 512a (FIG. 15) of the actuation shaft 512 and/or the proximal sleeve 1764 (FIG. 69) can be fixedly secured (e.g., with a fastener, adhesive, etc.) to the release knob 1756. As best shown in FIG. 71, the drive shaft 1758 can have an axially extending lumen 1780 through which the actuation shaft 512, the sleeves 1762, 1764, and the ferrule 1766 can extend. The lumen of the drive shaft 1758 can be sized and/or configured such that the actuation shaft 512, the sleeves 1762, 1764, and the ferrule 1766 are movable (e.g., rotationally and axially) relative to the drive shaft 1758. This can be accomplished by forming the lumen 1780 of the drive shaft 1758 with an at least slightly larger diameter than the diameter of the actuation shaft 512, the sleeves 1762, 1764, and the ferrule 1766. The proximal sleeve 1764 and the drive shaft 1758 can be sized such that when the distal end portion of the release knob 1756 is disposed adjacent or contacting the proximal end portion of the actuation knob 1712 (e.g., as shown in FIG. 62), the ferrule 1766 (which is coupled to the distal end portion of the proximal sleeve 1764) is disposed adjacent the distal end portion 1758b of the drive shaft 1758.

From the ferrule 1766, the distal sleeve 1762 and the actuation shaft 512 can extend distally through the support portion 1718 of the housing 1704. As shown in FIGS. 64-65, the actuation shaft 512 can extend distally through the actuation shaft lumen 1748 of the shaft guide member 1726 and into the sleeve 1744. The sleeve 1744 and the actuation shaft 512 can exit the port 1743 of the shaft guide member 1726, extend through the opening 1742 of the stabilizer member 1724, and through the actuation shaft lumen 538 (FIG. 16) of the outer shaft 520. As shown in FIG. 12, the distal end portion 512b of the actuation shaft 512 can extend distally beyond the sleeve 1744 and the distal end portion 520b of the outer shaft 520 and can be threadably coupled to the distal collar 208 of the prosthetic spacer device 200.

With the actuation shaft 512 of the delivery apparatus 502 coupled to the distal collar 208 of the prosthetic spacer device 200, the actuation shaft 512 can be releasably coupled to the anchor actuation mechanism 1706 via the release pin 1760. This can be accomplished by inserting the release pin 1760 through a window 1782 of the support portion 1718 of the housing 1704 such that the release pin 1760 engages the ferrule 1766, as shown in FIG. 62.

Referring to FIGS. 68-69, the release pin 1760 and the ferrule 1766 can be configured so as to prevent relative movement (e.g., rotational and/or axial movement) therebetween when the release pin 1760 engages the ferrule 1766. For example, in some embodiments, the ferrule 1766 can comprise a first recessed portion 1784 having a non-circular (e.g., rectangular, hexagonal, etc.) cross-sectional profile taken in a plane perpendicular to the longitudinal axis of the ferrule. The first recessed portion 1784 can, in some instances, be referred to as "a flat." The release pin 1760 can have a first pair of jaws 1786 defining a non-circular first notch and configured for engaging a first recessed portion 1784 of the ferrule 1766. Engagement between the non-circular surfaces of the release pin 1760 and the ferrule 1766 can prevent relative rotational movement between the release pin 1760 and the ferrule 1766. Engagement between the first pair of jaws 1786 and shoulders 1788 of ferrule 1766 can prevent relative axial movement between the release pin 1760 and the ferrule 1766.

Referring still to FIGS. 68-69, the ferrule 1766 can optionally include a second recessed portion 1790 having a circular cross-sectional profile taken in a plane perpendicular to the longitudinal axis of the ferrule. The release pin 1760 can optionally have a second pair of jaws 1792 defining a circular second notch and configured for engaging the second recessed portion 1790 of the ferrule 1766. Therefore, engagement between the second pair of jaws 1792 and shoulders 1794 of ferrule 1766 can prevent relative axial movement between the release pin 1760 and the ferrule 1766. The circular configuration of the second recessed portion 1790 and the second pair of jaws 1792 can, for example, improve the ability of the release pin 1760 and/or the ferrule 1766 to bear an axial load because the surface area on which the second pair of jaws 1792 contacts the shoulders 1794 of the ferrule 1766 is relatively larger than the surface area on which first pair of jaws 1786 contacts the shoulders 1788 of the ferrule 1766.

The release pin 1760 can also prevent relative rotational movement between the actuation shaft 512 and the housing 1704 when the release pin is coupled to the ferrule 1766. This is because the release pin 1760 is disposed in a slot 1796 of the support portion 1718 of the housing 1704 that is defined by surfaces 1798. If a user tries to rotate the actuation shaft 512 via the release knob 1756, the release pin 1760 contacts the surfaces 1798 of the housing 1704, which prevent the release pin 1760 rotating relative to the housing 1704. Thus, when the release pin 1760 is coupled to the ferrule 1766, the release pin 1760 prevents the release knob 1756 from being rotated relative to the housing 1704, which in turn prevents the actuation shaft 512 from being released from the prosthetic spacer device 200.

The release pin 1760 and the release knob 1756 prevent relative axial movement between the actuation shaft 512 and the drive shaft 1758 when the release pin 1760 is coupled to the ferrule 1766. This is because the release knob 1756 (which is coupled to the actuation shaft 512 via the proximal sleeve 1764) contacts the proximal end portion 1758a of the drive shaft 1758, thereby preventing the actuation shaft 512 from moving distally relative to the drive shaft 1758, and because the release pin 1760 (which is coupled to the actuation shaft 512 via the ferrule 1766) contacts the distal end portion 1758b of the drive shaft 1758, thereby preventing the actuation shaft 512 from moving proximally relative to the drive shaft 1758. As a result, the actuation shaft 512 moves axially with the drive shaft 1758 when the release pin 1760 is coupled to the ferrule 1766. Moving the drive shaft 1758 distally relative to the housing 1704 urges the distal end portion 1758b of the drive shaft 1758 against the release pin 1760 and thus moves the actuation shaft 512 distally (e.g., to open the anchors 204 of the prosthetic spacer device 200). Moving the drive shaft 1758 proximally relative to the housing 1704 urges the proximal end portion 1758a of the drive shaft 1758 against the release knob 1756 and thus moves the actuation shaft 512 proximally (e.g., to close the anchors 204 of the prosthetic spacer device 200).

As the drive shaft 1758 and the actuation shaft 512 move axially relative to the housing 1704, the release pin 1760 slides axially within the slot 1796. In some embodiments, the release pin 1760 can be accessible to the user regardless of the axial position of the release pin 1760 relative to the housing 1704. In such embodiments, the user can remove the release pin 1760 from the ferrule 1766 at any time, which allows the actuation shaft 512 to move independently of the drive shaft 1758. This can be accomplished, for example, by dimensioning the window 1782 in the axial direction so that the release pin 1760 is accessible to the user regardless of the axial position of the drive shaft 1758.

Figure 70:
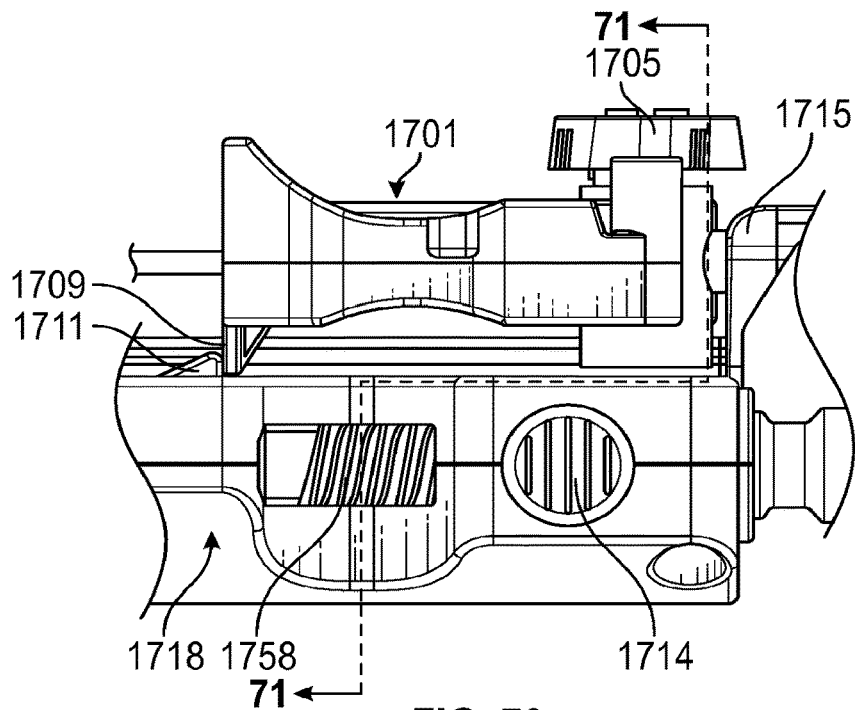

In other embodiments, the support portion 1718 of the housing 1704 can be configured such that the release pin 1760 is accessible to the user at one or more predetermined locations relative to the housing 1704 and/or concealed from the user at one or more other locations. For example, in the illustrated embodiment, the release pin 1760 is accessible to the user (via the window 1782 of the housing 1704) and therefore removable only when the actuation shaft 512 (via the drive shaft 1758) are in one predetermined location relative to the housing 1704, as shown in FIG. 62. This is because the window 1782 is only slightly larger than the release pin 1760. When the actuation shaft 512 is in other axial positions relative to the housing 1704, the release pin 1760 is not aligned with the window 1782 and thus concealed from the user by the housing 1704, as shown in FIGS. 70-71. In some embodiments, the predetermined location in which the release pin 1760 is accessible to the user can correspond to the proximal-most position of the drive shaft 1758. This position of the drive shaft corresponds to the position of the actuation shaft 512 that places the anchors 204 of the prosthetic spacer device 200 in the fully closed configuration (e.g., FIG. 25). In such embodiments, the housing 1704 therefore acts as an additional safeguard to reduce the likelihood that the user will release the actuation shaft 512 from the prosthetic spacer device 200 (by pulling the release pin 1760 and rotating the release knob 1756) before the anchors 204 of the prosthetic spacer device 200 are secured to the native leaflets of the patient's heart.

Figure 72:
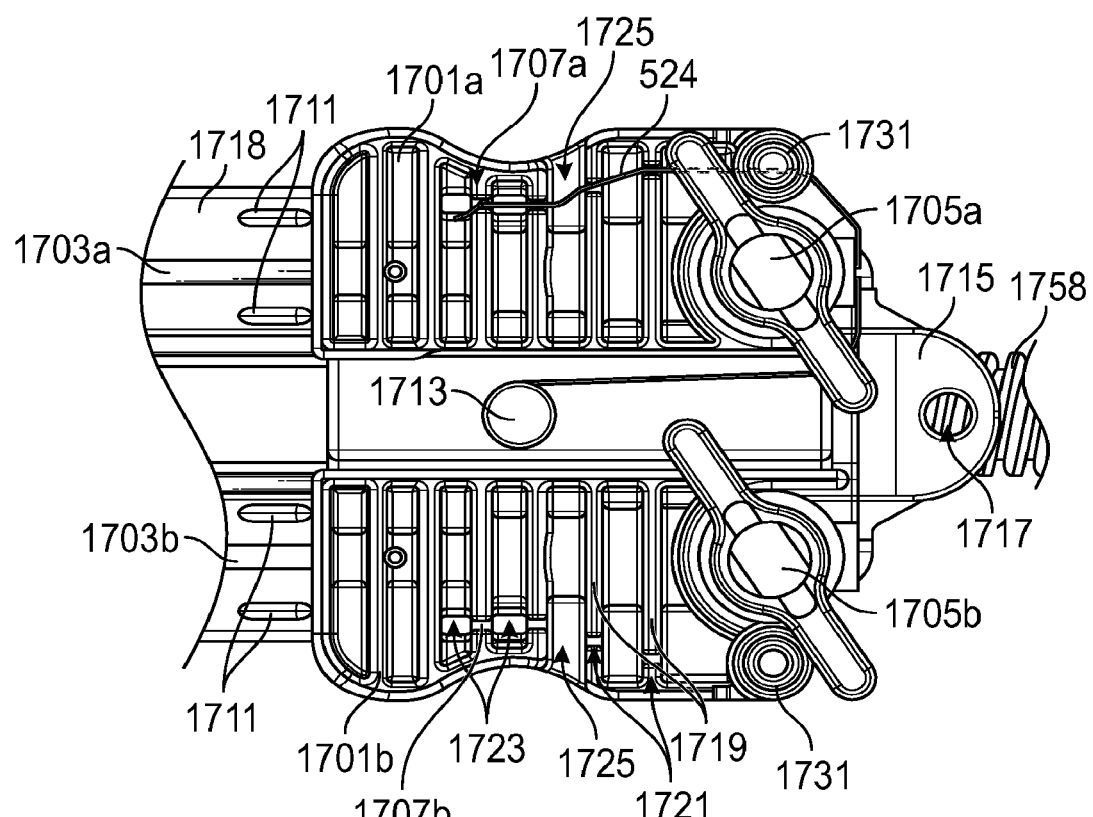

Referring to FIG. 72, the clasp actuation mechanism 1708 can include one or more clasp actuators 1701, one or more clasp tubes 1703, and one or more locking members 1705 (e.g., stopcocks). For example, in the illustrated embodiment, there are two of each of the clasp actuators 1701, the clasp tubes 1703, and the locking members 1705. These respective components are individually referred to as "17XXa" or "17XXb" (e.g., a first clasp actuator 1701a and a second clasp actuator 1701b) and collectively as "17XX" (e.g., the clasp actuators 1701). As best shown in FIG. 62, distal end portions of the clasp tubes 1703 can be movably coupled to the shaft guide member 1726 (FIG. 64) and extend proximally from the main body 1716 of the housing 1704 generally parallel to the support portion 1718 of the housing 1704. The clasp actuators 1701 can be fixedly coupled to proximal end portions of the clasp tubes 1703. The locking members 1705 can be fixedly coupled to the clasp actuators 1701.

Referring to FIG. 72 and FIGS. 64-65, each of the clasp control members 524 (only one shown in FIG. 72 in order to show other features of the clasp actuators 1701) can form a loop that extends through from a respective clasp actuator 1701, through a respective locking member 1705, through a lumen (not shown) of the clasp actuator 1701, through a respective clasp tube 1703, through a respective clasp control lumen 1746 of the shaft guide member 1726, through a respective sleeve 1740, through a respective lumen 540 (FIG. 16) of the outer shaft 520, through an opening 238 (FIG. 15) of a respective clasp 206 of the prosthetic spacer device 200, and then return back to the clasp actuator 1701 following the same general path but in reverse order (though the ends of each clasp control member 524 passes through a different lumen 540 of the outer shaft 520, as further described above).

The locking members 1705 can be used to secure the clasp control members 524 and their tension relative to the clasp actuation mechanism 1708. As such, moving the clasp actuators distally decreases tension on the clasp control members 524 (which closes the clasps 206 of the prosthetic spacer device 200), and moving the clasp actuators proximally increases tension on the clasp control members 524 (which opens the clasps 206 of the prosthetic spacer device 200).

Referring to FIG. 70, the clasp actuators 1701 can also include retention members 1709 that are configured to engage holding elements 1711 disposed on the support portion 1718 of the housing 1704. The retention members 1709 and the holding elements 1711 can be configured to selectively retain the clasp actuators 1701 in the proximal position, which corresponds to the open position of the clasps 206 of the prosthetic spacer device 200. These features can help prevent the clasps 206 from inadvertently closing, for example, due to the tension on the clasp control members 524 caused by the bias of the clasps 206 toward closed position which may cause the clasp actuators 1701 to move distally or due to a user accidentally pushing the clasp actuators 1701 distally.

The first and second clasp actuators 1701a, 1701b can be selectively coupled together (e.g., with the pin 1713) such that the clasp actuators can be moved together (e.g., when the pin 1709 is inserted through the clasp actuators) or individually (e.g., when the pin 1709 is removed from the clasp actuators).

In some embodiments, the support portion 1718 of the housing 1704 can also have a stopper 1715 disposed at the proximal end of the support portion 1718, as shown in FIG. 70. The stopper 1715 can, for example, limit movement of the clasp actuators 1701 in the proximal direction. Referring to FIG. 72, in certain embodiments, the stopper 1715 can have an opening 1717 formed therein. The opening 1717 can be configured for receiving and storing the pin 1713 when the pin 1713 is removed from the clasp actuators 1701 (e.g., for individual clasp actuation).

The clasp actuators 1701 can also include one or more optional features configured for securing the ends of the clasp control members 524 to the clasp actuators 1701 and/or for releasing the ends of the clasp control members 524 from the clasp actuators 1701. For example, as shown in FIG. 72, each clasp actuator 1701 can have one or more ridges 1719 with notches 1721 formed therein and/or one or more bosses 1731 with channels extending therethrough. One end of the clasp control members 524 can extend from a respective locking member 1705, through a channel of the boss 1731, and through the notches 1721. In this manner, the channel and the notches 1721 can act as guides for the clasp control members 524. This can, for example, reduce the likelihood that the clasp control members 524 will become entangled with another component of the handle 1700 (e.g., the locking members 1705). Each clasp actuator 1701 can also have a plurality of spaced-apart openings 1723 (e.g., two in the illustrated embodiment) with a post 1707 therebetween. In this manner, one end of each of the clasp control members 524 can be wrapped around and secured (e.g., tied) to the post 1707 of a respective clasp actuators 1701.

The other end of each of the clasp control members 524 can extend from a respective locking member 1705 and can be coupled (e.g., tied) to the pin 1713. Each of the clasp actuators 1701 can have an access point (e.g., a slot 1725) for accessing a respective clasp control member 524 in order to release it from the clasp actuator 1701. The access point can be disposed between the coupling location (e.g., the openings 1723) and the locking member 1705. As a result, the slot 1725 can, for example, provide a location in which the user can access and cut the clasp control member 524 with a cutting tool such as a scalpel.

The clasp control members 524 can be secured to the clasp actuators 1701 and/or the pin 1713 in various other ways, such as with adhesive, clips, knots, and/or other securing means.

It should be noted only one clasp control member 524 (which is coupled to the clasp actuator 1701a) is shown in FIG. 72. This is to better illustrate the ridges 1719, notches 1721, openings 1723, and slots 1725 of the clasp actuator 1701b, which can also have another clasp control member 524 coupled to and extending therethrough.

Figure 73:
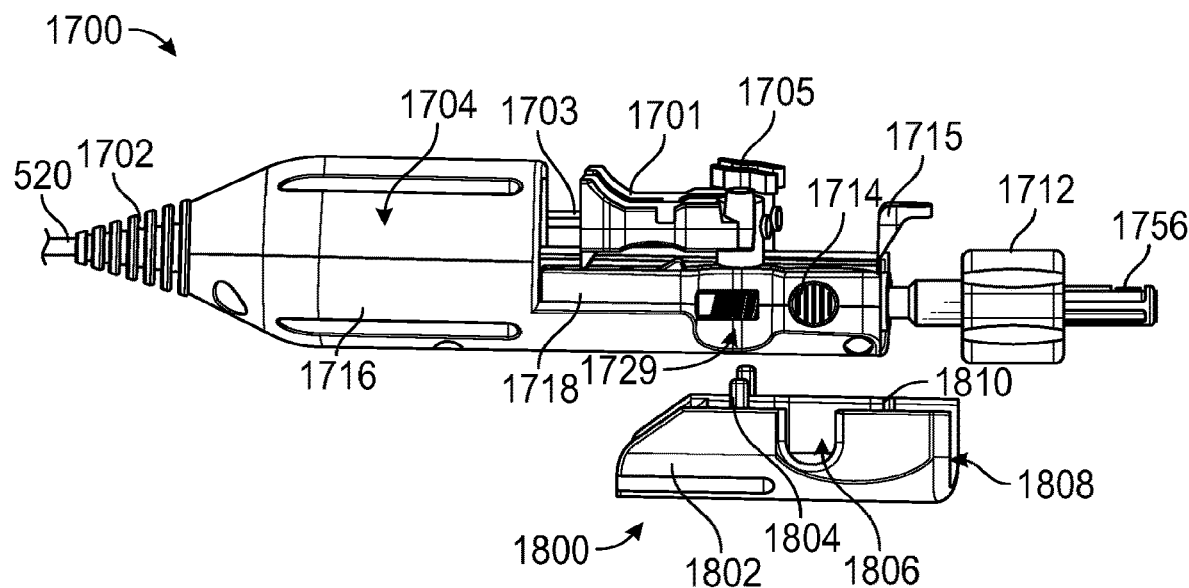
Figure 74:
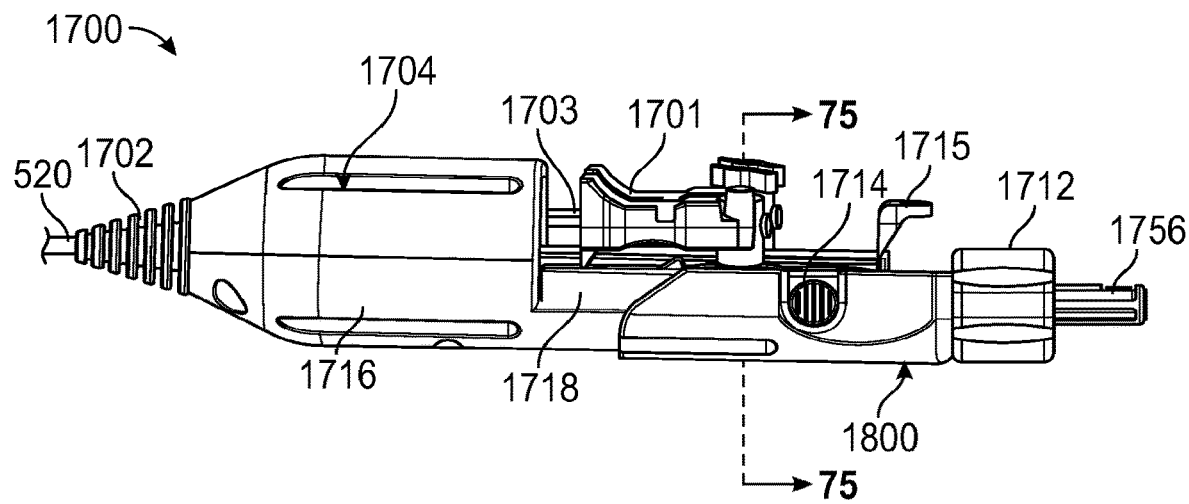

FIGS. 73-75 show an exemplary embodiment of a clasp positioning tool 1800 being used, optionally, with the handle 1700. The clasp positioning tool 1800 can be used, for example, to position a clasp actuation mechanism of a handle at a predetermined position relative to an anchor actuation mechanism of the handle while a user removes slack and sets the tension in clasp control members. As such, the clasp positioning tool 1800 can help to ensure consistent and precise tension in the clasp control members.

Although the clasp positioning tool 1800 described herein as being used with the handle 1700, the clasp positioning tool 1800 can be used and/or adapted for use with various other handles (including the handles 522, 700, 1500, and/or 1600) and/or the handles can be adapted for use with the clasp positioning tool 1800.

Referring to FIG. 73, the clasp positioning tool 1800 can include a main body 1802 and one or more projections 1804 (e.g., two in the illustrated embodiment) extending from the main body 1802. Generally speaking, the main body 1802 can be configured for releasably coupling the clasp positioning tool 1800 to the housing 1704 and for positioning the anchor actuation mechanism 1706 relative to the housing 1704, and the projections 1804 can be configured for releasably coupling the clasp positioning tool 1800 to the clasp actuation mechanism 1708 and for positioning the clasp actuation mechanism 1708 relative to the housing 1704.

The main body 1802 of the clasp positioning tool 1800 can comprise a first opening 1806 formed in a side portion and a second opening 1808 formed in a proximal end portion. The first opening 1806 can be configured to provide access to the mode selector button 1714 of the handle 1700, as shown in FIG. 74. The second opening 1808 can be configured such that the drive shaft 1758 of the anchor actuation mechanism 1706 can extend therethrough and such that the actuation knob 1712 cannot extend therethrough, as also shown in FIG. 74. In this manner, the main body 1802 can limit movement of the actuation shaft 1758 in the distal direction when the actuation knob 1712 abuts the proximal end of the main body 1802 adjacent the second opening 1808.

Referring again to FIG. 73, the main body 1802 can include a lip or shoulder 1810 that is spaced from the proximal end of the main body 1802. The lip or shoulder 1810 can be configured to engage the proximal end of the support portion 1718 of the housing 1704. Accordingly, the lip 1810 can limit movement of the clasp positioning tool 1800 relative to the housing 1704 in the distal direction.

Referring to FIG. 75, the main body 1802 can also have one or more flange portions 1812 that extend radially inwardly. The flange portions 1812 can be configured for releasably coupling the clasp positioning tool 1800 to the handle 1700, as further described below.

The projections 1804 can extend outwardly (e.g., vertically in the orientation shown in FIG. 75) from the flange portions 1812 of the main body 1802. The projections 1804 can be configured to extend into openings 1727 of the locking members 1705 of the clasp actuation mechanism 1708. In this manner, the projections 1804 can limit movement of the clasp actuators 1701 relative to the housing 1704 in distal direction.

To provide access to the openings 1727 of the locking members 1705 of the handle 1700, the support portion 1718 of the housing 1704 can have recesses 1729 formed therein, as best shown in FIG. 63. The recesses 1729 can be axially aligned with the window 1782 of the housing 1704.

The clasp positioning tool 1800 can be coupled to the handle 1700 by axially aligning the openings 1727 (FIG. 63) of the locking members 1705 with the recesses 1729 of the housing 1704 and by moving the actuation mechanism 1706 distally such that the release pin 1760 is not aligned with the window 1782 of the housing 1704, as shown in FIG. 73. The projections 1804 of the clasp positioning tool 1800 can then be inserted into the openings 1727, as shown in FIG. 74. The clasp positioning tool 1800 can be secured or locked to the handle 1700 (e.g., for shipping) by moving the actuation mechanism 1706 proximally such that the release pin 1760 is aligned with the window 1782 of the housing 1704 and thus with the flanges 1812 of the clasp positioning tool 1800, as shown in FIG. 73. In the locked configuration, the release pin 1760 prevents the clasp positioning tool 1800 from being removed from the openings 1727 of the locking members 1705 because the release pin 1760 obstructs one of the recesses 1729 of the housing 1704 and contacts one of the flanges 1812 of the clasp positioning tool 1800. Although not shown, when the actuation knob 1712 is aligned with the window 1782, the actuation knob 1712 is spaced from the proximal end of the clasp positioning tool 1800.

As mentioned above, the handle 1700 can be a part of a delivery apparatus (e.g., the delivery apparatus 502, 1404), which, together with a prosthetic spacer device (e.g., the prosthetic spacer device 200, 1402), can form at least part of a delivery assembly. An exemplary method of assembling the delivery assembly and using the handle 1700 and the clasp positioning tool 1800 are described below.

The clasp control members 524 of the delivery apparatus 502 can be coupled to the clasps 206 of the prosthetic spacer device 200 by looping the clasp control members 524 through the openings 234 of the clasps 206 (see FIG. 15). The clasp control members 524 can be secured to the handle 1700 via the locking member 1705 and the clasp actuators 1701 (see FIG. 72). At this point, the clasps 206 of the prosthetic spacer device 200 can be opened and closed by moving the clasp actuators 1701 proximally and distally, respectively. The outer shaft 520 of delivery apparatus 502 can be coupled to the proximal collar 210 of the prosthetic spacer device 200 via the coupler 514 and actuation shaft 512 of the delivery apparatus (see FIGS. 12-14). The actuation shaft 512 of the delivery apparatus 502 can be coupled to the distal collar 208 of the prosthetic spacer device 200 by inserting the distal end portion 512*b* of the actuation shaft 512 into the bore 226 of the distal collar 208 and rotating the release knob 1756 in a first direction (e.g., clockwise) relative to the prosthetic spacer device 200 (see FIGS. 14 and 62). At this point, the anchors 204 of the prosthetic spacer device 200 can be opened and closed by moving the release knob 1756 distally and proximally, respectively.

With the delivery apparatus 502 and the prosthetic spacer device 200 releasably coupled together, the actuation shaft 512 can be releasably coupled to the anchor actuation mechanism 1706 of the handle 1700. This can be accomplished, for example, with at least some of the following acts. The actuation knob 1712 can be positioned such that the distal end portion 1758*b* of the drive shaft 1758 is disposed proximal relative to the window 1782 of the housing 1704 (see FIG. 62). This can be achieved by rotating the actuation knob 1712 in the first direction (e.g., clockwise) relative to the housing 1704 and/or by pressing the mode selector button 1714 and moving the actuation knob 1712 proximally relative to the housing 1704. The ferrule 1766 (which is coupled to the actuation shaft 512 and the release knob 1756) can be exposed from the lumen 1780 of the drive shaft 1758 and axially aligned with the window 1782 of the housing 1704 by positioning the distal end of the release knob 1756 adjacent the proximal end of the actuation knob 1712. With the drive shaft 1758 and the ferrule 1766 in this position, the release pin 1760 can be coupled to the ferrule 1766 by inserting the release pin 1760 through the window 1782 of the housing 1704 (see FIG. 62) and urging the jaws 1786, 1792 of the release pin 1760 over the respective recessed portions 1784, 1790 of the ferrule 1766 (see FIG. 68). With the release pin 1760 coupled to the ferrule 1766, the actuation shaft 512 (and thus the anchors 204 of the prosthetic spacer device 200) moves axially with the drive shaft 1758 of the anchor actuation mechanism 1706.

Once the actuation shaft 512 is coupled to the anchor actuation mechanism 1706, rotating the actuation knob 1712 in a second direction (e.g., counterclockwise) relative to the housing 1704 and/or pressing the mode selector button 1714 and moving the actuation knob 1712 distally relative to the housing 1704 results in the anchors 204 moving toward the open configuration (see FIG. 20). Rotating the actuation knob 1712 in the first direction (e.g., clockwise) relative to the housing 1704 and/or by pressing the mode selector button 1714 and moving the actuation knob 1712 proximally relative to the housing 1704 results in the anchors 204 moving toward the closed position (see FIG. 25).

The clasp positioning tool 1800 can be coupled and secured to the handle 1700 as described above (see FIGS. 73-75). An assembly comprising the delivery apparatus, the prosthetic spacer device, and the clasp positioning tool 1800 can be packaged and/or delivered to a user in this configuration.

To prepare the delivery assembly for implantation, the user can remove slack and/or adjust the tension of the clasp control members 524 with the clasp positioning tool 1800. This can be accomplished by moving the drive shaft 1758 of the handle 1700 distally from proximal-most position (which is used to secure the clasp positioning tool 1800 to the handle 1700 due to the release pin 1760 axially aligning with the flange 1812 of the clasp positioning tool 1800 until the distal end of the actuation knob 1712 contacts the proximal end of the clasp positioning tool 1800. This can be accomplished by rotating the actuation knob 1712 in the second direction (e.g., counterclockwise) relative to the housing 1704 and/or pressing the mode selector button 1714 and moving the actuation knob 1712 distally relative to the housing 1704. This moves the anchors 204 of the prosthetic spacer device 200 from the fully closed configuration (e.g., FIG. 25) to an at least partially open configuration (e.g., FIG. 23). With the anchors 204 in this position, the user can open the locking members 1705 of the clasp actuation mechanism 1708 and remove slack and/or otherwise adjust the tension of the clasp control members 524. The users can then retain the desired tension on the clasp control members 524 by closing the locking members 1705, which prevents the clasp control members 524 from moving relative to the clasp actuation mechanism 1708 of the handle 1700. Both of the first end portions of the clasp control members 524 can then be coupled (e.g., tied) to the pin 1713 of the clasp actuation mechanism 1708 (see FIG. 72). Each of the second end portions of the clasp control members 524 can be coupled to a respective clasp actuator 1701 by positioning the clasp control member 524 in the notches 1721, looping the clasp control member 524 through openings 1723, and tying the clasp control member 524 to itself. Securing the end portions of the clasp control members 524 can, for example, reduce the risk that the clasp control members 524 will be released from the clasps 206 even if the locking members 1705 are opened. Separating the ends of each clasp control member 524 from each other (i.e., by tying one end to the clasp actuators 1701 and the other end to the pin 1713), can make it easier to cut the clasp control members 524 (e.g., during the release procedure).

The clasp positioning tool 1800 can be removed from the handle 1700 by withdrawing the projections 1804 of the clasp positioning tool 1800 from the openings 1727 of the handle 1700 and by removing the main body 1802 from the housing 1704 of the handle 1700.

The flushing mechanism 1710 can be used to flush the delivery assembly (e.g., with a saline solution).

The prosthetic spacer device 200 can be positioned in the delivery configuration by moving the actuation knob 1712 and the clasp actuators 1701 to the distal-most position. This elongates the anchors 204 and closes the clasps 206 (see FIG. 20).

The prosthetic spacer device 200, which is coupled to the third catheter 508 (FIG. 11), can be inserted through the first and second catheters 504, 506 (see FIG. 11) and positioned adjacent an implantation location (see FIG. 20). The catheters 504, 506, 508 (including the handle 1700) can be used to position the prosthetic spacer device 200 relative to native heart valve leaflets (see FIGS. 20-22).

At the implantation location, the anchor actuation mechanism 1706 of the handle 1700 can be used to manipulate the anchors 204 of the prosthetic spacer device 200 between the elongate, delivery configuration (e.g. FIG. 20), a positioning configuration (e.g., FIG. 22), and a leaflet-capture configuration (e.g., FIG. 23). Rotating the actuation knob 1712 in the first direction (e.g., clockwise) relative to the housing 1704 and/or pressing the mode selector button 1714 and moving the actuation knob 1712 proximally relative to the housing 1704 closes the anchors 204, and rotating the actuation knob 1712 in the second direction (e.g., counterclockwise) relative to the housing 1704 and/or pressing the mode selector button 1714 and moving the actuation knob 1712 distally relative to the housing 1704 opens the anchors 204.

Figure 21:
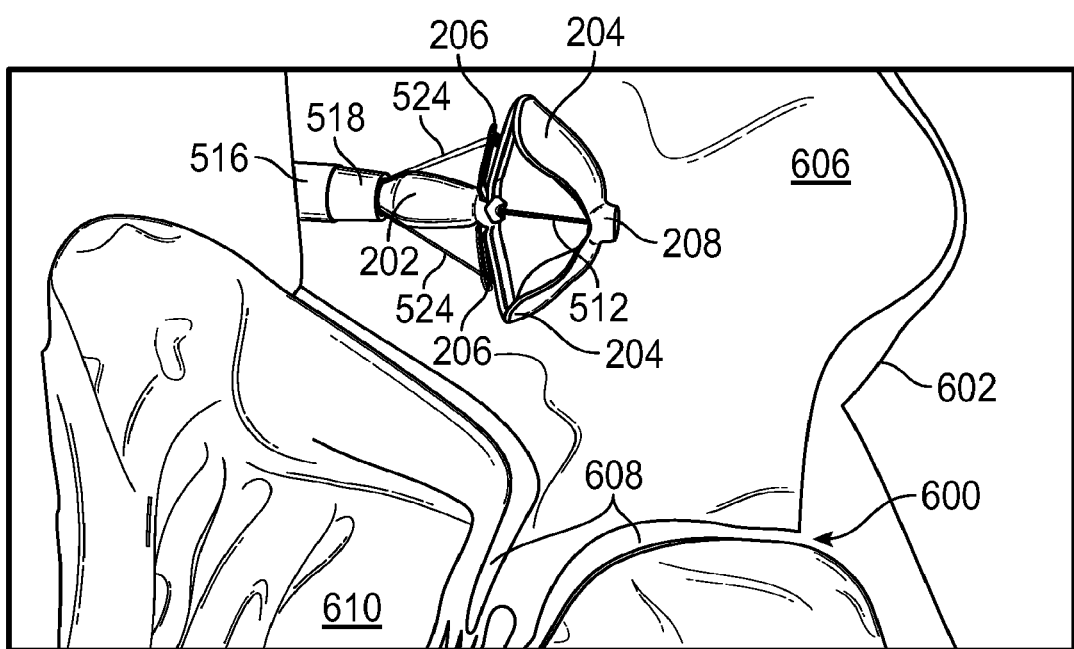

With the anchors 206 of the prosthetic spacer device 200 positioned behind respective native leaflets, the clasp actuation mechanism 1708 of the handle 1700 can be used to manipulate the clasps 206 of the prosthetic spacer device 200 between the closed configuration (e.g., FIGS. 20-22 shows the clasps 206 in the closed configuration) and the open configuration (e.g., FIG. 23 shows the clasps 206 in the open configuration) to capture the native leaflets within a respective clasp 206. Moving the clasp actuators 1701 proximally relative to the housing 1704 opens the clasps 206 of the prosthetic spacer device 200. Moving the clasp actuators 1701 distally relative to the housing 1704 closes the clasps 206 of the prosthetic spacer device 200. Positioning the clasp actuators 1701 such that the retention members 1709 of the clasp actuators 1701 are disposed proximally relative to the holding elements 1711 of the housing 1704 retains the clasp actuators 1701 in the proximal-most position, which retains the clasps 206 of the prosthetic spacer device 200 in the open configuration. Lifting the clasp actuators 1701 over the holding elements 1711 of the housing 1704 and moving the clasp actuators 1701 from the proximal-most position allows the clasp actuators 1701 to move freely relative to the housing, which allows opening and closing of the clasps 206 of the prosthetic spacer device 200. Both clasps 206 of the prosthetic spacer device 200 can manipulated simultaneously when the clasp actuators 1701 are coupled together by the pin 1713 (FIG. 72). Each clasp 206 of the prosthetic spacer device 200 can be manipulated independently when the pin 1713 is removed from the clasp actuators 1701.

Once the native leaflets are captured within respective clasps 206 of the prosthetic spacer device 200, the anchor actuation mechanism 1706 of the handle 1700 can be used to manipulate the anchors 204 of the prosthetic spacer device 200 from the leaflet-capture configuration (e.g., FIGS. 23-24) to a closed configuration (e.g., FIG. 25). This can be accomplished by rotating the actuation knob 1712 in the first direction (e.g., clockwise) relative to the housing 1704 and/or pressing the mode selector button 1714 and moving the actuation knob 1712 proximally relative to the housing 1704. This in turn draws the native leaflets inwardly toward the spacer member 202 of the prosthetic spacer device 200, as shown in FIG. 25.

The user can re-open the anchors 204 and/or the clasps 206 to reposition and/or retrieve the prosthetic spacer device 200 by manipulating the anchor actuation mechanism 1706 and/or the clasp actuation mechanism 1708.

Once the spacer device 200 is implanted at the desired location, the user can release the delivery apparatus from the prosthetic spacer device 200. One aspect of the release procedure is releasing the clasp control members 524 from the clasps 206. This can be accomplished by opening the locking members 1705 of the handle 1700. The user can cut the second end portions of the clasp control members 524 free from their respective clasp actuator 1701 by inserting a scalpel into the slots 1725 (FIG. 62) of the clasp actuators 1701 and into contact with the clasp control members 524. The user can then pull on the first end portions of the clasp control members 524 at least until the second end portions withdraw from the openings 234 of the clasps 206 of the prosthetic spacer device 200.

A second aspect of the release procedure is releasing the distal end portion 512b of the actuation shaft 512 from the distal collar 208 of the prosthetic spacer device 200. This can be accomplished by moving the actuation knob 1712 to the proximal-most position relative to the housing 1704. This axially aligns the release pin 1760 with the window 1782 of the housing 1704, which ensures that the anchors 204 of the prosthetic spacer device 200 are in the fully closed configuration. The user can grasp the release pin 1760 and separate it from the ferrule 1766 by withdrawing it through the window 1782 of the housing 1704. With the release pin 1760 removed, the actuation shaft 512 and thus the release knob 1756 can rotate relative to the housing and can move proximally relative to the housing 1704, the drive shaft 1758, and the actuation knob 1712. The user can therefore remove the actuation shaft 512 from the distal collar 208 of the prosthetic spacer device 200 by rotating the release knob 1756 of the handle 1700 in the second direction (e.g., counterclockwise) relative to the housing 1704.

A third aspect of the release procedure is releasing the outer shaft 520 from the proximal collar 210 of the prosthetic spacer device 200. This can be accomplished by moving the release knob 1756 of the handle 1700 proximally until the distal end portion 512b of the actuation shaft 512 is disposed proximal to the coupler 514 of the delivery apparatus and then moving the housing 1704 of the handle 1700 (and thus the outer shaft 520) proximally relative to the prosthetic spacer device 200.

With the delivery apparatus released from the prosthetic spacer device 200, the catheters 504, 506, 508 of the delivery apparatus 504 can be removed from the patient.

The features described herein with regard to any example can be combined with other features described in any one or more of the other examples, unless otherwise stated. For example, the features of the prosthetic spacer device 100 can be combined with the prosthetic spacer device 200, and vice versa. As another example, any one or more of the features of a handle of a delivery apparatus (e.g., the handles 522, 700, 1500, 1600, and/or 1700) can be combined with any one or more of the features of another handle.

In view of the many possible embodiments to which the principles of the disclosure may be applied, it should be recognized that the illustrated embodiments are only preferred examples and should not be taken as limiting the scope of the claims. Rather, the scope of the claimed subject matter is defined by the following claims and their equivalents.

The invention claimed is:

1. A delivery system comprising:
   an elongate shaft having a proximal portion and a distal portion;
   a handle connected to the proximal portion of the elongate shaft;
   a first clasp control member that extends into the distal portion of the elongate shaft, through at least a portion of the elongate shaft, out of the proximal portion of the elongate shaft, and through the handle;
   a second clasp control member that extends into the distal portion of the elongate shaft, through the elongate shaft, out of the proximal portion of the elongate shaft, and through the handle;
   an actuator coupled to the handle, the actuator comprising
      a first side portion connected to the first clasp control member; and
      a second side portion connected to the second clasp control member;
   wherein the first side portion and the second side portion are releasably couplable such that when the first side portion and the second side portion are coupled, proximal movement of the actuator proximally pulls both the first clasp control member and the second clasp control member, and such that when the first side portion and the second side portion are uncoupled, individual proximal movements of the first side portion and the second side portion independently pull the first clasp control member and the second clasp control member, respectively.

2. The delivery system of claim 1 wherein the first clasp control member comprises a suture.

3. The delivery system of claim 1 wherein the first side portion and the second side portion are releasably connected by a pin.

4. The delivery system of claim 1 wherein the first side portion and the second side portion are constrained to proximal and distal movement relative to one another when the first side portion and the second side portion are released.

5. The delivery system of claim 1 wherein the first clasp control member extends through a first control member lumen in the handle, and the second clasp control member extends through a second control member lumen in the handle.

6. The delivery system of claim 5 wherein at least a portion of the first control member lumen extends proximally at an angle toward the second control member lumen.

7. The delivery system of claim 1 wherein the elongate shaft is flexible.

8. The delivery system of claim 1 further comprising an anchor actuation shaft in a lumen of the elongate shaft, wherein the anchor actuation shaft extends out of the proximal portion of the elongate shaft, and wherein the anchor actuation shaft extends out of the distal portion of the elongate shaft.

9. A delivery assembly comprising:
   a first clasp that is moveable between an open position and a closed position, wherein the first clasp is configured to be securable to a first native valve leaflet by moving the first clasp from the open position to the closed position of the first clasp;
   a first clasp control member coupled to the first clasp, wherein applying tension to the first clasp control member moves the first clasp to the open position;
   a second clasp that is moveable between an open position and a closed position, wherein the second clasp is configured to secure a second native valve leaflet by moving the second clasp from the open position to the closed position of the second clasp;
   a second clasp control member coupled to the second clasp, wherein applying tension to the second clasp control member moves the second clasp to the open position;

an elongate shaft having a proximal portion and a distal portion;

a handle connected to the proximal portion of the elongate shaft;

wherein the first clasp control member extends from the first clasp, into the distal portion of the elongate shaft, through the elongate shaft, out of the proximal portion of the elongate shaft, and through the handle;

wherein the second clasp control member extends from the second clasp, into the distal portion of the elongate shaft, through the elongate shaft, out of the proximal portion of the elongate shaft, and through the handle;

an actuator coupled to the handle, the actuator comprising
- a first side portion connected to the first clasp control member; and
- a second side portion connected to the second clasp control member;

wherein the first side portion and the second side portion are releasably couplable such that when the first side portion and the second side portion are coupled, proximal movement of the actuator proximally tensions both the first clasp control member and the second clasp control member to move both the first and second clasps to the open position, and such that when the first side portion and the second side portions are uncoupled, individual proximal movements of the first side portion and the second side portion individually tension the first clasp control member and the second clasp control member to independently open the first and second clasps, respectively.

10. The delivery assembly of claim 9 wherein the first clasp control member comprises a suture.

11. The delivery assembly of claim 9 wherein the first side portion and the second side portion are releasably connected by a pin.

12. The delivery assembly of claim 9 wherein the first side portion and the second side portion are constrained to proximal and distal movement relative to one another when the first side portion and the second side portion are released.

13. The delivery assembly of claim 9 wherein the first clasp control member extends through a first control member lumen in the handle, and the second clasp control member extends through a second control member lumen in the handle.

14. The delivery assembly of claim 13 wherein at least a portion of the first control member lumen extends proximally at an angle toward the second control member lumen.

15. The delivery assembly of claim 9 wherein the elongate shaft is flexible.

16. The delivery assembly of claim 9 wherein the first clasp and the second clasp are coupled to a spacer.

17. The delivery assembly of claim 9 further comprising an anchor actuation shaft in a lumen of the elongate shaft, wherein the anchor actuation shaft extends out of the proximal portion of the elongate shaft, and wherein the anchor actuation shaft extends out of the distal portion of the elongate shaft.

18. A delivery assembly comprising:

a pair of anchors that are moveable between an open position and a closed position;

an anchor actuation shaft operably coupled to the pair of anchors;

a first clasp that is moveable between an open position and a closed position;

a first clasp control member coupled to the first clasp configured such that applying tension to the first clasp control member moves the first clasp to the open position;

a second clasp that is moveable between an open position and a closed position, a second clasp control member coupled to the second clasp configured such that applying tension to the second clasp control member moves the second clasp to the open position;

an elongate shaft having a proximal portion and a distal portion;

a handle connected to the proximal portion of the elongate shaft;

wherein the anchor actuation shaft extends into the distal portion of the elongate shaft, through the elongate shaft, out of the proximal portion of the elongate shaft, and into the handle;

wherein axial movement of the anchor actuation shaft relative to the elongate shaft moves the pair of anchors between the open position and the closed position;

wherein the first clasp control member extends from the first clasp, into the distal portion of the elongate shaft, through the elongate shaft, out of the proximal portion of the elongate shaft, and through the handle;

wherein the second clasp control member extends from the second clasp, into the distal portion of the elongate shaft, through the elongate shaft, out of the proximal portion of the elongate shaft, and through the handle;

an actuator coupled to the handle, the actuator comprising:
- a first side portion connected to the first clasp control member; and
- a second side portion connected to the second clasp control member;

wherein the first side portion and the second side portion are releasably couplable such that when the first side portion and the second side portion are coupled, proximal movement of the actuator proximally tensions both the first clasp control member and the second clasp control member to move both the first and second clasps to the open position, and such that when the first side portion and the second side portions are uncoupled, individual proximal movements of the first side portion and the second side portion individually tension the first clasp control member and the second clasp control member to independently open the first and second clasps, respectively.

19. The delivery assembly of claim 18 wherein the first clasp control member extends through a first control member lumen in the handle, the second clasp control member extends through a second control member lumen in the handle, and at least a portion of the first control member lumen extends proximally at an angle toward the second control member lumen.

20. The delivery assembly of claim 18 wherein the first clasp control member extends through a first control member lumen in the handle;

wherein the second clasp control member extends through a second control member lumen in the handle;

wherein the anchor actuation shaft extends through an anchor actuation shaft lumen in the handle;

wherein a first portion of the first control member lumen is parallel to the anchor actuation shaft lumen; and wherein a second portion of the first control member lumen extends at an angle relative to the anchor actuation shaft lumen.

\* \* \* \* \*